(12) United States Patent
Stelfox et al.

(10) Patent No.: US 11,391,571 B2
(45) Date of Patent: Jul. 19, 2022

(54) METHOD, APPARATUS, AND COMPUTER PROGRAM FOR ENHANCEMENT OF EVENT VISUALIZATIONS BASED ON LOCATION DATA

(71) Applicant: Zebra Technologies Corporation, Lincolnshire, IL (US)

(72) Inventors: Jill Stelfox, San Jose, CA (US); Dean Lodwig, West Hills, CA (US); James J. O'Hagan, McHenry, IL (US); Michael A. Wohl, Talbott, TN (US)

(73) Assignee: Zebra Technologies Corporation, Lincolnshire, IL (US)

( * ) Notice: Subject to any disclaimer, the term of this patent is extended or adjusted under 35 U.S.C. 154(b) by 0 days.

(21) Appl. No.: 16/368,521

(22) Filed: Mar. 28, 2019

(65) Prior Publication Data
US 2019/0293431 A1   Sep. 26, 2019

Related U.S. Application Data

(63) Continuation of application No. 14/732,369, filed on Jun. 5, 2015, now abandoned.
(Continued)

(51) Int. Cl.
*A63F 13/65* (2014.01)
*G01C 21/16* (2006.01)
(Continued)

(52) U.S. Cl.
CPC .......... *G01C 21/165* (2013.01); *A61B 5/1113* (2013.01); *A61B 5/1118* (2013.01);
(Continued)

(58) Field of Classification Search
CPC ...... A63F 13/65; A63F 13/812; A63F 13/828; A63F 13/00; G01C 21/165; A61B 5/1113;
(Continued)

(56) References Cited

U.S. PATENT DOCUMENTS

| 3,732,500 A | 5/1973 | Dishal et al. |
| 4,270,145 A | 6/1981 | Farina |

(Continued)

FOREIGN PATENT DOCUMENTS

| EP | 1235077 A2 | 8/2002 |
| EP | 1241616 A2 | 9/2002 |

(Continued)

OTHER PUBLICATIONS

International Search Report and Written opinion from International Application No. PCT/US2014/040881 dated Nov. 4, 2014. (available in U.S. Appl. No. 14/732,369, to which priority is claimed.).
(Continued)

*Primary Examiner* — Tramar Harper
*Assistant Examiner* — Jeffrey K Wong

(57) ABSTRACT

An example method for providing enhanced event visualizations based on location data includes receiving, by a visualization processor, location data and sensor data for a plurality of participants; determining an impact indication for two or more participants of the plurality of participants based at least in part on the location data and sensor data; determining, by the visualization processor, a location of impact based on the impact indication and the location data and sensor data for the two or more participants; and generating an impact visualization interface configured to visually indicate impact data associated with the impact indication proximate the impact location.

21 Claims, 19 Drawing Sheets

Related U.S. Application Data

(60) Provisional application No. 62/008,304, filed on Jun. 5, 2014.

(51) Int. Cl.

| | | |
|---|---|---|
| *A63F 13/812* | (2014.01) | |
| *A63F 13/828* | (2014.01) | |
| *A61B 5/11* | (2006.01) | |
| *A61B 5/00* | (2006.01) | |
| *A63F 13/00* | (2014.01) | |
| *G01S 5/02* | (2010.01) | |
| *G01S 19/48* | (2010.01) | |
| *G06Q 10/06* | (2012.01) | |
| *G06V 40/20* | (2022.01) | |
| *A61B 5/02* | (2006.01) | |
| *A63B 24/00* | (2006.01) | |
| *G01S 19/19* | (2010.01) | |
| *G01S 19/41* | (2010.01) | |
| *G01S 19/49* | (2010.01) | |

(52) U.S. Cl.
CPC .......... *A61B 5/6802* (2013.01); *A63F 13/00* (2013.01); *A63F 13/65* (2014.09); *A63F 13/812* (2014.09); *A63F 13/828* (2014.09); *G01S 5/0263* (2013.01); *G01S 19/48* (2013.01); *G06Q 10/0639* (2013.01); *G06V 40/23* (2022.01); *A61B 5/02* (2013.01); *A61B 5/1121* (2013.01); *A61B 5/1127* (2013.01); *A61B 2503/10* (2013.01); *A61B 2505/09* (2013.01); *A61B 2562/0219* (2013.01); *A63B 2024/0025* (2013.01); *A63B 2024/0028* (2013.01); *A63B 2024/0056* (2013.01); *A63B 2024/0068* (2013.01); *A63B 2220/14* (2013.01); *A63B 2220/30* (2013.01); *A63B 2220/40* (2013.01); *A63B 2220/62* (2013.01); *A63B 2220/70* (2013.01); *A63B 2220/801* (2013.01); *A63B 2220/803* (2013.01); *A63B 2220/805* (2013.01); *A63B 2220/806* (2013.01); *A63B 2220/836* (2013.01); *A63B 2225/02* (2013.01); *A63B 2225/50* (2013.01); *A63B 2225/54* (2013.01); *A63B 2230/01* (2013.01); *A63B 2230/06* (2013.01); *A63B 2230/08* (2013.01); *A63B 2230/50* (2013.01); *G01S 19/19* (2013.01); *G01S 19/41* (2013.01); *G01S 19/49* (2013.01)

(58) Field of Classification Search
CPC ....... A61B 5/1118; A61B 5/6802; A61B 5/02; A61B 5/1121; A61B 5/1127; A61B 2503/10; A61B 2505/09; A61B 2562/0219; A01S 5/0263; A01S 5/48; G06K 9/00342; G06Q 10/0639; A63B 2024/0068; A63B 2024/14; A63B 2024/30; A63B 2024/40; A63B 2024/62; A63B 2024/70; A63B 2024/801; A63B 2024/803; A63B 2024/805; A63B 2024/0025; A63B 2024/0028; A63B 2024/0056; A63B 2220/806; A63B 2220/836; A63B 2225/05; A63B 2225/5054; A63B 2230/01; A63B 2230/06; A63B 2230/08; A63B 2230/50; G01S 19/19; G01S 19/41; G01S 19/49
See application file for complete search history.

(56) References Cited

U.S. PATENT DOCUMENTS

| | | |
|---|---|---|
| 5,046,133 A | 9/1991 | Watanabe et al. |
| 5,119,104 A | 6/1992 | Heller |
| 5,469,409 A | 11/1995 | Anderson et al. |
| 5,513,854 A | 5/1996 | Daver |
| 5,645,077 A | 7/1997 | Foxlin |
| 5,699,244 A | 12/1997 | Clark et al. |
| 5,901,172 A | 5/1999 | Fontana et al. |
| 5,920,287 A | 7/1999 | Belcher et al. |
| 5,930,741 A | 7/1999 | Kramer |
| 5,995,046 A | 11/1999 | Belcher et al. |
| 6,028,626 A | 2/2000 | Aviv |
| 6,121,926 A | 9/2000 | Belcher et al. |
| 6,176,837 B1 | 1/2001 | Foxlin |
| 6,204,813 B1 | 3/2001 | Wadell et al. |
| 6,366,242 B1 | 4/2002 | Boyd et al. |
| 6,380,894 B1 | 4/2002 | Boyd et al. |
| 6,593,885 B2 | 7/2003 | Wisherd et al. |
| 6,655,582 B2 | 10/2003 | Wohl et al. |
| 6,710,713 B1 * | 3/2004 | Russo ............... A63B 24/0021 340/573.1 |
| 6,812,884 B2 | 11/2004 | Richley et al. |
| 6,836,744 B1 | 12/2004 | Asphahani et al. |
| 6,882,315 B2 | 4/2005 | Richley et al. |
| 7,009,638 B2 | 3/2006 | Gruber et al. |
| 7,190,271 B2 | 3/2007 | Boyd et al. |
| 7,263,133 B1 | 8/2007 | Miao |
| 7,667,604 B2 | 2/2010 | Ebert et al. |
| 7,671,802 B2 | 3/2010 | Walsh et al. |
| 7,710,322 B1 | 5/2010 | Ameti et al. |
| 7,739,076 B1 | 6/2010 | Vock et al. |
| 7,755,541 B2 | 7/2010 | Wisherd et al. |
| 7,899,006 B2 | 3/2011 | Boyd |
| 7,969,348 B2 | 6/2011 | Baker et al. |
| 8,009,727 B2 | 8/2011 | Hui et al. |
| 8,023,917 B2 | 9/2011 | Popescu |
| 8,077,981 B2 | 12/2011 | Elangovan et al. |
| 8,269,835 B2 | 9/2012 | Grigsby |
| 8,279,051 B2 | 10/2012 | Khan |
| 8,289,185 B2 | 10/2012 | Alonso |
| 8,477,046 B2 | 3/2013 | Alonso |
| 8,457,392 B2 | 6/2013 | Cavallaro et al. |
| 8,568,278 B2 | 10/2013 | Riley et al. |
| 8,665,152 B1 | 3/2014 | Kling et al. |
| 8,696,458 B2 | 4/2014 | Foxlin et al. |
| 8,705,671 B2 | 4/2014 | Ameti et al. |
| 8,731,239 B2 | 5/2014 | Gefen |
| 8,775,916 B2 | 7/2014 | Pulsipher et al. |
| 8,795,045 B2 | 8/2014 | Sorrells et al. |
| 8,842,002 B2 | 9/2014 | Rado |
| 8,780,204 B2 | 10/2014 | DeAngelis et al. |
| 8,989,880 B2 | 3/2015 | Wohl et al. |
| 9,081,076 B2 | 7/2015 | DeAngelis et al. |
| 9,375,628 B2 | 6/2016 | DeAangelis et al. |
| 9,381,645 B1 | 7/2016 | Yarlagadda et al. |
| 9,489,552 B2 | 11/2016 | Hansen |
| 2001/0010541 A1 | 8/2001 | Fernandez et al. |
| 2001/0030625 A1 | 10/2001 | Doles et al. |
| 2002/0004398 A1 | 1/2002 | Ogino et al. |
| 2002/0041284 A1 | 4/2002 | Konishi et al. |
| 2002/0114493 A1 | 8/2002 | McNitt et al. |
| 2002/0116147 A1 | 8/2002 | Vock et al. |
| 2002/0130835 A1 | 9/2002 | Brosnan |
| 2002/0135479 A1 | 9/2002 | Belcher et al. |
| 2003/0090387 A1 | 5/2003 | Lestienne et al. |
| 2003/0095186 A1 | 5/2003 | Aman et al. |
| 2003/0128100 A1 | 7/2003 | Burkhardt et al. |
| 2003/0163287 A1 | 8/2003 | Vock et al. |
| 2003/0227453 A1 | 12/2003 | Beier et al. |
| 2004/0022227 A1 | 2/2004 | Lynch et al. |
| 2004/0062216 A1 | 4/2004 | Nicholls et al. |
| 2004/0108954 A1 | 6/2004 | Richley et al. |
| 2004/0178960 A1 | 9/2004 | Sun |
| 2004/0249969 A1 | 12/2004 | Price |
| 2004/0260470 A1 | 12/2004 | Rast |
| 2004/0260828 A1 | 12/2004 | Price |

(56) References Cited

U.S. PATENT DOCUMENTS

| | | |
|---|---|---|
| 2005/0026563 A1 | 2/2005 | Leeper et al. |
| 2005/0031043 A1 | 2/2005 | Paquelet |
| 2005/0059998 A1 | 3/2005 | Norte et al. |
| 2005/0075079 A1 | 4/2005 | Jei et al. |
| 2005/0093976 A1 | 5/2005 | Valleriano |
| 2005/0148281 A1 | 7/2005 | Sanchez-Castro et al. |
| 2005/0207617 A1 | 9/2005 | Sarnoff |
| 2006/0067324 A1 | 3/2006 | Kim |
| 2006/0139167 A1 | 6/2006 | Davie et al. |
| 2006/0164213 A1 | 7/2006 | Burghard et al. |
| 2006/0252476 A1 | 11/2006 | Bahou |
| 2006/0264730 A1 | 11/2006 | Stivoric et al. |
| 2006/0271912 A1 | 11/2006 | Mickle et al. |
| 2006/0281061 A1 | 12/2006 | Hightower et al. |
| 2007/0018820 A1 | 1/2007 | Chand et al. |
| 2007/0091292 A1 | 4/2007 | Cho et al. |
| 2007/0176749 A1 | 8/2007 | Boyd et al. |
| 2007/0296723 A1 | 12/2007 | Williams |
| 2008/0001714 A1 | 1/2008 | Ono |
| 2008/0065684 A1 | 4/2008 | Zilberman |
| 2008/0106381 A1 | 5/2008 | Adamec et al. |
| 2008/0113787 A1 | 5/2008 | Alderucci |
| 2008/0129825 A1 | 6/2008 | DeAngelis et al. |
| 2008/0140233 A1 | 6/2008 | Seacat |
| 2008/0182724 A1 | 7/2008 | Guthrie |
| 2008/0186231 A1 | 8/2008 | Aljadeff et al. |
| 2008/0204248 A1 | 8/2008 | Winget et al. |
| 2008/0224866 A1 | 9/2008 | Rehman |
| 2008/0246613 A1 | 10/2008 | Linstrom |
| 2008/0262885 A1 | 10/2008 | Jain et al. |
| 2008/0266131 A1 | 10/2008 | Richardson et al. |
| 2008/0269016 A1 | 10/2008 | Ungari et al. |
| 2008/0281443 A1 | 11/2008 | Rogers |
| 2008/0285805 A1 | 11/2008 | Luinge et al. |
| 2008/0291024 A1 | 11/2008 | Zhang et al. |
| 2009/0048044 A1 | 2/2009 | Oleson et al. |
| 2009/0160622 A1 | 6/2009 | Bauchot |
| 2009/0195401 A1 | 8/2009 | Maroney et al. |
| 2009/0210078 A1 | 8/2009 | Crowley |
| 2009/0231198 A1 | 9/2009 | Walsh et al. |
| 2010/0026809 A1 | 2/2010 | Curry |
| 2010/0030350 A1 | 2/2010 | House et al. |
| 2010/0045508 A1 | 2/2010 | Ekbal et al. |
| 2010/0054304 A1 | 3/2010 | Barnes et al. |
| 2010/0060452 A1 | 3/2010 | Schuster et al. |
| 2010/0073188 A1 | 3/2010 | Mickle |
| 2010/0080163 A1 | 4/2010 | Krishnamoorthi et al. |
| 2010/0117837 A1 | 5/2010 | Stirling et al. |
| 2010/0150117 A1 | 6/2010 | Aweya et al. |
| 2010/0174506 A1 | 7/2010 | Joseph et al. |
| 2010/0250305 A1 | 9/2010 | Lee et al. |
| 2010/0278386 A1 | 11/2010 | Hoeflinger |
| 2010/0283630 A1 | 11/2010 | Alonso |
| 2010/0328073 A1 | 12/2010 | Nikitin et al. |
| 2011/0002223 A1 | 1/2011 | Gross |
| 2011/0013087 A1 | 1/2011 | House et al. |
| 2011/0025496 A1 | 2/2011 | Cova |
| 2011/0025847 A1 | 2/2011 | Park et al. |
| 2011/0054782 A1 | 3/2011 | Kaahui et al. |
| 2011/0063114 A1 | 3/2011 | Ikoyan |
| 2011/0064023 A1 | 3/2011 | Yamamoto et al. |
| 2011/0084806 A1 | 4/2011 | Pekins et al. |
| 2011/0134240 A1 | 6/2011 | Anderson et al. |
| 2011/0140970 A1 | 6/2011 | Fukagawa et al. |
| 2011/0151953 A1 | 6/2011 | Kim et al. |
| 2011/0159939 A1 | 6/2011 | Lin |
| 2011/0169959 A1 | 7/2011 | DeAngelis et al. |
| 2011/0261195 A1 | 10/2011 | Martin et al. |
| 2011/0300905 A1 | 12/2011 | Levi |
| 2011/0320322 A1 | 12/2011 | Roslak et al. |
| 2012/0014278 A1 | 1/2012 | Ameti et al. |
| 2012/0015665 A1 | 1/2012 | Farley et al. |
| 2012/0024516 A1 | 2/2012 | Bhadurt et al. |
| 2012/0042326 A1 | 2/2012 | Jain et al. |
| 2012/0057634 A1 | 3/2012 | Shi et al. |
| 2012/0057640 A1 | 3/2012 | Shi et al. |
| 2012/0065483 A1 | 3/2012 | Chung et al. |
| 2012/0081531 A1 | 4/2012 | DeAngelis et al. |
| 2012/0112904 A1 | 5/2012 | Nagy et al. |
| 2012/0126973 A1 | 5/2012 | DeAngelis et al. |
| 2012/0136231 A1 | 5/2012 | Market |
| 2012/0139708 A1 | 6/2012 | Paradiso et al. |
| 2012/0184878 A1 | 7/2012 | Najafi et al. |
| 2012/0212505 A1 | 8/2012 | Burroughs et al. |
| 2012/0218301 A1 | 8/2012 | Miller |
| 2012/0225676 A1 | 9/2012 | Boyd et al. |
| 2012/0231739 A1 | 9/2012 | Chen et al. |
| 2012/0246795 A1 | 10/2012 | Scheffler et al. |
| 2012/0256745 A1 | 10/2012 | Plett et al. |
| 2012/0268239 A1 | 10/2012 | Ljung et al. |
| 2013/0003860 A1 | 1/2013 | Sasai et al. |
| 2013/0021142 A1 | 1/2013 | Matsui et al. |
| 2013/0021206 A1 | 1/2013 | Hach et al. |
| 2013/0041590 A1 | 2/2013 | Burich et al. |
| 2013/0066448 A1* | 3/2013 | Alonso ............ H04Q 9/00 700/91 |
| 2013/0076645 A1 | 3/2013 | Anantha et al. |
| 2013/0096704 A1 | 4/2013 | Case |
| 2013/0115904 A1 | 5/2013 | Kapoor et al. |
| 2013/0138386 A1 | 5/2013 | Jain et al. |
| 2013/0142384 A1 | 6/2013 | Ofek |
| 2013/0257598 A1 | 10/2013 | Kawaguchi et al. |
| 2013/0268185 A1 | 10/2013 | Rabbath et al. |
| 2013/0289382 A1 | 10/2013 | Karaoguz et al. |
| 2013/0339156 A1 | 12/2013 | Sanjay et al. |
| 2014/0055588 A1 | 2/2014 | Bangera et al. |
| 2014/0062728 A1 | 3/2014 | Soto et al. |
| 2014/0074510 A1 | 3/2014 | McClung et al. |
| 2014/0145828 A1 | 5/2014 | Bassan-Eskenazi |
| 2014/0156036 A1 | 6/2014 | Huang |
| 2014/0170607 A1 | 6/2014 | Hsiao et al. |
| 2014/0221137 A1 | 8/2014 | Krysiak et al. |
| 2014/0320660 A1 | 10/2014 | DeAngelis et al. |
| 2014/0347193 A1 | 11/2014 | Ljung |
| 2014/0361875 A1 | 12/2014 | O'Hagan et al. |
| 2014/0361906 A1 | 12/2014 | Hughes et al. |
| 2014/0364141 A1 | 12/2014 | O'Hagan et al. |
| 2014/0365415 A1 | 12/2014 | Stelfox et al. |
| 2015/0002272 A1 | 1/2015 | Alonso et al. |
| 2015/0057981 A1 | 2/2015 | Gross |
| 2015/0085111 A1 | 3/2015 | Lavery |
| 2015/0097653 A1 | 4/2015 | Gibbs et al. |
| 2015/0358852 A1 | 12/2015 | Richley et al. |
| 2015/0360133 A1 | 12/2015 | MacCallum et al. |
| 2015/0375041 A1 | 12/2015 | Richley et al. |
| 2015/0375083 A1 | 12/2015 | Stelfox et al. |
| 2015/0379387 A1 | 12/2015 | Richley |
| 2016/0008693 A1 | 1/2016 | Cronin |
| 2016/0027325 A1 | 1/2016 | Mlhortra |
| 2016/0059075 A1 | 3/2016 | Molyneux et al. |
| 2016/0097837 A1 | 4/2016 | Richley et al. |
| 2017/0100633 A1 | 4/2017 | DeAngelis et al. |

FOREIGN PATENT DOCUMENTS

| | | |
|---|---|---|
| EP | 1253438 A2 | 10/2002 |
| EP | 1503513 A1 | 2/2005 |
| EP | 2474939 A1 | 11/2012 |
| WO | WO 1998005977 | 2/1998 |
| WO | WO 1999061936 A1 | 12/1999 |
| WO | WO 2001008417 | 2/2001 |
| WO | WO 2006022548 | 3/2006 |
| WO | WO 2010083943 | 7/2010 |
| WO | WO 2012167301 | 12/2012 |
| WO | WO 2015051813 | 4/2014 |
| WO | WO 2014197600 | 12/2014 |

OTHER PUBLICATIONS

International Search Report and Written opinion from International Application No. PCT/US2014/040940 dated Dec. 17, 2014. (available in U.S. Appl. No. 14/732,369, to which priority is claimed.).

(56) References Cited

OTHER PUBLICATIONS

Complaint before the United States District Court of Massachusetts, Civil Action No. 1:15-cv-12297, *Lynx System Developers, Inc. et al. V. Zebra Enterprise Solutions Corporation et al.*, filed Jun. 10, 2015.(available in U.S. Appl. No. 14/732,369, to which priority is claimed.).
International Search Report and Written Opinion from International Application No. PCT/US2014/041062 dated Oct. 1, 2014.(available in U.S. Appl. No. 14/732,369, to which priority is claimed.).
International Search Report and Written Opinion from International Application No. PCT/US2014/040947 dated Oct. 9, 2014.(available in U.S. Appl. No. 14/732,369, to which priority is claimed.).
Fontana, R.J., Richley, E., Barney, J., "Commercialization of an Ultra Wideband Precision Asset Location System", *2003 IEEE Conference on Ultra Wideband Systems and Technologie s*, Nov. 16-19, 2003.(available in U.S. Appl. No. 14/732,369, to which priority is claimed.).
Guéziec, A., "Tracking a Baseball Pitch for Broadcast Television," *Computer*, Mar. 2002, pp. 38-43 <http://www.trianglesoftware.com/pitch_tracking.htm>.(available in U.S. Appl. No. 14/732,369, to which priority is claimed.).
CattleLog Pro, *eMerge Interactive, Inc* ., Sebastian, FL, 2004. (available in U.S. Appl. No. 14/732,369, to which priority is claimed.).
Marchant, J., "Secure Animal Indetification and Source Verification", *JM Communications*, UK, 2002.(available in U.S. Appl. No. 14/732,369, to which priority is claimed.).
"A guide to Using NLIS Approved Ear Tags and Rumen Boluses", National Livestock Identification Scheme, *Meat & Livestock Australia Limited*, North Sydney, Australia, May 2003.(available in U.S. Appl. No. 14/732,369, to which priority is claimed.).
King L., "NAIS Cattle ID Pilot Projects Not Needed, Since Proven Advanced Technology Already Exisits", *ScoringSystem, Inc.*, Sarasota, FL, Dec. 27, 2005. (www.prweb.com/releases2005/12prweb325888.htm).(available in U.S. Appl. No. 14/732,369, to which priority is claimed.).
"RFID in the Australian Meat and Livestock Industry", Allflex Australia Pty Ltd., Capalaba, QLD (AU), *Data Capture Suppliers Guide, 2003-2004.* (available in U.S. Appl. No. 14/732,369, to which priority is claimed.).
Swedberg, Claire, "USDA Reseachers Develop System to Track Livestock Feeding Behavior Unobtrusively", RFID Journal, Jul. 18, 2013.(available in U.S. Appl. No. 14/732,369, to which priority is claimed.).
Invitation to Pay Additional Fees/Partial International Search Report for PCT/IB2015/054099 dated Oct. 6, 2015.(available in U.S. Appl. No. 14/732,369, to which priority is claimed.).
Swedberg, C., "N.J. Company Seeks to Market Passive Sensor RFID Tags," *RFID Journal* , Jun. 14, 2011, pp. 1-2 <http://www.rfidjournal.com/articles/pdf?8527>.(available in U.S. Appl. No. 14/732,369, to which priority is claimed.).
International Search Report and Written Opinion for International Application No. PCT/IB2015/054099 dated Dec. 9, 2015.(available in U.S. Appl. No. 14/732,369, to which priority is claimed.).
U.S. Appl. No. 14/296,703, filed Jun. 5, 2014; In re: Alonso et al., entitle Method and Apparatus for Associating Radio Frequency Identification Tags with Participants.(available in U.S. Appl. No. 14/732,369, to which priority is claimed.).
U.S. Appl. No. 61/895,548, filed Oct. 25, 2013, In re: Alonso et al., entitled "Method, Apparatus, and Computer Program Product for Collecting Sporting Event Data Based on Real Time Data for Proximity and Movement of Objects." (available in U.S. Appl. No. 14/732,369, to which priority is claimed.).
International Search Report and Written Opinion for International Application No. PCT/IB2015/059264 dated Feb. 10, 2016. (available in U.S. Appl. No. 14/732,369, to which priority is claimed.).
Jinyun Zhang et al., "UWB Systems for Wireless Sensor Networks", Proceedings of the IEEE, IEEE. New York, US, vol. 97, No. 2, Feb. 1, 2009 (Feb. 1, 2009), pp. 313-331.(available in U.S. Appl. No. 14/732,369, to which priority is claimed.).
International Search Report and Written Opinion for International Application No. PCT/US2015/034267 dated Sep. 25, 2015. (available in U.S. Appl. No. 14/732,369, to which priority is claimed.).
International Search Report and Written Opinion for International Application No. PCT/IB2015/054103 dated Aug. 14, 2015. (available in U.S. Appl. No. 14/732,369, to which priority is claimed.).
Cheong, P. et al., "Synchronization, TOA and Position Estimation for Low-Complexity LDR UWB Devices", Ultra-Wideband, 2005 IEEE International Conference, Zurich, Switzerland Sep. 5-8, 2005, Piscataway, NJ, USA, IEEE, Sep. 5, 2005, pp. 480-484.(available in U.S. Appl. No. 14/732,369, to which priority is claimed.).
International Search Report and Written Opinion for International Application No. PCT/IB2015/054213 dated Aug. 6, 2015.(available in U.S. Appl. No. 14/732,369, to which priority is claimed.).
Wang, Y. et al., "An Algorithmic and Systematic Approach from Improving Robustness of TOA-Based Localization", 2013 IEEE 10th International Conference on High Performance Computing and Communications & 2013 IEEE, Nov. 13, 2013, pp. 2066-2073. (available in U.S. Appl. No. 14/732,369, to which priority is claimed.).
Guvenc, I. et al., "A Survey on TOA Based Wireless Localization and NLOA Mitigation Techniques", IEEE Communications Surveys, IEEE, New York, NY, US, vol. 11, No. 3, Oct. 1, 2009, pp. 107-124.(available in U.S. Appl. No. 14/732,369, to which priority is claimed.).
International Search Report and Written Opinion for International Application PCT/IB2015/054102 dated Nov. 4, 2015.(available in U.S. Appl. No. 14/732,369, to which priority is claimed.).
"Seattleite wins top prize in Microsoft's Super Bowl tech Contest", San Francisco AP, Komonews.com, Feb. 6, 2016. <http://komonews.com/news/local/seattleite-wins-top-prize-in-microsofts-super-bowl-tech-contest>.(available in U.S. Appl. No. 14/732,369, to which priority is claimed.).
Bahle et al., "I See You: How to Improve Wearable Activity Recognition by Leveraging Information from Environmental Cameras," Pervasive Computing and Communications Workshops, IEEE International Conference, (Mar. 18-22, 2013).(available in U.S. Appl. No. 14/732,369, to which priority is claimed.).
Teixeira et al., "Tasking Networked CCTV Cameras and Mobile Phones to Identify and Localize Multiple People," Ubicomp '10 Proceedings of the 12th ACM International Conference on Ubiquitous Computing, pp. 213-222 (Sep. 26-29, 2010).(available in U.S. Appl. No. 14/732,369, to which priority is claimed.).
Complaint before the United States District Court of Massachusetts, Civil Action No. 1:15-cv-12297, *Lynx System Developers, Inc. et al. V. Zebra Enterprise Solutions Corporation et al.*, filed Mar. 23, 2016.(available in U.S. Appl. No. 14/732,369, to which priority is claimed.).
Defendant's Answer to Complaint before the United States District Court of Massachusetts, Civil Action No. 1:15-cv-12297, *Lynx System Developers, Inc. et al. V. Zebra Enterprise Solutions Corporation et al.*, filed Apr. 6, 2016.(available in U.S. Appl. No. 14/732,369, to which priority is claimed.).
International Search Report for International Application No. PCT/US2014/053647 dated Dec. 19, 2014.(available in U.S. Appl. No. 14/732,369, to which priority is claimed.).
International Search Report and Written Opinion for International Application No. PCT/US2016/035614 dated Sep. 15, 2016. (available in U.S. Appl. No. 14/732,369, to which priority is claimed.).
Zhu et al., "A Real-Time Articulated Human Motion Tracking Using Tri-Axis Inertial/Magnetic Sensors Package," IEEE Transactions on Neural Systems and Rehabilitation Engineering, vol. 12, No. 2, Jun. 2004, pp. 295-302.(available in U.S. Appl. No. 14/732,369, to which priority is claimed.).

\* cited by examiner

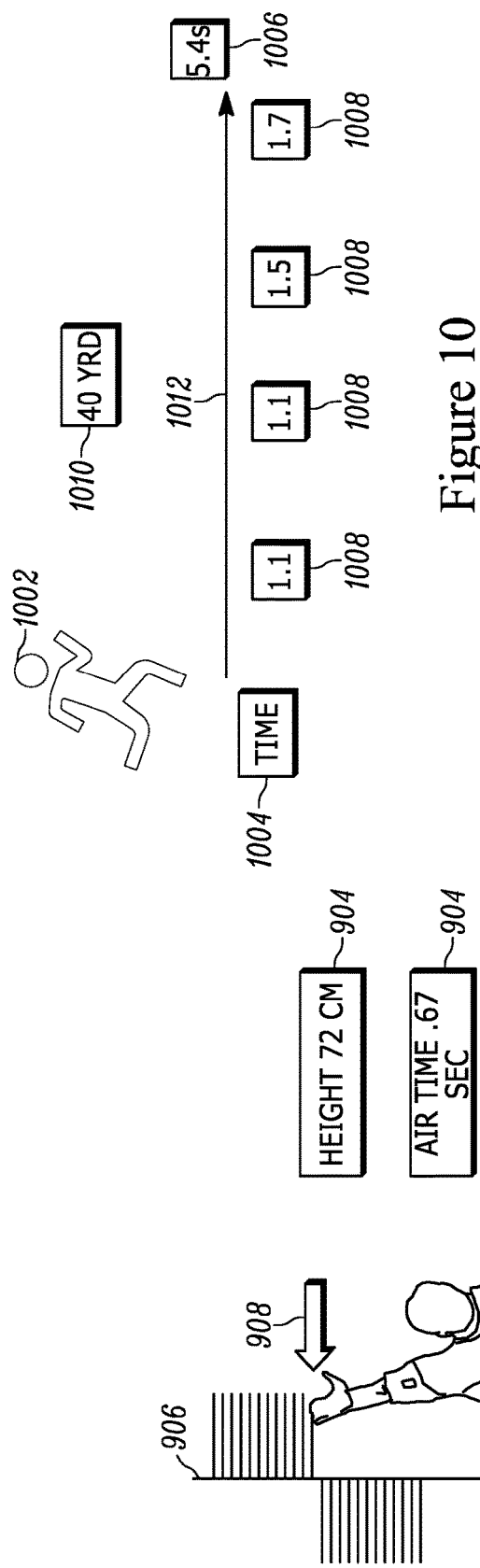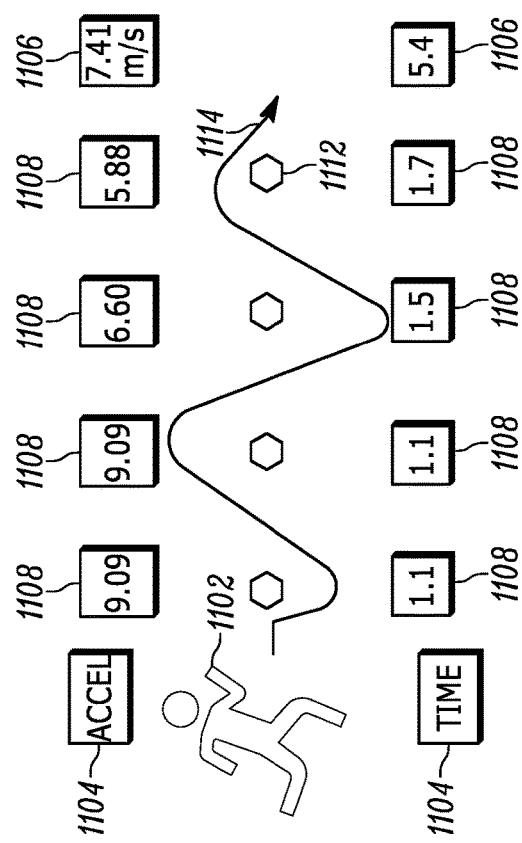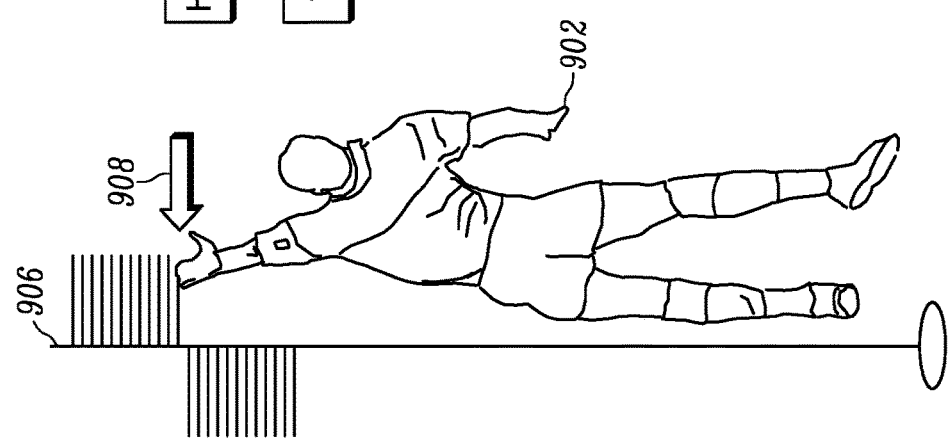
Figure 10
Figure 11
Figure 9

METHOD, APPARATUS, AND COMPUTER PROGRAM FOR ENHANCEMENT OF EVENT VISUALIZATIONS BASED ON LOCATION DATA

CROSS-REFERENCE TO RELATED APPLICATION

This patent arises from a continuation of U.S. patent application Ser. No. 14/732,369, filed Jun. 5, 2015, which claims the benefit of U.S. Provisional Patent Application No. 62/008,304, filed Jun. 5, 2014, which are hereby incorporated herein by reference.

FIELD

Embodiments discussed herein are related to radio frequency locating and, more particularly, to systems, methods, apparatuses, computer readable media and other means for providing enhanced event visualizations based on location data.

BACKGROUND

Event visualizations such as sporting event visualizations may be limited to hand drawn diagrams and overlay drawings by broadcasters, and or overlays of approximate positions on event footage as determined by a broadcaster. These drawing are crudely made over a schematic of the event field or on the event footage, and may require a delay to generate the drawing and overlay before they may be viewed or broadcast.

Statistical information of an event, such as a sporting event, is generally collected manually by watching the event or event footage and entered into a database requiring copious amounts of time and personnel. The data that may be collected is limited to what may be ascertained from viewing the event, and therefore the statistical data and visualizations based thereon are also limited.

Similar to statistical information, event injury notification is limited to a participant raising an issue, which may not occur in highly competitive sporting events or by a spotter viewing the event indicating that an injury may have occurred. The medical staff may need to watch several minutes of event footage to view the injury event and are limited to what cameras may have captured at that time.

BRIEF SUMMARY

Systems, methods, apparatuses, and computer program products are disclosed for providing real-time collection and analysis of monitored individual location, and providing enhanced event visualizations using a locating system, such as a radio frequency locating system, as herein described.

In one example embodiment, a method for providing enhanced event visualizations based on location data is provided including receiving, by a visualizations processor, play diagram data from a play model database; receiving location data during a play period for a plurality of participants; determining a selected play based on comparing the location data to the play diagram data; determining an actual route for one or more participants of the plurality of participants based on the location data; and generating, by the visualization processor, an accuracy visualization interface by comparing the actual route for each of the one or more participants to the selected play.

In some example embodiments, the accuracy visualization interface comprises out of position indicators associated with variances between the actual route and one or more predicted routes drawn from the selected play. In some example embodiments, the out of position indicators visually indicate instances where the actual route varies from the one or more predicted routes by more than a threshold amount.

In some example embodiments, the method further comprises receiving location data for a plurality of opposing participants during the play period; determining a selected opposing play based on comparing the location data for the plurality of opposing participants to the play diagram data; determining an actual opposing route for one or more opposing participants of the plurality of opposing participants based on the location data for the plurality of opposing participants; and generating, by the visualization processor, an opposing accuracy visualization interface by comparing the actual opposing route for each of the one or more participants to the selected opposing play.

In some example embodiments, the opposing accuracy visualization interface comprises out of position indicators associated with variances between the actual opposing route and one or more predicted opposing routes drawn from the selected opposing play.

In some example embodiments, a plurality of accuracy visualization interfaces are generated for a plurality of selected plays occurring during a period of a game. In some example embodiments, a plurality of accuracy visualization interfaces are generated for a plurality of selected plays occurring during a game.

In some example embodiments, the accuracy visualization interface comprises a visual representation of the actual route overlaid relative to one or more predicted routes drawn from the selected play.

In one example embodiment, an apparatus is provided comprising at least one processor; and at least one memory including computer program code, the at least one memory and the computer program code configured to, with the at least one processor, cause the apparatus to at least receive play diagram data from a play model database; receive location data during a play period for a plurality of participants; determine a selected play based on comparing the location data to the play diagram data; determine an actual route for one or more participants of the plurality of participants based on the location data; and generate an accuracy visualization interface by comparing the actual route for each of the one or more participants to the selected play.

In some example embodiments, the accuracy visualization interface comprises out of position indicators associated with variances between the actual route and one or more predicted routes drawn from the selected play.

In some example embodiments, the out of position indicators visually indicate instances where the actual route varies from the one or more predicted routes by more than a threshold amount.

In some example embodiments, the at least one memory and the computer program code are further configured to, with the at least one processor, cause the apparatus to receive location data for a plurality of opposing participants during the play period; determine a selected opposing play based on comparing the location data for the plurality of opposing participants to the play diagram data; determine an actual opposing route for one or more opposing participants of the plurality of opposing participants based on the location data for the plurality of opposing participants; and generate an opposing accuracy visualization interface by comparing the actual opposing route for each of the one or more participants to the selected opposing play.

In some example embodiments, the opposing accuracy visualization interface comprises out of position indicators associated with variances between the actual opposing route and one or more predicted opposing routes drawn from the selected opposing play.

In some example embodiments, a plurality of accuracy visualization interfaces are generated for a plurality of selected plays occurring during a period of a game. In some example embodiments, a plurality of accuracy visualization interfaces are generated for a plurality of selected plays occurring during a game.

In some example embodiments, the accuracy visualization interface comprises a visual representation of the actual route overlaid relative to one or more predicted routes drawn from the selected play.

In one example embodiment, a computer program product is provided comprising at least one computer readable non-transitory memory medium having program code instructions stored thereon, the program code instructions which when executed by an apparatus cause the apparatus at least to receive play diagram data from a play model database; receive location data during a play period for a plurality of participants; determine a selected play based on comparing the location data to the play diagram data; determine an actual route for one or more participants of the plurality of participants based on the location data; and generate an accuracy visualization interface by comparing the actual route for each of the one or more participants to the selected play.

In one example embodiment, a method for providing enhanced event visualizations based on location data is provided that includes receiving, by a visualization processor, formation data, and play data; receive location data during a play period for a plurality of participants; determining, by the visualization processor, one or more receiver participants based on the location data, formation data, and play data; determining, by the visualization processor, one or more opposing participants based on the location data, formation data, and play data; determining one or more open receiver participants from the one or more receiver participants based on comparing location data of the one or more receiver participants to location data of the one or more opposing participants during the play period; and generating, by the visualization processor, an open receiver interface associated configured to visually indicate the one or more open receiver participants.

In some example embodiments, the method further comprises modifying the open receiver interface for each of the one or more open receiver participants based on the degree of openness of each open receiver participant.

In some example embodiments, the method further comprises determining the degree of openness of each open receiver participant based at least in part on a closeness of the one or more opposing participants to each open receiver participant. In some example embodiments, the method further comprises determining the degree of openness of each open receiver participant based at least in part on a velocity vector of the one or more opposing participants in regard to each open receiver participant.

In some example embodiments, the open receiver interface comprises color changing circles associated with each of one or more open receiver participants, wherein a format of the color changing circle is modified based on the degree of openness.

In some example embodiments, the method further comprises determining defensive play data based on the location data, the formation data, and the play data; determining offensive route data based on the location data, the formation data, and the play data; and comparing the defensive play data to the offensive route data to determine when one of the one or more receiver participants is a probable open receiver participant.

In some example embodiments, the method further comprises generating an indication of the probable open receiver participant as part of the open receiver interface.

In one example embodiment, an apparatus is provided comprising at least one processor; and at least one memory including computer program code, the at least one memory and the computer program code configured to, with the at least one processor, cause the apparatus to at least receive formation data and play data; receive location data during a play for a plurality of participants; determine one or more receiver participants based on the location data, formation data, and play data; determine one or more opposing participants based on the location data, formation data, and play data; determine one or more open receiver participants from the one or more receiver participants based on comparing location data of the one or more receiver participants to location data of the one or more opposing participants during the play period; and generate an open receiver interface configured to visually indicate the one or more open receiver participants.

In some example embodiments, the at least one memory and the computer program code are further configured to, with the at least one processor, cause the apparatus to modify the open receiver interface for each of the one or more open receiver participants based on the degree of openness of each open receiver participant.

In some example embodiments, the at least one memory and the computer program code are further configured to, with the at least one processor, cause the apparatus to determine the degree of openness of each open receiver participant based at least in part on a closeness of the one or more opposing participants to each open receiver participant. In some example embodiments, the at least one memory and the computer program code are further configured to, with the at least one processor, cause the apparatus to determine the degree of openness of each open receiver participant based at least in part on a velocity vector of the one or more opposing participants in regard to each open receiver participant.

In some example embodiments, the open receiver interface comprises color changing circles associated with each of one or more open receiver participants, wherein a format of the color changing circle is modified based on the degree of openness.

In some example embodiments, the at least one memory and the computer program code are further configured to, with the at least one processor, cause the apparatus to determine defensive play data based on the location data, the formation data, and the play data; determine offensive route data based on the location data, the formation data, and the play data; and compare the defensive play data to the offensive route data to determine when one of the one or more receiver participants is a probable open receiver participant.

In some example embodiments, the at least one memory and the computer program code are further configured to, with the at least one processor, cause the apparatus to generate an indication of the probable open receiver participant as part of the open receiver interface.

In one example embodiment, a computer program product is provided comprising at least one computer readable non-transitory memory medium having program code instructions stored thereon, the program code instructions which when executed by an apparatus cause the apparatus at least to receive formation data and play data; receive location data during a play period for a plurality of participants; determine one or more receiver participants based on the location data, formation data, and play data; determine one or more opposing participants based on the location data, formation data, and play data; determine one or more open receiver participants from the one or more receiver participants based on comparing location data of the one or more receiver participants to location data of the one or more opposing participants during the play period; and generate an open receiver interface configured to visually indicate the one or more open receiver participants.

In one example embodiment, a method for providing enhanced event visualizations based on location data is provided that includes receiving, by a visualization processor, location data and sensor data for a plurality of participants; determining an impact indication for two or more participants of the plurality of participants based at least in part on the location data and sensor data; determining, by the visualization processor, a location of impact based on the impact indication and the location data and sensor data for the two or more participants; and generating an impact visualization interface configured to visually indicate impact data associated with the impact indication proximate the impact location.

In some example embodiments, the method further comprises determining speed at impact data for each of the two or more participants based at least in part on the location data and sensor data; determining acceleration at impact data for each of the two or more participants based at least in part on the location data and sensor data; and generating speed at impact indicators and acceleration at impact indicators for each of the two or more participants as part of the impact visualization interface.

In some example embodiments, the speed at impact indicator comprises a speed variable arrow trail approaching the location of impact, where the speed variable arrow trail varies in appearance based on the speed at impact data; and wherein the acceleration at impact indicator comprises an acceleration variable arrow trail approaching the location of impact, where the acceleration variable arrow trail varies in appearance based on the acceleration at impact data.

In some example embodiments, the method further comprises determining speed after impact data for each of the two or more participants based at least in part on the location data and sensor data; determining acceleration after impact data for each of the two or more participants based at least in part on location data and sensor data; generating speed after impact indicators and acceleration after impact indicators for each of the two or more participants as part of the impact visualization interface.

In some example embodiments, the speed after impact indicator comprises a speed variable arrow trail departing the location of impact, where the speed variable arrow trail varies in appearance based on the speed after impact data; and wherein the acceleration after impact indicator comprises an acceleration variable arrow trail departing the location of impact, where the acceleration variable arrow trail varies in appearance based on the acceleration after impact data.

In some example embodiments, the method further comprises receiving statistical data for the two or more participants; generating impact statistic information; and providing the impact statistic information as part of the impact visualization interface.

In some example embodiments, the method further comprises receiving participant data for each of the two or more participants, the participant data at least comprising participant mass data; generating force and momentum approaching impact data based on the participant mass data and the f location data and sensor data, and generating the impact visualization interface further based on the force and momentum approaching impact data.

In some example embodiments, the method further comprises determining a starting point for each of the two or more participants based at least in part on the location data; and generating a participant start indicators for each of the two or more participants as part of the impact visualization interface. In some example embodiments, the method further comprises determining a route for each of the two or more participants based at least in part on the location data; and generating participant route indicators for each of the two or more participants as part of the impact visualization interface.

In one example embodiment, an apparatus is provided comprising at least one processor; and at least one memory including computer program code, the at least one memory and the computer program code configured to, with the at least one processor, cause the apparatus to at least receive location data and sensor data for a plurality of participants; determine an impact indication for two or more participants of the plurality of participants based at least in part on the location data and sensor data; determine a location of impact based on the impact indication and the location data and sensor data for the two or more participants; and generate an impact visualization interface configured to visually indicate impact data associated with the impact indication proximate the impact location.

In some example embodiments, the at least one memory and the computer program code are further configured to, with the at least one processor, cause the apparatus to determine speed at impact data for each of the two or more participants based at least in part on the location data and sensor data; determine acceleration at impact data for each of the two or more participants based at least in part on the location data and sensor data; and generate speed at impact indicators and acceleration at impact indicators for each of the two or more participants as part of the impact visualization interface.

In some example embodiments, the speed at impact indicator comprises a speed variable arrow trail approaching the location of impact, where the speed variable arrow trail varies in appearance based on the speed at impact data; and wherein the acceleration at impact indicator comprises an acceleration variable arrow trail approaching the location of impact, where the acceleration variable arrow trail varies in appearance based on the acceleration at impact data.

In some example embodiments, the at least one memory and the computer program code further configured to, with the at least one processor, cause the apparatus to determine speed after impact data for each of the two or more participants based at least in part on the location data and sensor data; determine acceleration after impact data for each of the two or more participants based at least in part on the location data and sensor data; and generate speed after impact indicators and acceleration after impact indicators for each of the two or more participants as part of the impact visualization interface.

In some example embodiments, the speed after impact indicator comprises a speed variable arrow trail departing the location of impact, where the speed variable arrow trail varies in appearance based on the speed after impact data; and wherein the acceleration after impact indicator comprises an acceleration variable arrow trail departing the location of impact, where the acceleration variable arrow trail varies in appearance based on the acceleration after impact data.

In some example embodiments, the at least one memory and the computer program code are further configured to, with the at least one processor, cause the apparatus to receive statistical data for the two or more participants; generate impact statistic information; and provide the impact statistic information as part of the impact visualization interface.

In some example embodiments, the at least one memory and the computer program code are further configured to, with the at least one processor, cause the apparatus to: receive participant data for each of the two or more participants, the participant data at least comprising participant mass data; generate force and momentum approaching impact data based on the participant mass data and the location data and sensor data, and generate the impact visualization interface further based on the force and momentum approaching impact data.

In some example embodiments, the at least one memory and the computer program code are further configured to, with the at least one processor, cause the apparatus to determine a starting point for each of the two or more participants based at least in part on the location data; and generate a participant start indicator for each of the two or more participants as part of the impact visualization interface. In some example embodiments, the at least one memory and the computer program code are further configured to, with the at least one processor, cause the apparatus to determine a route for each of the two or more participants based at least in part on the location data; and generate participant route indicators for each of the two or more participants as part of the impact visualization interface.

In one example embodiment, a computer program product is provided comprising at least one computer readable non-transitory memory medium having program code instructions stored thereon, the program code instructions which when executed by an apparatus cause the apparatus at least to receive location data and sensor data for a plurality of participants; determine an impact indication for two or more participants of the participants based at least in part on the plurality of location data and sensor data; determine a location of impact based on the impact indication and the location data and sensor data for the two or more participants; and generate an impact visualization interface configured to visually indicate impact data associated with the impact indication proximate the impact location.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 illustrates an exemplary environment using a radio frequency locating system for providing performance analytics in accordance with some embodiments of the present invention;

FIGS. 2A-D illustrate some exemplary participants carrying tags and sensors that may provide information to a performance analytics system in accordance with some embodiments of the present invention;

FIGS. 5-23 illustrate example visualizations based on location data in accordance with some embodiments of the present invention.

DETAILED DESCRIPTION

Figure 1:
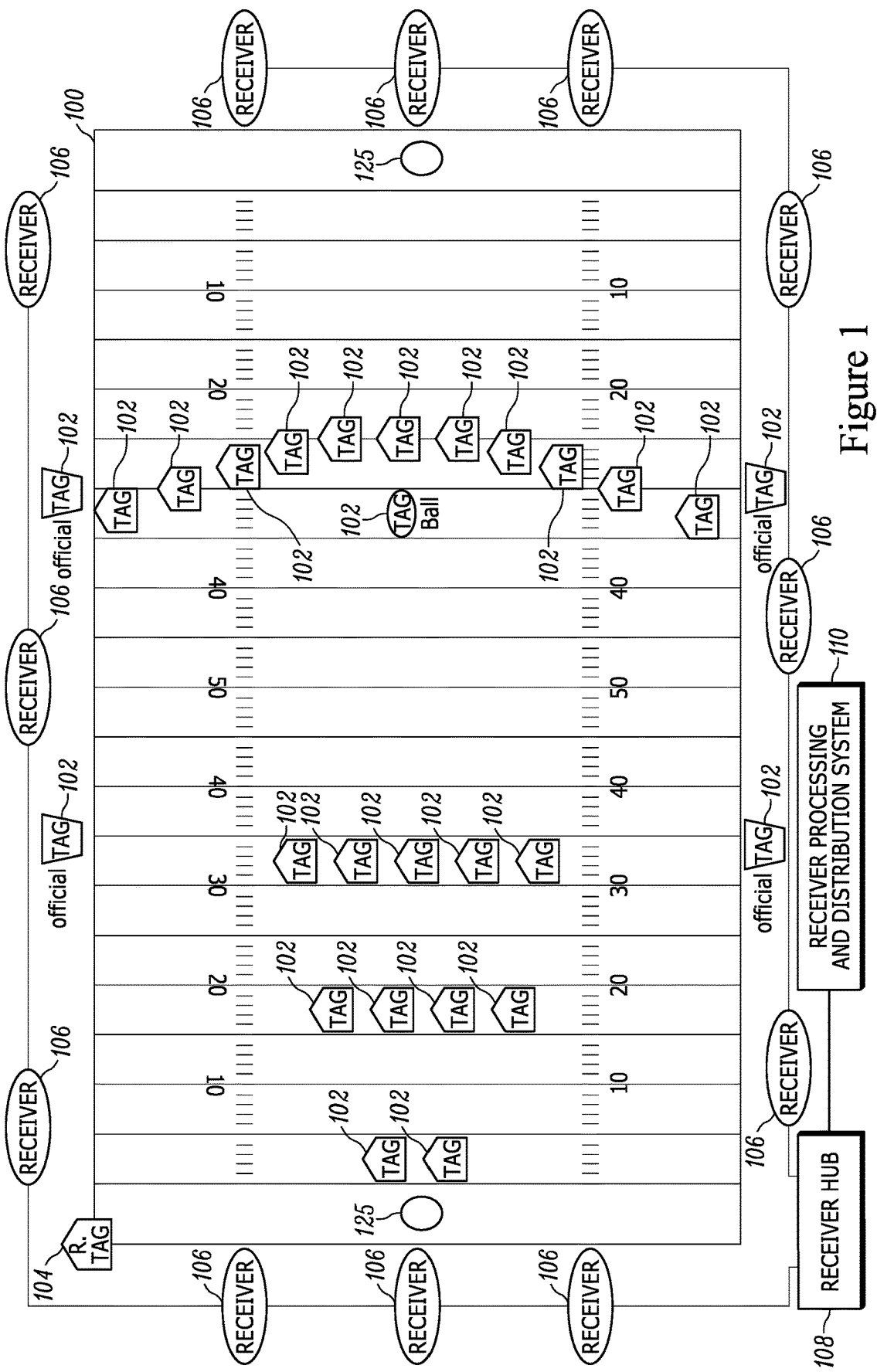

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Overview

The utilization of subfoot location technologies, such as ultra wide band (UWB) locating, may allow for a richer variety in the analytics performed for events, such as American football, European football, basketball, baseball, or the like. The analytics may further allow for new or enhanced visualization outputs to players, coaches, teams, medial staff, broadcasters, fans, or the like, in real time or near real time.

Visualizations may include statistical data charts, graphs and the like based on the locations data and analytics and a real time comparison of the statistical data to historical data, such as statistics for the quarter or game verse a historical average. Similarly the statistical data for participants may be plotted in real time over the course of the event, and used to determine changes in participant performance. The changes in participant performance may be used to evaluate for injury, rotate players, or adjust wager odds for gaming.

The location data may be used to plot the travel of participants on an event field in real time, or overlay the travel of participants on event footage. Effects such as trails, statistic values, e.g., speed, impact force, or the like, may be overlaid on game footage in real time based on the location data. Additionally, visualization illustrations may be generated without user input, depicting formation weaknesses, open receivers, quarterback view of the field, or the like. The location plotting may also be used to compare the actual path of a player to the diagramed path, such as in a play book. The play verse actual travel may also include anticipated opposing player patterns. Analysis of the actual and diagramed player travel may assist coaches and players in execution or adjustment of future plays.

Visualizations may be generated to display new statistical data, such as impact force, acceleration, individual player travel distance, or the like. Additionally, alerts may be generated and visualized for team or medical staff, such as a concussion alert for numerous or severe impacts.

In embodiments, in which a plurality of location tags or sensors are mounted to the participant, a participant motion model may be rendered in a visualization. The participant motion model may allow for better injury diagnosis, and/or performance review and improvement.

Example RF Locating System Architecture

FIGS. 1, 2A-2C, and 4 depict, for illustration purposes, various sporting event (i.e., football) participants (tagged players, a ball, and a referee). However, as will be apparent to one of ordinary skill in the art, the inventive concepts herein described are not limited to application to participants in sporting events and may be applied to other monitored individuals who may be present at a venue of interest.

FIG. 1 illustrates an exemplary locating system 100 useful for calculating a location by an accumulation of location data or time of arrivals (TOAs) at a central processor/hub 108, whereby the TOAs represent a relative time of flight (TOF) from real time locating system (RTLS) tags 102 as recorded at each receiver 106 (e.g., UWB reader, etc.). A timing reference clock is used, in some examples, such that at least a subset of the receivers 106 may be synchronized in frequency, whereby the relative TOA data associated with each of the RTLS tags 102 may be registered by a counter associated with at least a subset of the receivers 106. In some examples, a reference tag 104, preferably a UWB transmitter, positioned at known coordinates, is used to determine a phase offset between the counters associated with at least a subset of the of the receivers 106. The RTLS tags 102 and the reference tags 104 reside in an active RTLS field. The systems described herein may be referred to as either "multilateration" or "geolocation" systems, terms that refer to the process of locating a signal source by solving an error minimization function of a location estimate determined by the difference in time of arrival (DTOA) between TOA signals received at multiple receivers 106.

In some examples, the system comprising at least the tags 102 and the receivers 106 is configured to provide two dimensional and/or three dimensional precision localization (e.g., subfoot resolutions), even in the presence of multipath interference, due in part to the use of short nanosecond duration pulses whose TOF can be accurately determined using detection circuitry, such as in the receivers 106, which can trigger on the leading edge of a received waveform. In some examples, this short pulse characteristic allows necessary data to be conveyed by the system at a higher peak power, but lower average power levels, than a wireless system configured for high data rate communications, yet still operate within local regulatory requirements.

In some examples, to provide a preferred performance level while complying with the overlap of regulatory restrictions (e.g., FCC and ETSI regulations), the tags 102 may operate with an instantaneous −3 dB bandwidth of approximately 400 MHz and an average transmission below 187 pulses in a 1 msec interval, provided that the packet rate is sufficiently low. In such examples, the predicted maximum range of the system, operating with a center frequency of 6.55 GHz, is roughly 200 meters in instances in which a 12 dBi directional antenna is used at the receiver, but the projected range will depend, in other examples, upon receiver antenna gain. Alternatively or additionally, the range of the system allows for one or more tags 102 to be detected with one or more receivers positioned throughout a football stadium used in a professional football context. Such a configuration advantageously satisfies constraints applied by regulatory bodies related to peak and average power densities (e.g., effective isotropic radiated power density ("EIRP")), while still optimizing system performance related to range and interference. In further examples, tag transmissions with a −3 dB bandwidth of approximately 400 MHz yields, in some examples, an instantaneous pulse width of roughly 2 nanoseconds that enables a location resolution to better than 30 centimeters.

Referring again to FIG. 1, the object to be located has an attached tag 102, preferably a tag having a UWB transmitter, that transmits a burst (e.g., multiple pulses at a 1 Mb/s burst rate, such as 112 bits of On-Off keying (OOK) at a rate of 1 Mb/s), and optionally, a burst comprising an information packet utilizing OOK that may include, but is not limited to, ID information, a sequential burst count or other desired information for object or personnel identification, inventory control, etc. In some examples, the sequential burst count (e.g., a packet sequence number) from each tag 102 may be advantageously provided in order to permit, at a central processor/hub 108, correlation of TOA measurement data from various receivers 106.

In some examples, the tag 102 may employ UWB waveforms (e.g., low data rate waveforms) to achieve extremely fine resolution because of their extremely short pulse (i.e., sub-nanosecond to nanosecond, such as a 2 nsec (1 nsec up and 1 nsec down)) durations. As such, the information packet may be of a short length (e.g., 112 bits of OOK at a rate of 1 Mb/sec, in some example embodiments), that advantageously enables a higher packet rate. If each information packet is unique, a higher packet rate results in a higher data rate; if each information packet is transmitted repeatedly, the higher packet rate results in a higher packet repetition rate. In some examples, higher packet repetition rate (e.g., 12 Hz) and/or higher data rates (e.g., 1 Mb/sec, 2 Mb/sec or the like) for each tag may result in larger datasets for filtering to achieve a more accurate location estimate. Alternatively or additionally, in some examples, the shorter length of the information packets, in conjunction with other packet rate, data rates and other system requirements, may also result in a longer battery life (e.g., 7 years battery life at a transmission rate of 1 Hz with a 300 mAh cell, in some present embodiments).

Tag signals may be received at a receiver directly from RTLS tags, or may be received after being reflected en route. Reflected signals travel a longer path from the RTLS tag to the receiver than would a direct signal, and are thus received later than the corresponding direct signal. This delay is known as an echo delay or multipath delay. If reflected signals are sufficiently strong enough to be detected by the receiver, they can corrupt a data transmission through inter-symbol interference. In some examples, the tag 102 may employ UWB waveforms to achieve extremely fine resolution because of their extremely short pulse (e.g., 2 nsec) durations. Furthermore, signals may comprise short information packets (e.g., 112 bits of OOK) at a somewhat high burst data rate (1 Mb/sec, in some example embodiments), that advantageously enable packet durations to be brief (e.g., 112 microsec) while allowing inter-pulse times (e.g., 998 nsec) sufficiently longer than expected echo delays, avoiding data corruption.

Reflected signals can be expected to become weaker as delay increases due to more reflections and the longer distances traveled. Thus, beyond some value of inter-pulse time (e.g., 998 nsec), corresponding to some path length difference (e.g., 299.4 m), there will be no advantage to further increases in inter-pulse time (and, hence lowering of burst data rate) for any given level of transmit power. In this manner, minimization of packet duration allows the battery life of a tag to be maximized, since its digital circuitry need only be active for a brief time. It will be understood that different environments can have different expected echo delays, so that different burst data rates and, hence, packet durations, may be appropriate in different situations depending on the environment.

Minimization of the packet duration also allows a tag to transmit more packets in a given time period, although in practice, regulatory average EIRP limits may often provide an overriding constraint. However, brief packet duration also reduces the likelihood of packets from multiple tags overlapping in time, causing a data collision. Thus, minimal packet duration allows multiple tags to transmit a higher aggregate number of packets per second, allowing for the largest number of tags to be tracked, or a given number of tags to be tracked at the highest rate.

In one non-limiting example, a data packet length of 112 bits (e.g., OOK encoded), transmitted at a data rate of 1 Mb/sec (1 MHz), may be implemented with a transmit tag repetition rate of 1 transmission per second (1 TX/sec). Such an implementation may accommodate a battery life of up to seven years, wherein the battery itself may be, for example, a compact, 3-volt coin cell of the series no. BR2335 (Rayovac), with a battery charge rating of 300 mAhr. An alternate implementation may be a generic compact, 3-volt coin cell, series no. CR2032, with a battery charge rating of 220 mAhr, whereby the latter generic coin cell, as can be appreciated, may provide for a shorter battery life.

Alternatively or additionally, some applications may require higher transmit tag repetition rates to track a dynamic environment. In some examples, the transmit tag repetition rate may be 12 transmissions per second (12 TX/sec). In such applications, it can be further appreciated that the battery life may be shorter.

The high burst data transmission rate (e.g., 1 MHz), coupled with the short data packet length (e.g., 112 bits) and the relatively low repetition rates (e.g., 1 TX/sec), provide for two distinct advantages in some examples: (1) a greater number of tags may transmit independently from the field of tags with a lower collision probability, and/or (2) each independent tag transmit power may be increased, with proper consideration given to a battery life constraint, such that a total energy for a single data packet is less than a regulated average power for a given time interval (e.g., a 1 msec time interval for an FCC regulated transmission).

Alternatively or additionally, additional sensor or telemetry data may be transmitted from the tag to provide the receivers 106 with information about the environment and/or operating conditions of the tag. For example, the tag may transmit a temperature to the receivers 106. Such information may be valuable, for example, in a system involving perishable goods or other refrigerant requirements. In this example embodiment, the temperature may be transmitted by the tag at a lower repetition rate than that of the rest of the data packet. For example, the temperature may be transmitted from the tag to the receivers at a rate of one time per minute (e.g., 1 TX/min.), or in some examples, once every 720 times the data packet is transmitted, whereby the data packet in this example is transmitted at an example rate of 12 TX/sec.

Alternatively or additionally, the tag 102 may be programmed to intermittently transmit data to the receivers 106 in response to a signal from a magnetic command transmitter (not shown). The magnetic command transmitter may be a portable device, functioning to transmit a 125 kHz signal, in some example embodiments, with a range of approximately 15 feet or less, to one or more of the tags 102. In some examples, the tags 102 may be equipped with at least a receiver tuned to the magnetic command transmitter transmit frequency (e.g., 125 kHz) and functional antenna to facilitate reception and decoding of the signal transmitted by the magnetic command transmitter.

In some examples, one or more other tags, such as a reference tag 104, may be positioned within and/or about a monitored region. In some examples, the reference tag 104 may be configured to transmit a signal that is used to measure the relative phase (e.g., the count of free-running counters) of non-resettable counters within the receivers 106.

One or more (e.g., preferably four or more) receivers 106 are also positioned at predetermined coordinates within and/or around the monitored region. In some examples, the receivers 106 may be connected in a "daisy chain" fashion to advantageously allow for a large number of receivers 106 to be interconnected over a significant monitored region in order to reduce and simplify cabling, provide power, and/or the like. Each of the receivers 106 includes a receiver for receiving transmissions, such as UWB transmissions, and preferably, a packet decoding circuit that extracts a time of arrival (TOA) timing pulse train, transmitter ID, packet number, and/or other information that may have been encoded in the tag transmission signal (e.g., material description, personnel information, etc.) and is configured to sense signals transmitted by the tags 102 and one or more reference tags 104.

Each receiver 106 includes a time measuring circuit that measures times of arrival (TOA) of tag bursts, with respect to its internal counter. The time measuring circuit is phase-locked (e.g., phase differences do not change and therefore respective frequencies are identical) with a common digital reference clock signal distributed via cable connection from a central processor/hub 108 having a central timing reference clock generator. The reference clock signal establishes a common timing reference for the receivers 106. Thus, multiple time measuring circuits of the respective receivers 106 are synchronized in frequency, but not necessarily in phase. While there typically may be a phase offset between any given pair of receivers in the receivers 106, the phase offset is readily determined through use of a reference tag 104. Alternatively or additionally, each receiver may be synchronized wirelessly via virtual synchronization without a dedicated physical timing channel.

In some example embodiments, the receivers 106 are configured to determine various attributes of the received signal. Since measurements are determined at each receiver 106, in a digital format, rather than analog in some examples, signals are transmittable to the receiver hub 108. Advantageously, because packet data and measurement results can be transferred at high speeds to a receiver memory, the receivers 106 can receive and process tag (and corresponding object) locating signals on a nearly continuous basis. As such, in some examples, the receiver memory allows for a high burst rate of tag events (i.e., information packets) to be captured.

Data cables or wireless transmissions may convey measurement data from the receivers 106 to the central processor/hub 108 (e.g., the data cables may enable a transfer speed of 2 Mbps). In some examples, measurement data is transferred to the central processor/hub at regular polling intervals.

As such, the central processor/hub 108 determines or otherwise computes tag location (i.e., object location) by processing TOA measurements relative to multiple data packets detected by the receivers 106. In some example embodiments, the central processor/hub 108 may be configured to resolve the coordinates of a tag using nonlinear optimization techniques.

In some examples, TOA measurements from multiple receivers 106 are processed by the Receiver hub 108 to determine a location of the transmit tag 102 by a differential time-of-arrival (DTOA) analysis of the multiple TOAs. The DTOA analysis includes a determination of tag transmit time $t_0$, whereby a time-of-flight (TOF), measured as the time elapsed from the estimated tag transmit time $t_0$ to the respective TOA, represents graphically the radii of spheres centered at respective receivers 106. The distance between the surfaces of the respective spheres to the estimated location coordinates $(x_0, y_0, z_0)$ of the transmit tag 102 represents the measurement error for each respective TOA, and the minimization of the sum of the squares of the TOA measurement errors from each receiver participating in the DTOA location estimate provides for both the location coordinates $(x_0, y_0, z_0)$ of the transmit tag and of that tag's transmit time $t_0$.

In some examples, the system described herein may be referred to as an "over-specified" or "over-determined" system. As such, the central processor/hub 108 may calculate one or more valid (i.e., most correct) locations based on a set of measurements and/or one or more incorrect (i.e., less correct) locations. For example, a location may be calculated that is impossible due the laws of physics or may be an outlier when compared to other calculated locations. As such one or more algorithms or heuristics may be applied to minimize such error.

The starting point for the minimization may be obtained by first doing an area search on a coarse grid of x, y and z over an area defined by the user and followed by a localized steepest descent search. The starting location for this algorithm is fixed, in some examples, at the mean position of all active receivers. No initial area search is needed, and optimization proceeds through the use of a Davidon-Fletcher-Powell (DFP) quasi-Newton algorithm in some examples. In other examples, a steepest descent algorithm may be used.

One such algorithm for error minimization, which may be referred to as a time error minimization algorithm, may be described in Equation 1:

$$\varepsilon = \Sigma_{j=1}^{N}[[(x-x_j)^2+(y-y_j)^2+(z-z_j)^2]^{1/2}-c(t_j-t_0)]^2 \quad (1)$$

Where N is the number of receivers, c is the speed of light, $(x_j, y_j, z_j)$ are the coordinates of the $j^{th}$ receiver, $t_1$ is the arrival time at the $j^{th}$ receiver, and $t_0$ is the tag transmit time. The variable $t_0$ represents the time of transmission. Since $t_0$ is not initially known, the arrival times, $t_j$, as well as $t_0$, are related to a common time base, which in some examples, is derived from the arrival times. As a result, differences between the various arrival times have significance for determining location as well as $t_0$.

The optimization algorithm to minimize the error $\varepsilon$ in Equation 1 may be the Davidon-Fletcher-Powell (DFP) quasi-Newton algorithm, for example. In some examples, the optimization algorithm to minimize the error $\varepsilon$ in Equation 1 may be a steepest descent algorithm. In each case, the algorithms may be seeded with an initial location estimate (x, y, z) that represents the two-dimensional (2D) or three-dimensional (3D) mean of the positions of the receivers 106 that participate in the tag location determination.

In some examples, the RTLS system comprises a receiver grid, whereby each of the receivers 106 in the receiver grid keeps a receiver clock that is synchronized, with an initially unknown phase offset, to the other receiver clocks. The phase offset between any receivers may be determined by use of a reference tag that is positioned at a known coordinate position $(x_T, y_T, z_T)$. The phase offset serves to resolve the constant offset between counters within the various receivers 106, as described below.

In further example embodiments, a number N of receivers 106 $\{R_j: j=1, \ldots, N\}$ are positioned at known coordinates $(x_{R_j}, y_{R_j}, z_{R_j})$, which are respectively positioned at distances $d_{R_j}$ from a reference tag 104, such as given in Equation 2:

$$d_{R_j} = \sqrt{(x_{R_j}-x_T)^2+(y_{R_j}-y_T)^2+(z_{R_j}-z_T)^2} \quad (2)$$

Each receiver $R_j$ utilizes, for example, a synchronous clock signal derived from a common frequency time base, such as a clock generator. Because the receivers are not synchronously reset, an unknown, but constant offset $O_j$ exists for each receiver's internal free running counter. The value of the constant offset $O_j$ is measured in terms of the number of fine resolution count increments (e.g., a number of nanoseconds for a one nanosecond resolution system).

The reference tag is used, in some examples, to calibrate the radio frequency locating system as follows: The reference tag emits a signal burst at an unknown time $\tau_R$. Upon receiving the signal burst from the reference tag, a count $N_{R_j}$ as measured at receiver $R_j$ is given in Equation 3 by:

$$N_{R_j} = \beta\tau_R + O_j + \beta d_{R_j}/c \quad (3)$$

Where c is the speed of light and $\beta$ is the number of fine resolution count increments per unit time (e.g., one per nanosecond). Similarly, each object tag $T_i$ of each object to be located transmits a signal at an unknown time $\tau_i$ to produce a count $N_{ij}$, as given in Equation 4:

$$N_{ij} = \beta\tau_i + O_j + \beta d_{ij}/c \quad (4)$$

at receiver $R_j$ where $d_{ij}$ the distance between the object tag $T_i$ and the receiver 106 $R_j$. Note that $\tau_i$ is unknown, but has the same constant value for all receivers. Based on the equalities expressed above for receivers $R_j$ and $R_k$ and given the reference tag 104 information, phase offsets expressed as differential count values are determined as given in Equations 5a-b:

$$N_{R_j} - N_{R_k} = (O_j - O_k) + \beta\left(\frac{d_{R_j}}{c} - \frac{d_{R_k}}{c}\right) \quad (5a)$$

Or, $$(O_j - O_k) = (N_{R_j} - N_{R_k}) - \beta\left(\frac{d_{R_j}}{c} - \frac{d_{R_k}}{c}\right) = \Delta_{j_k} \quad (5b)$$

Where $\Delta_{jk}$ is constant as long as $d_{Rj}-d_{Rk}$ remains constant, (which means the receivers and reference tag are fixed and there is no multipath situation) and $\beta$ is the same for each receiver. Note that $\Delta_{j_k}$ is a known quantity, since $N_{R_j}$, $N_{R_k}$, $\beta$, $d_{R_j}/c$, and $d_{R_k}/c$ are known. That is, the phase offsets between receivers $R_1$ and $R_k$ may be readily determined based on the reference tag 104 transmissions. Thus, again from the above equations, for a tag 102 ($T_i$) transmission arriving at receivers $R_j$ and $R_k$, one may deduce the following Equations 6a-b:

$$N_{i_j} - N_{i_k} = (O_j - O_k) + \beta\left(\frac{d_{i_j}}{c} - \frac{d_{i_k}}{c}\right) = \Delta_{j_k} + \beta\left(\frac{d_{i_j}}{c} - \frac{d_{i_k}}{c}\right) \quad (6a)$$

Or, $$d_{i_j} - d_{i_k} = (c/\beta)[N_{i_j} - N_{i_k} - \Delta_{j_k}]$$

Each arrival time, $t_j$, can be referenced to a particular receiver (receiver "1") as given in Equation 7:

$$t_j = \frac{1}{\beta}(N_j - \Delta_{j1}) \quad (7)$$

The minimization, described in Equation 1, may then be performed over variables (x, y, z, $t_0$) to reach a solution (x', y', z', $t_0'$).

In some example embodiments, the location of a tag 102 may then be output to a receiver processing and distribution system 110 for further processing of the location data to advantageously provide visualizations, predictive analytics, statistics and/or the like.

The exemplary radio frequency locating system of FIG. 1 may be used in providing performance analytics in accordance with some embodiments of the present invention. In the environment of FIG. 1, data may be captured and analyzed, such as during a sporting event to identify event occurrences, statistics, and other data useful to a sports team, league, viewer, licensee, or the like. In some embodiments, data associated with a number of participants (e.g., players, officials, balls, game equipment, etc.) on a playing field, such as monitored area 100, may be generated and provided to a performance analytics system. As such, as further discussed in connection with FIGS. 2A-C below, each participant may have one or more attached tags 102 (such as to equipment worn by a player) to be used to track data such as location, change of location, speed, or the like of each object. In some embodiments, additional sensors, such as, without limitation, accelerometers, magnetometers, time-of-flight sensors, health sensors, temperature sensors, moisture sensors, light sensors, or the like, may be attached to each object to provide further data to the performance analytics system. Such additional sensors may provide data to the tag 102, either through a wired or wireless connection, to be transmitted to the receivers 106 or the sensors may be configured to transmit data to receivers (i.e., sensor receivers) separately from tags 102.

One or more of the receivers 106 may receive transmissions from tags 102 and transmit the blink data to a central processor/hub 108. The central processor/hub 108 may process the received data to determine tag location for the tags 102. The central processor/hub 108 may transmit the tag location data to one or more processors, such as receiver processing and distribution system 110. Receiver processing and distribution system 110 may use one or more modules (e.g., processing engines) and one or more databases to identify the object each of the tags 102 is associated with, such as a player, official, ball, or the like.

In some embodiments, multiple tags 102 (as well as other sensors) may be attached to the equipment worn by participants. The receiver processing and distribution system 110 may use one or more databases to associate the tag identifier (e.g., a tag UID) of each tag 102 with each player, official, object, or other participant and correlate the tag location data and/or other tag and sensor derived data for multiple tags 102 that are associated with a particular player, official, object, or other participant.

As will be apparent to one of ordinary skill in the art, the inventive concepts herein described are not limited to use with the UWB based RF locating system shown in FIG. 1. Rather, in various embodiments, the inventive concepts herein described may be applied to various other locating systems especially those that are configured to provide robust location resolution (i.e., subfoot location resolution).

Example Tag/Sensor Positioning and Participant Correlation

FIG. 1 shows a monitored area 100. The monitored area 100 comprises a plurality of positions at one or more time epochs. The plurality of positions may be divided into one or more regions, called zones. Each zone may be described by one or more coordinate systems, such as a local NED (North-East-Down) system, a latitude-longitude system, or even a yard line system as might be used for an American football game. A location is a description of a position, or a plurality of positions, within the monitored area. For example, a field marker at the intersection of the south goal line and west out of bounds line at Bank of America Stadium in Charlotte, N.C. could be described as {0,0,0} in a local NED system, or 35.225336 N 80.85273 W longitude 751 ft. altitude on a latitude-longitude system, or simply "Panthers Goal Line" in a yard line system. Because different types of locating systems or different zones within a single locating system may use different coordinate systems, a Geographical Information System or similar monitored area database may be used to associate location data. One type of Geographical Information System describing at least a field of play may be called Field Data.

Figure 2D:
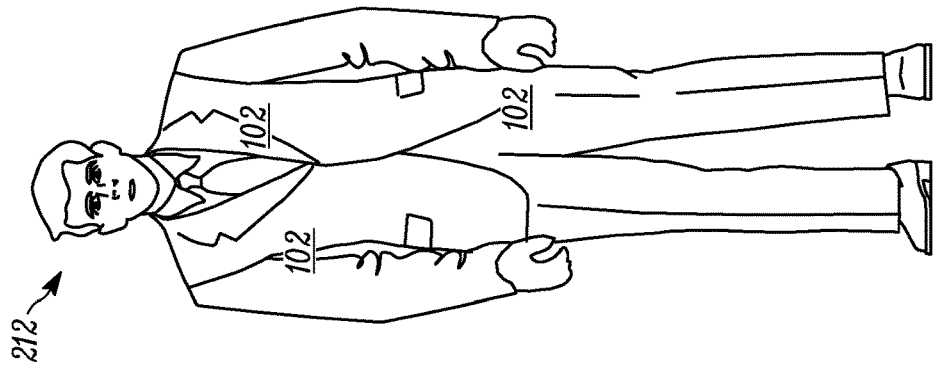
Figure 2C:
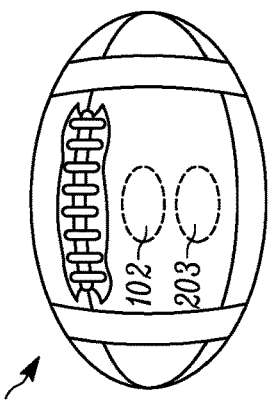
Figure 2B:
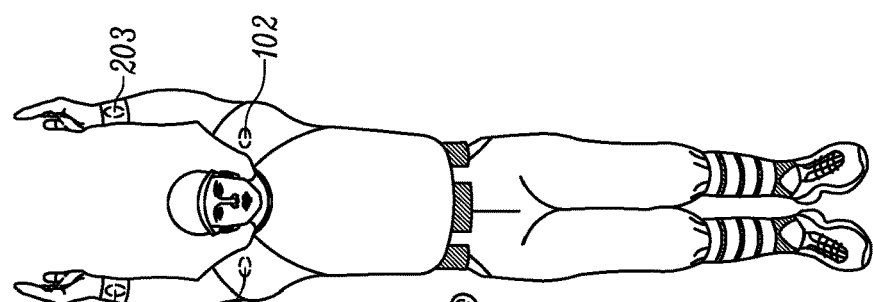
Figure 2A:
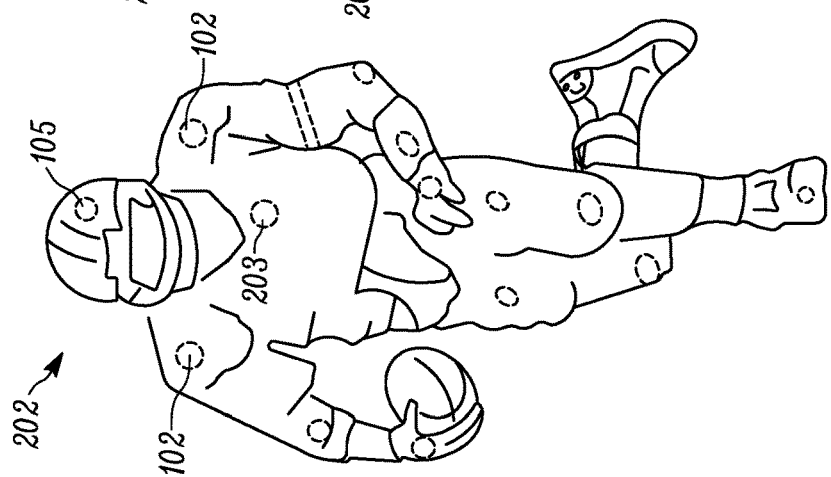

FIGS. 2A-C illustrate some exemplary participants that may provide information to a location system in accordance with some embodiments of the present invention. FIG. 2A illustrates a player 202 (e.g., a football player) wearing equipment having attached tags 102 in accordance with some embodiments. In particular, the depicted player 202 is wearing shoulder pads having tags 102 affixed to opposite sides thereof. This positioning advantageously provides an elevated broadcast position for each tag 102 thereby increasing its communication effectiveness.

Additional sensors 203 may be attached to equipment worn by player 202, such as accelerometers, magnetometers, time-of-flight sensors, health monitoring sensors (e.g., blood pressure sensors, heart monitors, respiration sensors, moisture sensors, temperature sensors), light sensors, or the like. The additional sensors 203 may be affixed to shoulder pads, the helmet, the shoes, rib pads, elbow pads, the jersey, the pants, a bodysuit undergarment, gloves, arm bands, wristbands, and the like.

Sensors 203 may be configured to communicate with receivers (e.g., receivers 106 of FIG. 1) directly or indirectly through tags 102 or other transmitters. For example, in one embodiment, a sensor 203 may be connected, wired (e.g., perhaps through wires sewn into a jersey or bodysuit undergarment) or wirelessly, to tags 102 to provide sensor data to tags 102, which is then transmitted to the receivers 106. In another embodiment, a plurality of sensors (not shown) may be connected to a dedicated antenna or transmitter, perhaps positioned in the helmet, which may transmit sensor data to one or more receivers.

FIG. 2B illustrates a game official 206 wearing equipment having attached tags 102 and sensors 203 in accordance with some embodiments. In the depicted embodiment, tags 102 are attached to the official's jersey proximate opposite shoulders. Sensors 203 are positioned in wristbands worn on the official's wrists as shown. Sensors 203 may be configured to communicate with receivers (e.g., receivers 106 of FIG. 1) directly or indirectly through tags 102 or other transmitters as discussed above in connection with FIG. 2A.

As discussed in greater detail below, the positioning of sensors 203 (here, accelerometers) proximate the wrists of the official may allow the receiver processing and distribution system 110 to determine particular motions, movements, or activities of the official 206 for use in determining event occurrences (e.g., winding of the game clock, first down, touchdown, or the like). The official 206 may also carry other equipment, such as penalty flag 208, which may also have a tag 102 (and optionally one or more sensors) attached to provide additional data to the receiver processing and distribution system 110. For example, the receiver processing and distribution system 110 may use tag location data from the penalty flag 208 to determine when the official is merely carrying the penalty flag 208 versus when the official is using the penalty flag 208 to indicate an event occurrence, such as a penalty (e.g., by throwing the penalty flag 208).

FIG. 2C illustrates an example of a ball 210 having tags 102 attached or embedded in accordance with some embodiments. Additionally, sensors 203 may be attached to or embedded in the ball 210, such as accelerometers, time-of-flight sensors, or the like. In some embodiments, the sensor 203 may be connected, wired or wirelessly, to tag 102 to provide sensor data to tag 102 which is then transmitted to the receivers 106. In some embodiments, the sensor 203 may transmit sensor data to receivers separately from the tag 102, such as described above in connection with FIG. 2A.

FIG. 2D illustrates an example patron 212 carrying one or more tags 102 and/or sensors (not shown) in accordance with some embodiments. The tag 102 and/or sensors may be preferably attached or carried at an elevated position, such as a shirt pocket, a ticket lanyard worn around the neck, or armband. In one embodiment, the tag 102 and/or sensor may be carried near waist level on a belt or in a pants pocket.

As will be apparent to one of ordinary skill in the art in view of this disclosure, once the tags 102 and/or sensors 203 of FIGS. 2A-D are positioned on monitored individuals (i.e., participants and patrons respectively), they may be correlated to such monitored individuals. For example, in some participant focused embodiments, unique tag or sensor identifiers ("unique IDs") may be correlated to a participant profile (e.g., John Smith—running back, Fred Johnson—line judge official, or ID 027—one of several game balls, etc.) and stored to a remote database accessible to the receiver processing and distribution system as discussed in greater detail below. In other embodiments, unique tag or sensor identifiers may be correlated to a patron profile (e.g., Frank Williams—season ticket holder) and stored to a remote database accessible to the receiver processing and distribution system.

Each monitored individual profile, perhaps depending on the type of monitored individual (i.e., participant, patron, venue employee, mobile merchant, etc.), may further include or be correlated with a variety of data including, but not limited to, biometric data (e.g., height, weight, health data, etc.), role data, team ID, performance statistics, employee number, license number, credit card information, employment data, inventory data, and other data that may be apparent to one of skill in the art in view of the foregoing description.

In some embodiments, such monitored individual profile data may be pre-defined and stored in association with the unique tag or sensor identifiers. In other embodiments, the monitored profile data may also be "learned" by the system as a result of received tag or sensor data, formation data, play data, event occurrence data, route data, transaction data, and/or the like. For example, in some embodiments the system may determine that a tag or sensor is not correlated to a monitored individual profile and may analyze data received from the tag and/or sensor to determine possible monitored individual roles, etc., which may be ranked and then selected/confirmed by the system or by a user after being displayed by the system. In some embodiments, the system may determine possible monitored individual roles (i.e., monitored individual role data) based on determined monitored individual location data (e.g., movement patterns, alignment position, etc.).

In some embodiments, as described in greater detail below, the monitored individual profile may also be updated by the system (i.e., to produce a data set for the monitored individual that is far more robust than that established at initial registration) as a result of received tag or sensor data, formation data, play data, event occurrence data, transaction data, and/or the like. In some embodiments, the monitored individual profile data may be used in by the receiver processing and distribution system to weight the actions of the monitored individuals during analysis to assist in qualifying what is occurring, such as in determining formations, plays, event occurrences, transactions, etc.

Tag ID and Sensor Data Transmission Architecture

FIGS. 3A, 3B, 3C, 3D, and 3E show block diagrams of various different architectures that may be utilized in transmitting signals from one or more tags and sensors to one or more receivers of a receiver processing and analytics system in accordance with embodiments of the invention. In some embodiments, the depicted architectures may be used in connection with the receiver processing and distribution system 110 of FIG. 1. As will be apparent to one of ordinary skill in the art in view of this disclosure, more than one of these architectures may be used together in a single system.

Figure 3A:
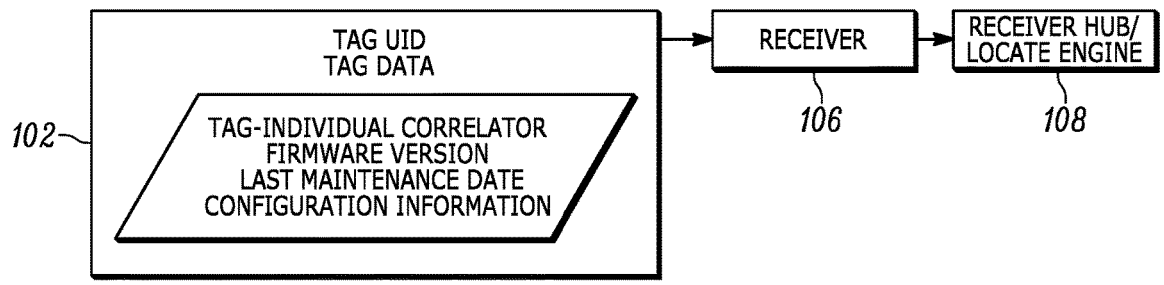
FIGS. 3A-3E are block diagrams showing the input and output of receivers and sensor receivers in accordance with an example embodiment.

FIG. 3A shows a location tag 102, such as that shown in FIG. 1, which may be configured to transmit a tag signal to one or more receivers 106. The one or more receivers 106 may transmit a receiver signal to the central processor/hub 108.

The depicted location tag 102 may generate or store a tag unique identifier ("tag UID") and/or tag data as shown. The tag data may include useful information such as the installed firmware version, last tag maintenance date, configuration information, and/or a tag-individual correlator. The tag-individual correlator may comprise data that indicates that a monitored individual (e.g., participant, a patron, etc.) is associated with the location tag 102 (e.g., name, uniform number and team, biometric data, tag position on individual, i.e., right wrist, patron seat number, season ticket holder number, etc.). As will be apparent to one of skill in the art in view of this disclosure, the tag-individual correlator may be stored to the location tag 102 when the tag is registered or otherwise associated with an individual. While shown as a separate field for illustration purposes, one of ordinary skill in the art may readily appreciate that the tag-individual correlator may be part of any tag data or even omitted from the tag.

The tag signal transmitted from location tag 102 to receiver 106 may include "blink data" as it is transmitted at selected intervals. This "blink rate" may be set by the tag designer or the system designer to meet application requirements. In some embodiments, the blink rate may be consistent for one or all tags. In other embodiments, the blink rate may be data dependent or dynamically changed for load balancing or power management purposes. Blink data includes characteristics of the tag signal that allow the tag signal to be recognized by the receiver 106 so the location of the RF location tag 102 may be determined by the locating system. Blink data may also comprise one or more tag data packets. Such tag data packets may include any data from the tag 102 that is intended for transmission such as, for example, in the depicted embodiment, a tag UID, tag data, and a tag-individual correlator. In the case of TDOA systems, the blink data may be or include a specific pattern, code, or trigger that the receiver 106 (or downstream receiver processing and analytics system) detects to identify that the transmission is from a RF location tag 102 (e.g., a UWB tag).

The depicted receiver 106 receives the tag signal, which includes blink data and tag data packets as discussed above. In one embodiment, the receiver 106 may pass the received tag signal directly to the central processor/hub 108 as part of its receiver signal. In another embodiment, the receiver 106 could perform some basic processing on the received tag signal. For instance, the receiver could extract blink data from the tag signal and transmit the blink data to the central processor/hub 108. The receiver could transmit a time measurement to the central processor/hub 108 such as a TOA measurement and/or a TDOA measurement. The time measurement could be based on a clock time generated or calculated in the receiver, it could be based on a receiver offset value, it could be based on a system time, and/or it could be based on the time difference of arrival between the tag signal of the location tag 102 and the tag signal of a reference tag (e.g., tag 104 of FIG. 1). The receiver 106 could additionally or alternatively determine a signal measurement from the tag signal (such as a received signal strength indication (RSSI), a direction of signal, signal polarity, or signal phase) and transmit the signal measurement to the central processor/hub 108.

Figure 3B:
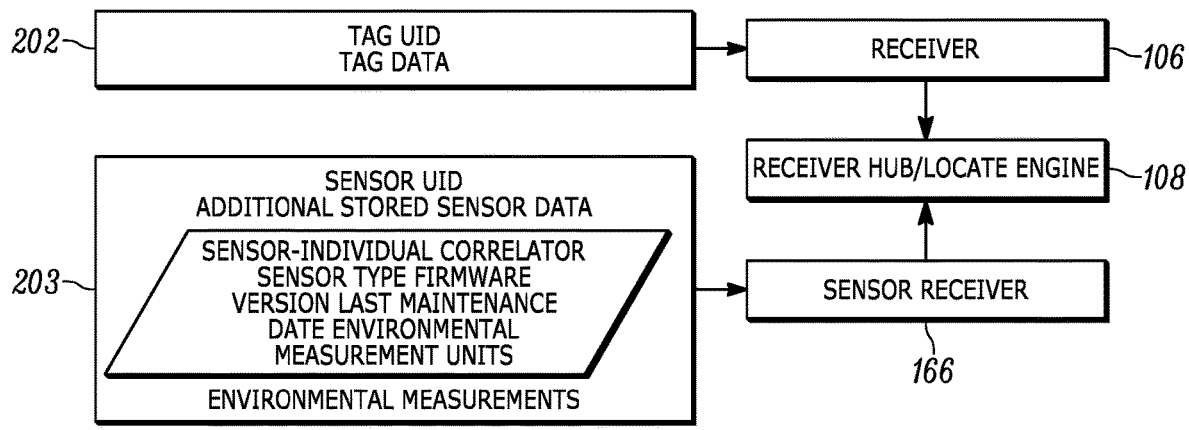

FIG. 3B shows a location tag 202 and sensor 203, such as those worn on an individual's person as shown in FIG. 2, which may be configured to transmit tag signals and sensor signals, respectively, to one or more receivers 106, 166. The one or more receivers 106, 166 may then transmit receiver signals to the central processor/hub 108. One or more receivers 106, 166 may share physical components, such as a housing or antenna.

The depicted location tag 202 may comprise a tag UID and tag data (such as a tag-individual correlator) and transmit a tag signal comprising blink data as discussed in connection with FIG. 3A above. The depicted sensor 203 may generate and/or store a sensor UID, additional stored sensor data (e.g., a sensor-individual correlator, sensor type, sensor firmware version, last maintenance date, the units in which environmental measurements are transmitted, etc.), and environmental measurements. The "additional stored sensor data" of the sensor 203 may include any data that is intended for transmission, including but not limited to a location tag 202, a reference tag (e.g., 104 of FIG. 1), a sensor receiver, a receiver 106, and/or the central processor/hub 108.

The sensor-individual correlator may comprise data that indicates that a monitored individual is associated with the sensor 203 (e.g., name, uniform number and team, biometric data, sensor position on individual, i.e., right wrist, patron seat number, season ticket holder number, etc.). As will be apparent to one of skill in the art in view of this disclosure, the sensor-individual correlator may be stored to the sensor 203 when the sensor is registered or otherwise associated with an individual. While shown as a separate field for illustration purposes, one of ordinary skill in the art may readily appreciate that the sensor-individual correlator may be part of any additional stored sensor data or omitted from the sensor altogether.

Sensors such as sensor 203 that are structured according to embodiments of the invention may sense or determine one or more environmental conditions (e.g., temperature, pressure, pulse, heartbeat, rotation, velocity, acceleration, radiation, position, chemical concentration, voltage) and store or transmit "environmental measurements" that are indicative of such conditions. To clarify, the term "environmental measurements" includes measurements concerning the environment proximate the sensor including, without limitation, ambient information (e.g., temperature, position, humidity, etc.) and information concerning an individual's health, fitness, operation, and/or performance. Environmental measurements may be stored or transmitted in either analog or digital form and may be transmitted as individual measurements, as a set of individual measurements, and/or as summary statistics. For example, temperature in degrees Celsius may be transmitted as {31}, or as {33, 32, 27, 22, 20, 23, 27, 30, 34, 31}, or as {27.9}. In some embodiments, the sensor-individual correlator could be determined at least in part from the environmental measurements.

In the depicted embodiment, location tag 202 transmits a tag signal to receiver 106 and sensor 203 transmits a sensor signal to sensor receiver 166. The sensor signal may comprise one or more sensor information packets. Such sensor information packets may include any data or information from the sensor 203 that is intended for transmission such as, for example in the depicted embodiment, sensor UID, additional stored sensor data, sensor-individual correlator, and environmental measurements. A receiver signal from receiver 106 and a sensor receiver signal from sensor receiver 166 may be transmitted via wired or wireless communication to receiver hub/locate engine 108 as shown.

Figure 3C:
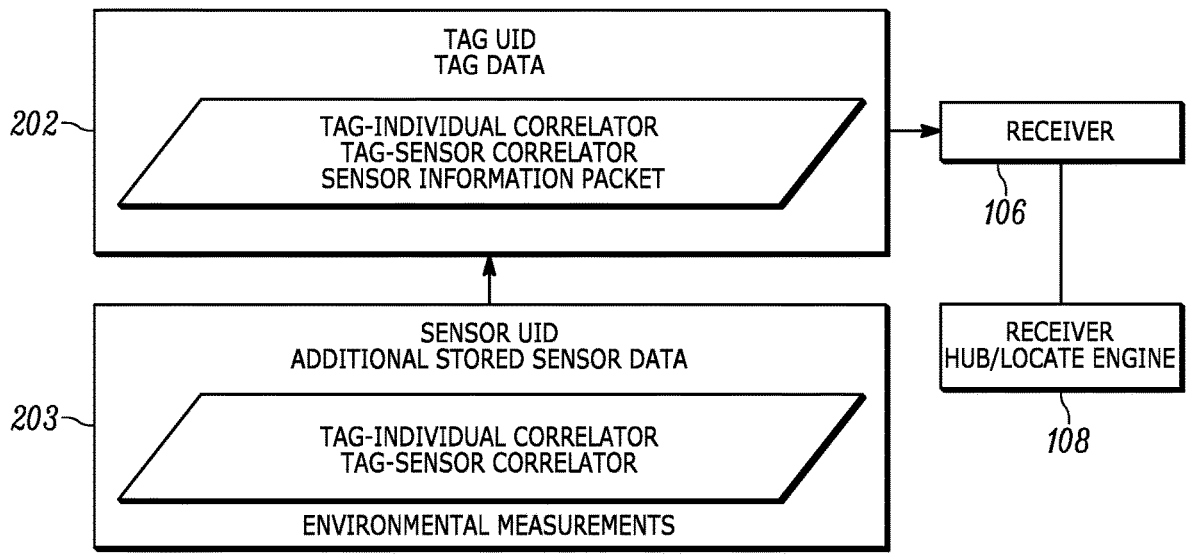

FIG. 3C depicts a sensor 203 communicating through a location tag 202 in accordance with various embodiments. In one embodiment, the sensor 203 may be part of (i.e., reside in the same housing or assembly structure) of the RF location tag 202. In another embodiment, the sensor 203 may be distinct from (i.e., not resident in the same housing or assembly structure) the location tag 202 but configured to communicate wirelessly or via wired communication with the location tag 202.

In one embodiment, the location tag 202, the sensor 203, or both, may generate and/or store a tag-sensor correlator that indicates an association between a RF location tag 202 and a sensor 203 (e.g., tag UID/sensor UID, distance from tag to sensor in a particular stance, set of sensors associated with a set of tags, sensor types associated with a tag, etc.). In the depicted embodiment, both the location tag 202 and the sensor 203 store the tag-sensor correlator.

In the depicted embodiment, sensor 203 transmits a sensor signal to location tag 202. The sensor signal may comprise one or more sensor information packets as discussed above. The sensor information packets may comprise the sensor UID, a sensor-individual correlator, additional stored sensor data, the tag-sensor correlator, and/or the environmental measurements. The location tag 202 may store some portion of, or all of, the sensor information packets locally and may package the sensor information packets into one or more tag data packets for transmission to receiver 106 as part of a tag signal or simply pass them along as part of its tag signal.

Figures 3D, 3E:
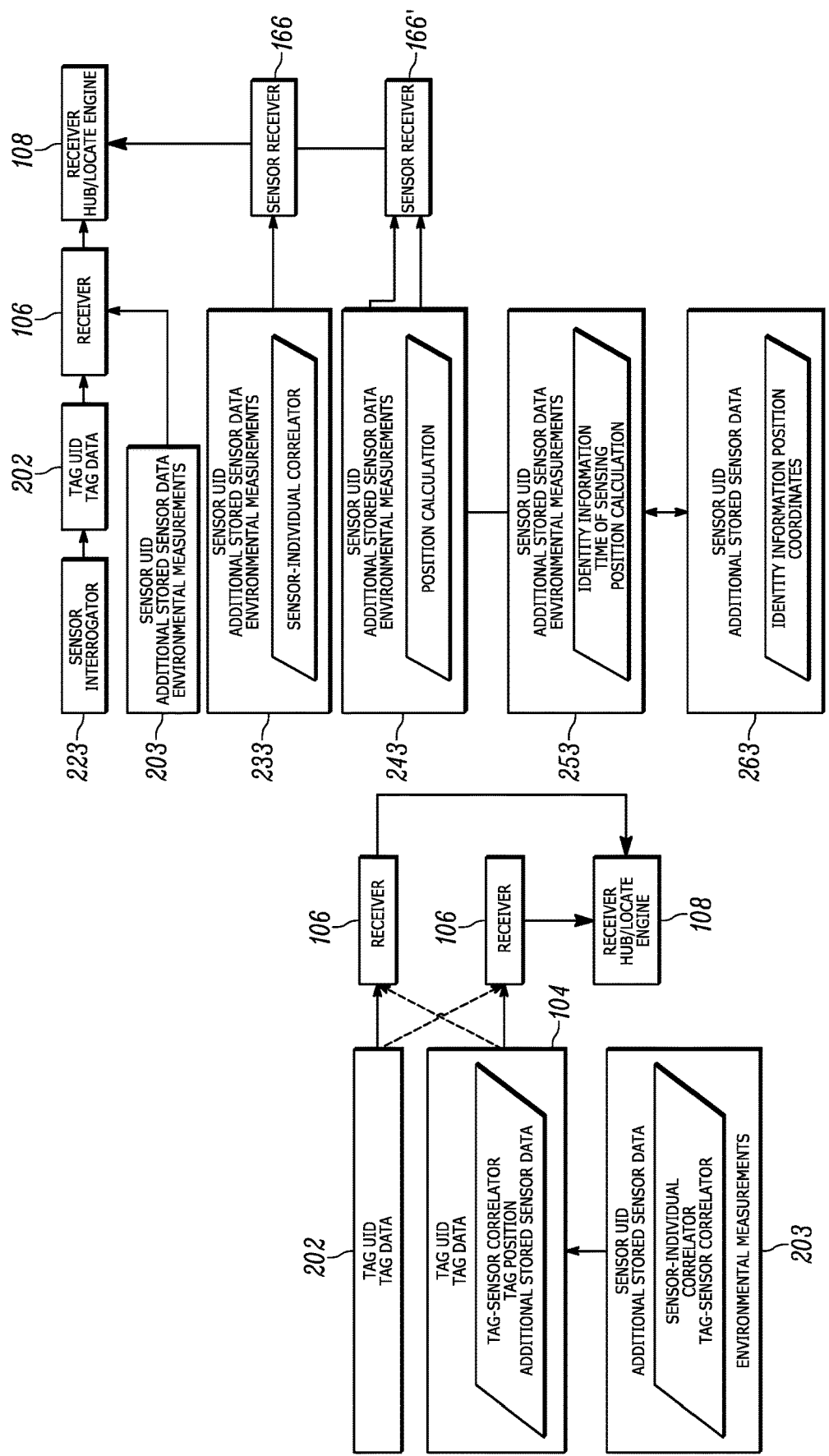

FIG. 3D illustrates an example communication structure for a reference tag 104 (e.g., reference tag 104 of FIG. 1), a location tag 202, a sensor 203, and two receivers 106 in accordance with one embodiment. The depicted reference tag 104 is a location tag and thus may include tag data, a tag UID, and is capable of transmitting tag data packets. In some embodiments, the reference tag 104 may form part of a sensor and may thus be capable of transmitting sensor information packets.

The depicted sensor 203 transmits a sensor signal to reference tag 104. The reference tag 104 may store some portion or some or all of the sensor information packets locally and may package the sensor information packets into one or more tag data packets for transmission to receiver 106 as part of a tag signal, or simply pass them along as part of its tag signal.

As was described above in connection with FIG. 1, the receivers 106 of FIG. 3D are configured to receive tag signals from the location tag 202 and the reference tag 104. Each of these tag signals may include blink data, which may comprise tag UIDs, tag data packets, and/or sensor information packets. The receivers 106 each transmit receiver signals via wired or wireless communication to the central processor/hub 108 as shown.

FIG. 3E illustrates an example communication structure between an RF location tag 202, a plurality of receivers 106, and a variety of sensor types including, without limitation, a sensor 203, a diagnostic device 233, a triangulation positioner 243, a proximity positioner 253, and a proximity label 263 in accordance with various embodiments. In the depicted embodiment, none of the sensors 203, 233, 243, 253 form part of a location tag 202 or reference tag 104. However, each may comprise a sensor UID and additional stored sensor data. Each of the depicted sensors 203, 233, 243, 253 transmits sensor signals comprising sensor information packets.

In the depicted embodiment, receiver 106 is configured to receive a tag signal from location tag 202 and a sensor signal directly from sensor 203. In such embodiments, sensor 203 may be configured to communicate in a communication protocol that is common to location tag 202 as will be apparent to one of ordinary skill in the art in view of this disclosure.

FIG. 3E depicts one type of sensor referred to herein as a "proximity interrogator". The proximity interrogator 223 can include circuitry operative to generate a magnetic, electromagnetic, or other field that is detectable by a location tag 202. While not shown in FIG. 3E, a proximity interrogator 223 may include a sensor UID and other tag and sensor derived data or information as discussed above.

In some embodiments, the proximity interrogator 223 is operative as a proximity communication device that can trigger a location tag 202 (e.g., when the location tag 202 detects the field produced by the proximity interrogator 223) to transmit blink data under an alternate blink pattern or blink rate. The location tag can initiate a preprogrammed (and typically faster) blink rate to allow more location points for tracking an individual. In some embodiments, the location tag may not transmit a tag signal until triggered by the proximity interrogator 223. In some embodiments the RF location tag 202 may be triggered when the location tag 202 moves near (e.g., within communication proximity to) a proximity interrogator 223. In some embodiments, the location tag may be triggered when the proximity interrogator 223 moves near to the location tag 202.

In other embodiments, the location tag 202 may be triggered when a button is pressed or a switch is activated on the proximity interrogator 223 or on the location tag itself. For example, a proximity interrogator 223 could be placed at the start line of a racetrack. Every time a car passes the start line, a car-mounted location tag 202 senses the signal from the proximity interrogator and is triggered to transmit a tag signal indicating that a lap has been completed. As another example, a proximity interrogator 223 could be placed at a sports drink cooler. Each time a player or other participant fills a cup from the cooler a participant-mounted location tag 202 senses the signal from the proximity interrogator and is triggered to transmit a tag signal indicating that sports drink has been consumed. As another example, a proximity interrogator 223 could be placed on a medical cart. When paramedics use the medical cart to pick up a participant (e.g., a player) and move him/her to the locker room, a participant-mounted location tag 202 senses the signal from the proximity interrogator and is triggered to transmit a tag signal indicating that they have been removed from the game. As explained, any of these post-triggered tag signals may differ from pre-triggered tag signals in terms of any aspect of the analog and/or digital attributes of the transmitted tag signal.

FIG. 3E depicts another type of sensor that is generally not worn by an individual but is referred to herein as a "diagnostic device". However, like other sensors, diagnostic devices may measure one or more environmental conditions and store corresponding environmental measurements in analog or digital form.

While the depicted diagnostic device 233 is not worn by an individual, it may generate and store a sensor-individual correlator for association with environmental measurements taken in connection with a specific individual. For example, in one embodiment, the diagnostic device 233 may be a blood pressure meter that is configured to store as environmental measurements blood pressure data for various individuals. Each set of environmental measurements (e.g., blood pressure data) may be stored and associated with a sensor-individual correlator.

The depicted diagnostic device 233 is configured to transmit a sensor signal comprising sensor information packets to a sensor receiver 166. The sensor information packets may comprise one or more of the sensor UID, the additional stored data, the environmental measurements, and/or the sensor-individual correlator as discussed above. The sensor receiver 166 may associate some or all of the data from the sensor information packets with other stored data in the sensor receiver 166 or with data stored or received from other sensors, diagnostic devices, location tags 102, or reference tags. The sensor receiver 166 transmits a sensor receiver signal to a central processor/hub.

Another type of sensor shown in FIG. 3E is a triangulation positioner 243. A "triangulation positioner" is a type of sensor that senses position. The depicted triangulation positioner 243 includes a sensor UID, additional stored sensor data, and environmental measurements as discussed above.

In some embodiments, a triangulation positioner (also known as a global positioning system (GPS) receiver) receives clock data transmitted by one or more geostationary satellites (a satellite in a known or knowable position) and/or one or more ground based transmitters (also in known or knowable positions), compares the received clock data, and computes a "position calculation". The position calculation may be included in one or more sensor information packets as environmental measurements.

In another embodiment, a triangulation positioner comprises one or more cameras or image-analyzers that receive emitted or reflected light or heat, and then analyzes the received images to determine the location of an individual or sensor. Although a triangulation positioner may transmit data wirelessly, it is not a location tag because it does not transmit blink data or a tag signal that can be used by a central processor/hub 108 to calculate location. In contrast, a triangulation positioner senses position and computes a position calculation that may then be used as environmental measurements by the central processor/hub 108.

In one embodiment, a triangulation positioner could be combined with a location tag or reference tag (not shown). In such embodiments, the triangulation positioner could compute and transmit its position calculation via the location tag to one or more receivers. However, the central processor/hub would calculate tag location based on the blink data received as part of the tag signal and not based solely on the position calculation. The position calculation would be considered as environmental measurements and may be included in associated sensor information packets.

As will be apparent to one of ordinary skill in the art, position calculations (e.g., GPS receiver position calculations) are not as accurate as the location calculations (e.g., UWB waveform based location calculations) performed by central processor/hub structured in accordance with various embodiments of the invention. That is not to say that position calculations may not be improved using known techniques. For example, a number of influences, including atmospheric conditions, can cause GPS accuracy to vary over time. One way to control this is to use a differential global positioning system (DGPS) comprising one or a network of stationary triangulation positioners that are placed in a known position, and the coordinates of the known position are stored in memory as additional stored sensor data. These triangulation positioners receive clock data from geostationary satellites, determine a position calculation, and broadcast a difference between the position calculation and the stored coordinates. This DGPS correction signal can be used to correct for these influences and significantly reduce location estimate error.

Another type of sensor shown in FIG. 3E is a proximity detector 253. A "proximity detector" is a type of sensor that senses identity within an area (e.g., a local area) that is small with respect to the monitored area 100 of FIG. 1. Many different ways of sensing identity (e.g., a unique ID or other identifier for a sensed object or individual) would be apparent to one of ordinary skill in the art in view of this disclosure including, without limitation, reading a linear bar code, reading a two-dimensional bar code, reading a near field communication (NFC) tag, reading a RFID tag such as a UHF tag, HF tag, or low frequency tag, an optical character recognition device, a biometric scanner, or a facial recognition system.

In some embodiments, a proximity detector senses an attribute of an individual (or an individual's wristband, tag, label, card, badge, clothing, uniform, costume, phone, ticket, etc.). The identity sensed by a proximity detector may be stored locally at the proximity detector 253 as shown and transmitted as environmental measurements via one or more sensor information packets to a sensor receiver 166.

In some embodiments, a proximity detector 253 may have a defined position, which is often stationary, and may be associated with a location in the monitored area 100 of FIG. 1. For example, a proximity detector 253 could be located at a finish line of a race track, an entrance gate of a stadium, with a diagnostic device, at a goal line or goal post of a football field, at a base or home plate of a baseball diamond, or a similar fixed location. In such embodiments where the proximity detector is stationary, the position coordinates of the proximity detector and a sensor UID could be stored to a monitored area database (not shown) that is accessible by one or more of the receivers 106, 166, the receiver hub/locate engine 108, and/or other components of the receiver processing and analytics system 110. In embodiments where the proximity detector is movable, a position calculation could be determined with a triangulation positioner, or the proximity detector could be combined with a location tag and located by the central processor/hub 108. While shown as separate fields for illustration purposes in FIG. 3E, identify information and position calculation could comprise part of the additional stored sensor data, the environmental measurements, or both.

In one embodiment, the proximity detector could be associated with a reference tag (e.g., tag 104 of FIG. 1) whose position is recorded in the monitored area database. In other embodiments, the proximity detector is movable, such that it may be transported to where it is needed. For example, a proximity detector 253 could be located on a medical cart, first down marker, a diagnostic device, goal post, or carried by a paramedic or security guard. In an embodiment where the proximity detector 253 is movable it would typically be associated with a location tag or triangulation positioner so that location (for a location tag) or position (for a triangulation positioner) can be determined at the time identity is sensed.

In the embodiment where the proximity detector includes a location tag, the central processor/hub 108 would locate the associated location tag, and the tag data/sensor data filter 112 would associate the tag location data for the associated location tag as the position of the proximity detector, while determining the identity of an associated individual from any received sensor information packets. In the alternate embodiment where the proximity detector includes a triangulation positioner, the triangulation positioner would compute a position calculation that could be stored as additional stored sensor data and/or environmental measurements, and transmitted as one or more sensor information packets. In one embodiment, sensor information packets for a proximity detector may include both sensed identity information and a position calculation.

Another type of sensor shown in FIG. 3E is a proximity label 263. A proximity label has a fixed position and an identification code (e.g., a sensor UID). The proximity label 263 may further comprise additional stored sensor data as shown. The depicted proximity label 263 is configured to be read by proximity detector 253. In some embodiments, proximity detector 253 may be further configured to write information to proximity label 263.

A proximity label 263 may be a sticker, card, tag, passive RFID tag, active RFID tag, NFC tag, ticket, metal plate, electronic display, electronic paper, inked surface, sundial, or otherwise visible or machine readable identification device as is known in the art. The coordinates of the position of the proximity label 263 are stored such that they are accessible to the central processor/hub 108. For example, in one embodiment, the position coordinates of a proximity label 263 could be stored in a field database or monitored area database accessible via a network, or stored locally as additional stored data in the proximity detector 253.

In some embodiments, a position of the proximity label 263 is encoded into the proximity label 263 itself. For example, coordinates of a position of the proximity label 263 could be encoded into a passive RFID tag that is placed in that position. As another example, the coordinates of a position of the proximity label 263 could be encoded into a printed barcode that is placed in that position. As another example, a proximity label 263 comprising a NFC tag could be encoded with the location "end zone", and the NFC tag could be placed at or near an end zone at Bank of America stadium. In some embodiments, the stored coordinates of the proximity label 263 may be offset from the actual coordinates of the proximity label 263 by a known or determinable amount.

In one embodiment, a proximity label 263 such as an NFC tag may be encoded with a position. When a sensor such as a proximity detector approaches the NFC tag it may read the position, then transmit the position in a sensor information packet to the sensor receiver 166' and eventually to the central processor/hub 108. In another embodiment, a proximity label 263 such as a barcode label may be encoded with an identification code. When a smartphone with a proximity detector (such as a barcode imager) and a triangulation positioner (such as a GPS chip, GPS application, or similar device) approaches the barcode label it may read the identification code from the barcode, determine a position calculation from received clock data, then transmit the identity and the position calculation to sensor receiver 166' and eventually to the receiver hub/locate engine 106 as part of one or more sensor information packets.

In the depicted embodiment, triangulation positioner 243 and proximity detector 253 are each configured to transmit sensor signals carrying sensor information packets to sensor receiver 166'. The depicted sensors 243, 253, like any sensor discussed herein, may transmit sensor signals via wired or wireless communication protocols. For example, any proprietary or standard wireless protocol (e.g., 802.11, Zigbee, ISO/IEC 802.15.4, ISO/IEC 18000, IrDA, Bluetooth, CDMA, or any other protocol) could be used for the sensor signals. Alternatively or additionally, any standard or proprietary wired communication protocol (e.g., Ethernet, Parallel, Serial, RS-232, RS-422, USB, Firewire, $I^2C$, etc.) may be used. Similarly, sensor receiver 166', and any receiver discussed herein, may use similar wired and wireless protocols to transmit receiver signals to the central processor/hub.

In one embodiment, upon receiving sensor signals from the triangulation positioner 243 and the proximity detector 253, the sensor receiver 166' may associate some or all of the data from the received sensor information packets with other data stored to the sensor receiver 166', or with data stored or received from other sensors (e.g., sensor 203), diagnostic devices 233, location tags 102, or reference tags 104. Such associated data is referred to herein as "associated sensor data". In the depicted embodiment, the sensor receiver 166' is configured to transmit some or all of the received sensor information packets and any associated sensor data to the central processor/hub 108 at part of a sensor receiver signal.

In one embodiment, a smartphone comprising a proximity detector (such as a barcode imager) and a triangulation positioner (such as a GPS chip) may associate an identification code determined from a barcode with a position calculation from received clock data as associated sensor data and transmit a sensor information packet that includes such associated sensor data to the central processor/hub 108. In another embodiment, the smartphone could transmit a first sensor information packet including the identification code and the smartphone's unique identifier to another sensor receiver, the smartphone could transmit a second sensor information packet including the position calculation and the smartphone's unique identifier to the sensor receiver, and the sensor receiver could associate the position calculation with the identification code based on the common smartphone unique identifier and transmit such associated sensor data to the central processor/hub 108. In another embodiment, the sensor receiver could determine a first time measurement associated with the first sensor information packet and a second time measurement associated with the second sensor information packet that, in conjunction with the sensor UID, could be used, by the central processor/hub 108, to associate the first sensor information packet with the second sensor information packet.

In one embodiment, the central processor/hub 108 receives receiver signals from the receiver 106 and sensor receiver signals from the sensor receivers 166, 166'. In the depicted embodiment, receiver 106 may receive blink data from the location tag 102 and transmits to the central processor/hub 108 some or all of the blink data, perhaps with additional time measurements or signal measurements. In some embodiments, time measurements or signal measurements may be based on a tag signal received from a reference tag (e.g., reference tag 104 of FIG. 1). The central processor/hub 108 collects the blink data, time measurements (e.g. time of arrival, time difference of arrival, phase), and/or signal measurements (e.g. signal strength, signal direction, signal polarization, signal phase) from the receivers 106 and computes tag location data for the tags 102 as discussed above in connection with FIG. 1. In some embodiments, the receivers 106 may be configured with appropriate RF filters, such as to filter out potentially interfering signals or reflections proximate the field of play or other area to be monitored.

The central processor/hub 108 may also access stored data or clock data from local storage and from a network location. The central processor/hub 108 uses this information to determine tag location data for each RF location tag. It may also associate data derived or extracted from tag signals transmitted from one or more RF location tags with information or data derived or extracted from sensor signals transmitted from one or more sensors.

In addition to the TOA or TDOA systems previously described, other real-time location systems (RTLS) such as received signal strength indication based systems could potentially be implemented by a receiver hub/locate engine 108. Any RTLS system using location tags, including those described herein, could require considerable processing by the central processor/hub 108 to determine the tag location data from the blink data received from the tags. These may require time measurement and/or signal measurement in addition to blink data, which preferably includes a tag UID. In contrast, in other systems, such as global position systems (GPS) systems, location data is determined based upon the position calculation transmitted from a GPS transmitter (also referred to as a GPS receiver or GPS tag) which includes calculated information about the location where the tag was positioned (i.e., coordinates determined at the tag via satellite signal triangulation, etc.) when the position calculation was determined or stored. Thus, GPS information typically refers to additional information that is transmitted along with a GPS transmitter ID before the transmission is received by a sensor receiver.

A GPS host device or back-end server may receive the GPS information and simply parse the position calculation (as opposed to calculating the position information at the host device) and the GPS transmitter ID into a data record. This data record may be used as a GPS position calculation, or it could be converted to a different coordinate system to be used as a GPS position calculation, or it could be processed further with DGPS information to be used as a GPS position calculation.

Returning to FIG. 3C, the depicted location tag 202 is used to convey (sometimes called backhaul) sensor information packets to a receiver 106. In some embodiments, while not shown, multiple sensors 203 may transmit sensor signals carrying sensor information packets to location tag 202. Such received sensor information packets may be associated with blink data that is transmitted to receiver 106.

In one embodiment, the central processor/hub 108 may parse sensor information packets from received tag data packets and associate such sensor information packets with the location tag 202 that transmitted the sensor information packet. Thus, the central processor/hub 108 may be able to determine tag location data, which may comprise a location and other data (e.g., tag data, tag UID, tag-individual correlator, sensor-individual correlator, additional stored sensor data, environmental measurements, tag-sensor correlator, identity information, position calculation, etc.) from one or more tags or sensors. Such data and information may be transmitted to the receiver processing and analytics system 110.

In some embodiments, once the central processor/hub 108 determines a location estimate of a location tag 102 at the time epoch of the tag signal, the central processor/hub 108 can also associate a location estimate with the tag data packet included in the blink data of such tag signal. In some embodiments, the location estimate of the tag signal may be used as tag location data for the tag data packet. In some embodiments a Geographical Information System (GIS) may be used by the central processor/hub 108 to refine a location estimate, or to map a location estimate in one coordinate system to a location estimate in a different coordinate system, to provide a location estimate for the tag data packet.

In one embodiment, the location estimated for the tag data packet may be associated with any data in the tag data packet, including a tag UID, other tag data, and, if included, one or more sensor information packets, including sensor UID, additional stored sensor data, and environmental measurements. Since environmental measurements may include a position calculation from a triangulation positioner (e.g., a GPS device), the central processor/hub 108 could parse the position calculation and use it to refine a location estimate for the tag data packet.

Preferably, the central processor/hub 108 may access an individual database to determine tag-individual correlators or sensor-individual correlators. Individual data (e.g., an individual profile) may be stored in a server, in tag memory, in sensor memory, or in other storage accessible via a network or communication system, including tag data or additional stored sensor data as explained previously.

In some embodiments, by comparing data accessed using a sensor-individual correlator, the central processor/hub 108 may associate an individual with a sensor information packet received from a sensor, and/or may associate an individual with such sensor. Because the central processor/hub 108 may associate a sensor position estimate with a sensor information packet, the receiver hub/locate engine 108 may also estimate an individual position for the associated individual.

In another embodiment, by comparing data accessed using a tag-sensor correlator, the central processor/hub 108 may associate a sensor with a tag data packet received from a location tag 102. Because the central processor/hub 108 may associate a location estimate with a tag data packet, the central processor/hub 108 may also create a sensor location estimate for the associated sensor. By comparing a location estimate for a location tag with a sensor location estimate or a sensor position estimate, the central processor/hub 108 may associate a location tag with a sensor, or may associate a tag data packet with a sensor information packet. The central processor/hub 108 could also determine a new or refined tag-sensor correlator based on this association.

In still another embodiment, by comparing a location estimate for a location tag with an individual location estimate or an individual position estimate, central processor/hub 108 may associate a location tag with an individual, or may associate a tag data packet with an individual. The central processor/hub 108 could also determine a new or refined tag-individual correlator based on this association.

In one embodiment, by comparing a location estimate for a sensor with an individual location estimate or an individual position estimate, the central processor/hub 108 may associate a sensor with an individual, or may associate a sensor information packet with an individual. The central processor/hub 108 could also determine a new or refined sensor-individual correlator based on this association.

Data derived or extracted from tag signals transmitted from one or more RF location tags is referred to herein as "tag derived data" and shall include, without limitation, tag data, tag UID, tag-individual correlator, tag-sensor correlator, tag data packets, blink data, time measurements (e.g. time of arrival, time difference of arrival, phase), signal measurements (e.g., signal strength, signal direction, signal polarization, signal phase) and tag location data (e.g., including tag location estimates). Tag derived data is not derived by the RF location tag, but rather, is derived from information transmitted by the RF location tag. Information or data derived or extracted from sensor signals transmitted from one or more sensors is referred to herein as "sensor derived data" and shall include, without limitation, sensor UID, additional stored sensor data, sensor-individual correlator, environmental measurements, sensor information packets, position calculations (including sensor position estimates), position information, identity information, tag-sensor correlator, and associated sensor data.

Data derived or extracted from stored individual data is referred to herein as "individual profile information", "participant profile information", "patron profile information" or simply "profile information" and shall include, without limitation tag-individual correlator, sensor-individual correlator, identity information, name, uniform number and team, biometric data, tag position on individual, patron seat number, payment information, season ticket holder number, and other similar information. In various embodiments, the receiver hub/locate engine 108 may transmit tag derived data, sensor derived data, individual profile information, various combinations thereof, and/or any information from the GIS, the field database, the monitored area database, and the individual database to the receiver processing and analytics system 110.

Example Receiver Hub and Receiver Processing and Distribution System

Figure 4:
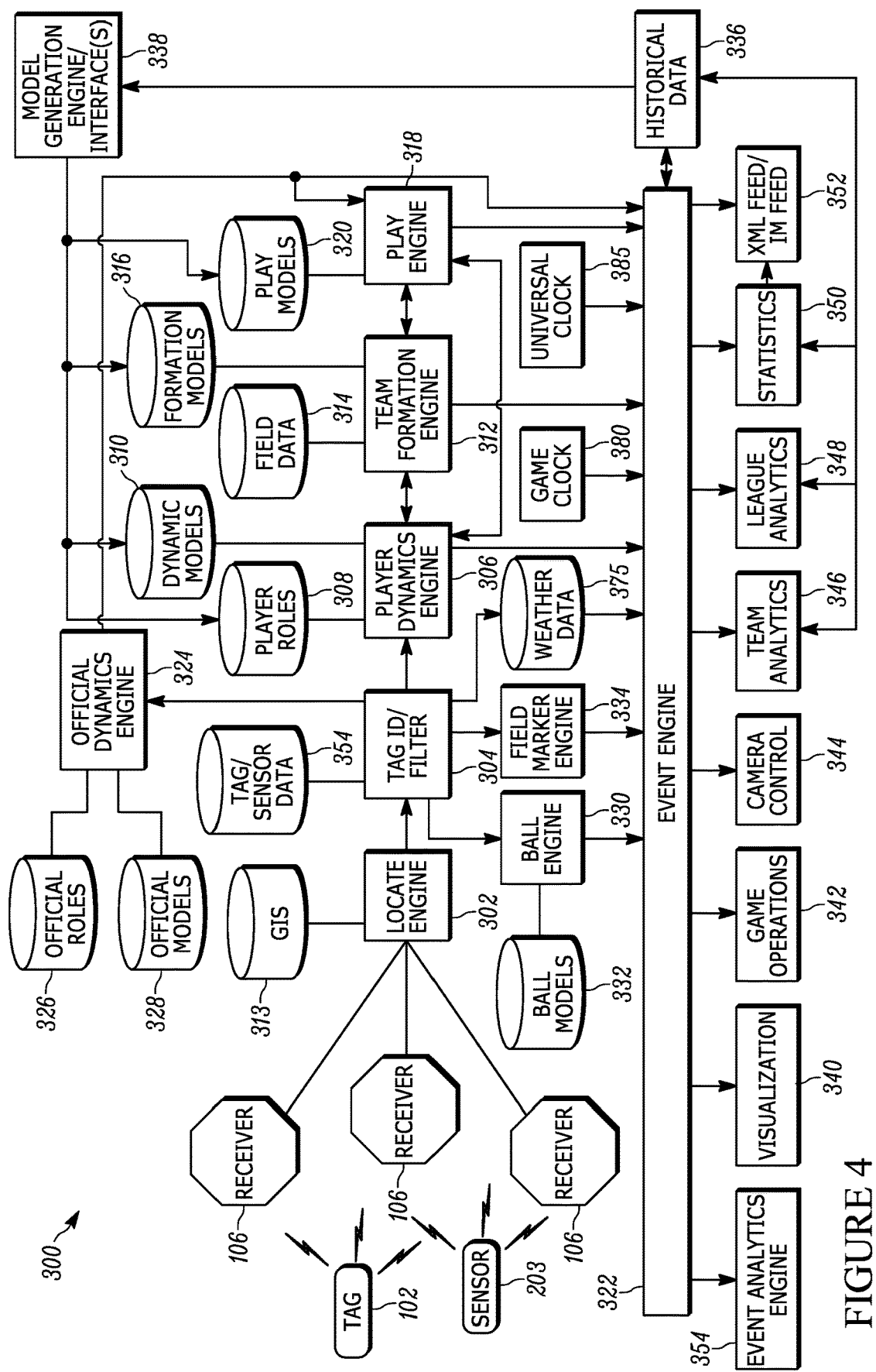
FIG. 4 illustrates an exemplary system for providing performance analytics in accordance with some embodiments of the present invention.

FIG. 4 illustrates an exemplary system 300 for providing performance analytics in accordance with some embodiments of the present invention. The depicted performance analytics system 300 may be distributed in a central processor/hub' 108 and a receiver processing and distribution system 110 of the type depicted in FIG. 1. For example, locate engine 302 may be part of the central processor/hub 108 with the tag ID/Filter 304 through event engine 322 forming part of the receiver processing and distribution system 110. In alternative embodiments, the performance analytics system 300 may be housed or located in a single housing or unit. In still other embodiments, the performance analytics system 300 may be distributed among multiple additional housings or units depending upon the application and other design parameters that will be apparent to one of ordinary skill in the art in view of this disclosure.

The performance analytics system 300 of FIG. 4 may include a plurality of tags 102, and optional sensors 203, associated with participants (e.g., players, officials, balls, field markers, etc.), a plurality of receivers 106 positioned within a monitored environment, a receiver hub/locate engine 302, one or more filters 304, a plurality of databases, a plurality of processing engines, and a plurality of output systems. While only one type of receiver 106, other types of receivers, e.g., sensor receivers 166, 166' of FIG. 3E, may be used in accordance with the embodiments illustrated by FIG. 4. The one or more databases may include databases for tag identifiers 354, player roles 308, player dynamics or kinetics models 310, GIS data or a GIS database 313, field data or a field knowledge database 314, formation models 316, play models 320, official roles 326, official models 328, ball models 332, weather data 375, and the like. The plurality of processing engines may include a player dynamics engine 306, a team formation engine 312, a play engine 318, an event engine 322, an official dynamics engine 324, a field marker engine 334, a ball engine 330, and a model generation engine 338, or the like. The system 300 may further include a game clock 380 and a universal clock 385.

In an exemplary performance analytics system 300, such as illustrated in FIG. 4, the plurality of tags 102 (and sensors 203) may be attached to a participant as discussed in connection with FIGS. 2A-C. In some embodiments, the plurality of tags 102 and/or sensors 203 may be activated and deactivated as needed, such as before and after a game or when damaged or to replace batteries, power suppliers, local memory, etc. Each of the tags 102 may transmit a tag signal, which may include tag derived data, which is received by one or more of the receivers 106. In some embodiments, the receivers 106 may be configured with appropriate RF filters, such as to filter out potentially interfering signals or reflections proximate the field of play or other environment to be monitored.

Each of the receivers 106 may receive tag derived data from the tags 102 and transmit the tag derived data to the receiver hub/locate engine 302. The receiver hub/locate engine 302 collects the tag derived data from the receivers 106 and computes tag location data (based on the blink data) for the tags 102 as discussed above in connection with FIG. 1.

In the depicted embodiment, each of the receivers 106 receives sensor derived data from sensor signals transmitted by sensors 203. In other embodiments, sensor receivers (e.g., sensor receivers 166, 166' of FIG. 3E) may transmit sensor signals comprising sensor derived data to the receiver hub/locate engine 302.

The tag location data, tag derived data, and sensor derived data may be provided from the receiver hub/locate engine 302 to a tag ID/filter 304 that determines the type of participant associated with each received unique tag ID (and/or sensor ID) and routes the associated tag derived data (and optionally, other received tag/sensor derived data) to one or more engines associated with such participant type (e.g., player, ball, official, field marker, etc.). In one embodiment, the tag ID/filter 304 performs this routing, at least in part, by correlating the received unique tag ID (and/or sensor ID) to profile data or prior correlations (i.e., tag ID No. 0047 is correlated to participant John Smith—quarterback, sensor ID No. 12459 is correlated to Marcus Henderson—official, etc.) that may be stored to a tag/sensor identification database 354 (i.e., tag-individual correlators, sensor-individual correlators, tag-sensor correlators, etc.). In some embodiments, the receivers 106 may also receive sensor derived data for other sensors 203, such as through the tags 102 or through separate transmission means.

In one embodiment, perhaps in connection with the player illustration of FIG. 2A, the tag ID/filter 304 identifies tag location data associated with a player and thus routes such data to a player dynamics engine 306 for further processing. The player dynamics engine 306 is disposed in communication with a player role database 308, which comprises player role data correlating tag and sensor UIDs to player profiles (e.g., individual profile information) including, without limitation, which roles (e.g., quarterback, running back, flanker, slot receiver, tight end, left tackle, left guard, center, right guard, right tackle, defensive end, defensive tackle, nose tackle, inside linebacker, outside linebacker, free safety, strong safety, cornerback kicker, punter, etc.) the players perform during a game.

The player dynamics engine 306 may also be disposed in communication with a dynamics/kinetics model database 310. The player dynamics engine 306 may compare the tag location data, other tag and sensor derived data, and player role data to player dynamics/kinetics models to determine aspects of the player dynamics or movement kinetics. The dynamics/kinetics model database 310 may comprise models of different aspects or dimensions that may be based on past player location data or other data generated by the model generation engine 338 as discussed below. The models may include, without limitation, models for a particular player profile (e.g., John Smith), a player type (e.g., quarterback), a player type for a particular team (e.g., a quarterback from the Chicago Wizards), a player type for a particular formation (e.g., a quarterback in a spread offense), and the like. Such models may consider all three dimensions (x, y, z) of the tag location data for each tag (e.g., 102 of FIG. 2A) and may further consider different tag position arrays (e.g., two tag implementations—one proximate each shoulder as in FIG. 2A, eleven tag implementations—one proximate each shoulder, one proximate each elbow, one proximate each hand, one proximate each knee, one proximate each foot, and one proximate the head).

In one embodiment, the player dynamics engine 306 determines a multi-dimensional player location per unit time (e.g., participant location data) for each player based on the tag location data, other tag and sensor derived data, the player role data, and the player dynamics/kinetics models. Such multi-dimensional player location may include relative location of the player relative to the field of play, and/or general orientation of the player (e.g., standing, squatting, laying the ground, sitting, etc.) such as by correlating location data and other tag and sensor derived data.

The player dynamics engine 306 uses the real time tag location data stream from the locate engine 302, as well as the player role database 308 to provide accurate information about what a particular player is doing in real time (or near real time). The player dynamics engine 306 may further use other tag and sensor derived data, received from the locate engine 302 in the depicted embodiment, to aid in determining not only where the player is, but also how that player's location is changing with time, velocity, acceleration, deceleration, orientation, or the like. The player dynamics engine 306 outputs multi-dimensional player location information per unit time (e.g., participant location data).

In one embodiment, sensor derived data may comprise accelerometer data that may indicate that a player (or portion of a player) is accelerating or decelerating. In addition to the variety of other uses that will be apparent to one of ordinary skill in the art in view of this disclosure, the accelerometer data may be used to improve location accuracy for the system. For example, in circumstances where the real time tag location data stream erroneously suggests (perhaps due to interference, multipath effects, signal reflections, signal losses due to line-of-sight blockages, etc.) that one of the possible locations for the player is 10 feet away from a prior location, the accelerometer data could be used to confirm that the player (or accelerometer affixed portion of the player) did not experience an acceleration sufficient to move that distance in the amount of time provided.

In some embodiments, sensor derived data may comprise time-of-flight sensor data, which may indicate distances between participants (e.g., distance of a player to other players, officials, the ball, etc.) or other objects. In applications involving complex tagged object movements such as, the example football application discussed herein, time-of-flight sensor data may be used to enhance the location accuracy of the system especially in circumstances where one or more tags or sensors are temporally unable to effectively transmit their data to one or more receivers. For example, in one embodiment, a tag positioned within the ball may appear to the system as not moving because the running back carrying the ball has run into a group of other players and the bodies of such other players are actually blocking the line-of-sight transmissions of the ball tag. In this embodiment, time-of-flight sensors positioned on the group of other players may be repeatedly determining and transmitting to one or more receivers the relative distance between such time-of-flight sensors and the ball or ball carrier. In this regard, the system may determine that the ball is no longer at the ten yard line (i.e., the point where the system last received a transmission directly from the ball tag) but rather has advanced toward the opponent's end zone to the six yard line. This and other similar techniques may be used alone or in combination with other tag and sensor derived data (e.g., accelerometer data, etc.) to create a type of mesh network that may adapt to temporary or sustained line-of-sight blockages and improve the accuracy of location determinations, formation determinations, play determinations, etc.

In some embodiments, the player dynamics engine 306 outputs multi-dimensional player location information per unit time to an event engine 322. In some embodiments, the multi-dimensional player location information may include a ranked or weighted list of probable player locations while, in other embodiments, the multi-dimensional player location information includes only a top, or most probable, player location. This information may be used by the event engine 322 to determine a number of important player events. For example, the multi-dimensional player location information may be used to indicate that a player was tackled (i.e., experienced a rapid deceleration and transited from a standing to a laying position) and is subsequently limping (e.g., tag and/or sensor data from tags/sensors proximate the players feet indicate a change in the gait of the player). In such example, the event engine 322 may be configured to transmit an alert (e.g., via text message, email, or the like) to an athletic trainer to have the player checked-out or treated.

The player dynamics engine 306 may further output the multi-dimensional player location information per unit time (e.g., participant location data) to a team formation engine 312. The team formation engine 312 is disposed in communication with a formation models database 316 that contains models of various formations (e.g., offensive formations, defensive formations, special teams formations, etc.) defined for the relevant sport or activity (e.g., football in the depicted embodiment). The models of various formations may be derived from multi-dimensional player location information collected during prior games, practices, etc., (e.g., learned by the system) or as input by one or more teams, such as by using model generation engine 338, historical data store 336, and/or team analytics engine 346.

The team formation engine 312 is further disposed in communication with a field data database 314 to assist in determining the likely team formations. The field data database 314 may comprise, without limitation, survey data for the field (e.g., various distances or coordinates from reference tag(s) or other marker to yard lines, end zones, goal posts, boundaries, benches, locker rooms, spectator areas, other zones of interest, etc.).

In one embodiment, the team formation engine 312 determines one or more formations (e.g., a probable formation or a ranked or weighted list of probable formations) based at least in part on the field data, the multi-dimensional player location information (which may include the tag derived data and/or sensor derived data), and the formation models. The team formation engine 312 may hypothesize the received multi-dimensional player location data against models of every known formation to determine a probable formation or a ranked or weighted list of probable formations. The team formation engine 312 is thus configured to determine and output a data stream of formations versus time, which considers how various formations change and may be used by downstream engines to determine various events including the occurrence of a play.

In one embodiment, the team formation engine 312 may assign weights to the received multi-dimensional player location data (i.e., participant location data), other types of tag derived data and/or sensor derived data, and/or to the formation models when determining a specific formation or ranked list of probable formations. For example, in one embodiment, the team formation engine 312 may be configured to assign a greater weight to the position of the ball (which should remain stationary for a period of time as formations are being established, i.e., at the beginning of a play) than to the position of an official (which may move to some degree as formations are forming). In another embodiment, the team formation engine 312 may be configured to assign a greater weight to the location of the tight-end (which may indicate the strong side of a formation) than to the location of a left guard (whose location seldom effects formation determination). In still another embodiment, the team formation engine 312 may be configured to assign a greater weight to sensor derived data associated with an accelerometer positioned proximate an official's wrist (which may indicate winding of the play clock that often triggers the period during which formations ought to be forming) than to the location of any player.

In one embodiment, the team formation engine 312 outputs the data stream of formations versus time (e.g., formation data) to the play engine 318. The play engine 318 may also receive the output data stream (e.g., multi-dimensional player location information versus time) from the player dynamics engine 306. The play engine 318 is disposed in communication with a play models database 320. The play models database 320 may include play models (e.g., known formation shifts or movements over time). Such play models may be programmatically learned by the system (e.g., based on actual movements of players tracked by the system) or manually entered through an interface or other tool (e.g., perhaps through the model generation engine 338). In this regard, the play models database 320 may include historical plays executed by teams, potential/future plays from a team game plan or playbook, or other historical data (e.g., from historical data store 336).

In one embodiment, the play engine 318 may take the formations versus time data stream from the formation engine 312, the play models, and the player dynamics data stream (which may include tag location data and/or other tag and sensor derived data) to determine whether a play is forming, a play has started, a play is in progress, or a play has ended. For example, the play engine 318 may determine that it is most likely that a pre-snap formation at the line of scrimmage has occurred (e.g., an offensive team has aligned in a "pro set" formation and a defensive team has aligned in a "3-4" formation) indicating a play is about to begin. The play engine 318 may thereafter determine that the offensive and defensive players have begun rapidly accelerating towards and across a line of scrimmage thereby indicating that a play has begun. The play engine may further determine that an offensive player has been tackled by a defensive player thereby indicating that a play has concluded.

In some embodiments, the play engine 318 may use assigned weights (or assign weights) to the received data (e.g., the tag derived data, the sensor derived data, the multi-dimensional player location data, the formations data, officials data, etc.) for use in analyzing the data and determining the most probable play events. For example, the play engine 318 may determine that data for particular participants (e.g., a left guard) has a lower relevance for a particular formation (e.g., a pro set offensive formation) and assign a lower weight to that data during the analysis than to another participant (e.g., the ball, the quarterback, a wide receiver, etc.).

In some embodiments, the play engine 318 is disposed in communication with an official dynamics engine 324 to further improve the play determination accuracy of the system. The official dynamics engine 324 may provide data about the movements, actions, positions of an official, which the play engine 318 may use when determining a probable play and/or the status of a play. For example, as discussed in connection with FIG. 2B above, an official may be provided with wrist based accelerometers or other sensors (e.g., a whistle sensor), which may be used to flag the beginning or ending of a given play based on the movement or action of an official (e.g., rotating an arm to wind the play clock, indicate touchdown with two arms raised, blow a whistle, etc.).

The play engine 318 may analyze how the team formations occur and how they break up to determine both start and stop of a play (e.g., start of play event, end of play event, etc.). For example, the play engine 318 may determine that offensive and defensive formations coalesced proximate a line of scrimmage and then broke up with various receivers heading towards the defensive team's end zone, there was all kinds of activity around a quarterback which eventually dissipated, and that defense players were tracking one of the receivers downfield until the receiver crossed into the end zone and an official raised his arms. The play engine 318 may determine that this participant activity best fits a play model whereby a ball was thrown and caught by a receiver who then scored a touchdown thereby ending the play.

In some embodiments, the play engine 318 may hypothesize the received multi-dimensional player location data (e.g., participant location data) and the data stream of formations versus time against models of every known play to determine a probable play or a ranked list of probable plays. The play engine 318 is thus configured to determine and output a data stream of plays versus time, which may be communicated to the event engine 322.

In some embodiments, the tag ID/filter 304 may determine that received tag derived data and/or sensor derived data corresponds to one or more officials. Such official correlated tag/sensor derived data is routed to the official dynamics engine 324. The official dynamics engine 324 is disposed in communication with an official roles database 326, which comprises official roles data correlating tag and sensor IDs (or other tag/sensor individual correlators) to official profiles including, without limitation, which roles (e.g., referee, umpire, head linesman, line judge, back judge, field judge, side judge, etc.) the officials perform during a game.

The official dynamics engine 324 may also be disposed in communication with a dynamics/kinetics model database 328. The official dynamics engine 324 may compare the tag location data, other tag/sensor derived data, and official role data to official dynamics/kinetics models to determine aspects of the official dynamics or movement kinetics. The dynamics/kinetics model database 328 may comprise models of different aspects or dimensions that may be based on past official location data or other data generated by the model generation engine 338 as discussed below. The models may include, without limitation, models for a particular official profile (e.g., Ralph Stevens), an official type (e.g., referee), an official type for a particular formation (e.g., a referee positioned during a kickoff), and the like. Such models may consider all three dimensions (x, y, z) of the tag location data for each tag (e.g., 102 of FIG. 2B) and may further consider different tag position arrays (e.g., two tag implementations—one proximate each shoulder as in FIG. 2B, eleven tag implementations—one proximate each shoulder, one proximate each elbow, one proximate each hand, one proximate each knee, one proximate each foot, and one proximate the head).

In one embodiment, the official dynamics engine 324 determines a multi-dimensional official location per unit time for each official based on the tag location data, other tag and sensor derived data, the official role data, and the official dynamics/kinetics models. Such multi-dimensional official location may include (1) a relative location of the official relative to the field of play, (2) a general orientation of the official (e.g., standing, squatting, laying the ground, sitting, etc.), and (3) a specific orientation of the official (e.g., arms raised, arms at hips, one hand grasping the wrist of the other arm, etc.).

The official dynamics engine 324 uses the real time tag location data stream from the locate engine 302, as well as the official role database 326 to provide accurate information about what a particular official is doing in real time (or near real time). The official dynamics engine 324 may further use tag and sensor derived data, received from the locate engine 302 in the depicted embodiment, to aid in determining not only where the official is, but also how that official's location is changing with time, velocity, acceleration, deceleration, orientation, or the like. For example, in one embodiment, the sensor derived data may comprise accelerometer data that may indicate that an official (or portion of an official) is accelerating or decelerating. The official dynamics engine 324 outputs multi-dimensional official location information per unit time. Such multi-dimensional official location information may include information regarding the official's location, how the location is changing with time, orientation of the official, motions or gestures of the official, or the like.

In some embodiments, the tag ID/filter 304 may determine that received tag and/or sensor derived data corresponds to the game ball (e.g., a ball such as the ball shown in FIG. 2C, which is used or capable of use in the field of play). Such ball correlated tag/sensor derived data is routed to the ball dynamics engine 330. While the ball engine 330 is not shown in communication with a "roles" database as in the case of some of the other processing engines, one of ordinary skill in the art will readily appreciate some ball role data may be used, such as a ball ID or the like, indicating that the received tag/sensor derived data is associated with a given ball.

The ball engine 330 may access a ball models database 332, which comprises data indicating how location data and other tag and sensor derived data correlates to particular ball events during play. The ball engine 330 may provide information regarding the ball's position/location (vertical and/or horizontal), how the location is changing with time, the velocity of the ball, the rotation of the ball, or the like for determining events during play. The ball engine 330 may output ball data streams to the event engine 322. In some embodiments, although not shown in FIG. 3, the ball engine may also output a data stream to other processing engines for analysis, such as to the play engine 318 for use in determining status of a play.

In some embodiments, the tag ID/filter 304 may determine that received tag and/or sensor derived data corresponds to a field marker (e.g., penalty flags, line of scrimmage markers, yards to gain markers, and the like). The tag ID/filter may then route such field marker correlated tag/sensor derived data to a field marker engine 334 for further processing. The field marker engine 334 may provide information regarding field marker location, how the location is changing with time, or the like, for determining events during play. The field marker engine 334 may output data streams to the event engine 322. In some embodiments, although not shown in FIG. 3, the field marker engine may also output a data stream to other processing engines for analysis, such as to the play engine 318 for use in determining the status of a play.

In some embodiments, a game clock 380 may be provided that is configured to keep an official time for a game or other tracked activity. In applications such as the depicted football application, the game clock is configured to count down from some standard period or quarter length (e.g., 15 minutes) and may be periodically stopped or started by one or more officials and/or the game operations system 342 as discussed in greater detailed below. While not separately illustrated in FIG. 3, the game clock 380 may further include a play clock, shot clock, pitch clock, or the like, which depending upon the application, may also be started and stopped by one or more officials and/or the game operations system 342.

The universal clock 385 provides a system time for the performance and analytics system 300. As will be apparent to one of ordinary skill in the art in view of this disclosure, the universal clock 385 is running clock for tracking, cataloging, and calibrating system actions, processes, and events. For illustrations purposes, the game clock 380 and the universal clock are shown as inputs for the event engine 322; however, in other embodiments, such clocks may provide inputs to any or all of the player dynamics engine 306, the team formation engine 312, the play engine 318, the event engine 322, the official dynamics engine 324, the field marker engine 334, the ball engine 330, and the model generation engine 338.

An event engine 322 may receive the outputs from the player dynamics engine 306, the team formation engine 312, the play engine 318, the official dynamics engine 324, the ball engine 330, the field marker engine 334, the weather data store 375, a game clock 380, and a universal clock 385 to determine events occurring during game play or to perform analytics, including predictive analytics, on game related data. In some embodiments, the event engine 322 determines such events and performs such analytics by comparing its received inputs to a historic data store 336 containing past events or analytics. In some embodiments, the event engine 322 outputs event data streams (e.g., one or more output events) to a number of systems including, without limitation, a visualization system 340, a game operations system 342, a camera control system 344, a team analytics system 346, a league analytics system 348, a statistics system 350, an XML feed and/or instant message feed 352, a historical data store/engine 336, or other systems as may be apparent to one of ordinary skill in the art in view of this disclosure.

In some embodiments, the event engine 322 may output event data streams that include the time delay between tag and/or sensor transmissions and the determination of the events such that other processes, such as a visualization system, game operations system, etc., may properly correlate to different inputs (e.g., video recording versus the determined events) so that the different inputs are synchronized. In other embodiments, the event data streams may include time stamps (game time stamp, universal time stamp, etc.) for determined events or other system processes. In this way, the performance and analytics system 300 or some downstream system can determine, inter alia, which events or processes occurred in-game (i.e., during a running game or play clock) or out-of-game (i.e., while the game or play clock were stopped).

In various embodiments, the event data streams or output events provided by the event engine may include tag events (e.g., battery low indication, error indication, etc.), sensor events (e.g., battery low indication, error indication, etc.), locate engine events (e.g., status indications, error indications), tag ID/Filter events (e.g., status indications, error indications), player dynamics engine events (e.g., status indications, error indications), player events (e.g., player tackled indication, player injured indication, etc.), official dynamics engine events (e.g., status indications, error indications), official events (e.g., official injured indication, etc.), ball engine events (e.g., status indications, error indications), ball events (e.g., new ball required indication, etc.), team formation engine events (e.g., status indications, error indications), team formation events (e.g., formation type indication, new formation indication, illegal formation indication, etc.), play engine events (e.g., status indications, error indications), play events (e.g., play type indications such as run, pass, punt, field goal, etc., play results, and in-play or sub-play events such as bootleg, 3 step drop, 5 step drop, 7 step drop, crossing pattern, hook pattern, fly pattern, drive block, pass block, spin move, swim move, press coverage, zone coverage, etc.), or any other events that may be apparent to one of ordinary skill in the art in view of this disclosure. A variety of additional event data streams or output events are described in connection with the analytics systems and control systems discussed below.

In one embodiment, the event engine 322 outputs an event data stream to the visualization system 340 that may be used by the visualization system to provide enhanced telecasts or game experiences for television broadcasts, streaming mobile device clients, and other media outlets, gaming systems, and other computer graphics visualization systems. Such event data streams may be used to provide enhanced graphics, displays, information, visualizations, and the like.

For example, and without limitation, the visualization system 340 may receive real time (or near real time) data including, without limitation, player ID, official ID, team ID, formation identifiers, play identifiers, pre-snap play probabilities, play diagrams, player route data, player speed data, player acceleration data, ball route date, ball speed data, ball acceleration data, player trend information, offensive team trend information, defensive team trend information, special teams trend information, and other tag and/or sensor derived data. In some embodiments, the visualization system 340 may be configured to provide a dynamically configurable interface that may be engaged by a user to select graphics or areas of focus. For example, in one embodiment, a user may configure the system to display possible passing lanes for a quarterback to his eligible receivers. In still other embodiments, the visualization system 340 may output a data stream for use in gaming systems, such as plays, player actions, or the like.

In gaming systems examples, the visualization system 340 may provide output of event data that may be configured for display via a gaming console or handheld device. Such visualization system outputs may, for example, provide for incorporating actual or predicted actions of a "live" player into a gaming environment. In some embodiments, the visualization system may also access stored computer generated or user created avatars for use with the event data stream.

In one embodiment, the event engine 322 outputs an event data stream to the game operations system 342 that may be used by the game operations system to coordinate, manage, or assist in the coordination or managing of game operations including, without limitation, the game clock 380 (and optionally the play clock), down and distance determination, score board operations, penalty enforcement, and the like. For example, and without limitation, the game operations system 342 may receive real time (or near real time) data from the event engine 322 including, without limitation, a clock start indication, a clock stop indication, a play start indication, a play end indication, a reset play clock indication, a $1^{st}$ down indication, a $2^{nd}$ down indication, a $3^{rd}$ down indication, a $4^{th}$ down indication, a turnover indication, a yard to gain indication, a 5 yard penalty indication, a 10 yard penalty indication, a 15 yard penalty indication, an end of quarter indication, an end of half indication, and an end of game indication.

Said differently, the event engine 322 may determine a number of events that may be output to the game operations system or other devices. Such events may include, without limitation, a ready for play event (e.g., an official has spotted the ball at the line of scrimmage and started a play clock in a football example, a pitcher has received the ball from his catcher in a baseball example, or the pins have been set in a bowling example), a start of play event (e.g., the ball has been snapped in a football example, the pitcher has begun his pitching motion or wind-up in a baseball example, or a bowler has begun his bowling motion in a bowling example), and an end of play event (e.g., the official has blown a whistle in a football example, an umpire has called a third strike in a baseball example, or the nine pins have been knocked down in a bowling example). Such events may be used to determine plays, formations, and to output play diagrams (e.g., graphs or plots of participant location versus time from a start of play event to an end of play event).

The event engine 322 may be further configured to output a play result to the game operations system 342 or other device. Such play results may include, for example and without limitation, a gain of twelve yards, a loss of three yards, an interception, a touchdown, a first down, and the like in football embodiments; a ball, a strike, a fly-out, a single, a double, a home run, a run scored, and the like in baseball embodiments; and a gutter, a strike, a spare, and the like in bowling embodiments.

As would be apparent to one of skill in the art, the various engines and/or output systems may include security measures, such as encryption, access permissions, and the like, to secure system inputs and outputs. In some embodiments, the engines and/or output systems may comprise security measures to prevent hacking, jamming, transmission interception, etc. to prevent interference from outside parties, such as third parties attempting to gain information that may be advantageous in wagering, for example.

In one embodiment, the event engine 322 outputs an event data stream to the camera control system 344 that may be used by the camera control system to engage or transition engagement between one or more television, film, or other cameras to capture game events. For example, and without limitation, the camera control system 344 may receive real time (or near real time) data including, without limitation, an engage or disengage camera 1 indication, an engage or disengage camera 2 indication, an engage or disengage camera 3, . . . and an engage or disengage camera n indication. In some embodiments, the event engine 322 may output camera control indications (e.g., event data) based on real time (or near real time) game activity (e.g., ball location data suggests that the ball is closest to a known field of view for camera 4 and, thus, an engage camera 4 indication is transmitted to the camera control system 344). In other embodiments, the event engine 322 may output camera control indications (e.g., event data) based in part on a prediction of game activity (e.g., ball position, acceleration, and direction data suggests that the ball has just left the quarterback's hand and is being passed along a direction and at a velocity indicative of being caught in the field of view of camera 4 and, thus, an engage camera 3 indication is transmitted to the camera control system 344). In other embodiments, the camera control system 344 may provide indications such as to tilt, pan, or zoom in connection with a particular camera based on event data or predicted actions, or set a location or point of view based on where a player, formation, or play may be best viewed.

In one embodiment, the event engine 322 outputs an event data stream to the team analytics engine 346 that may be used to generate real time (or near real time) analytics (e.g., player performance information, formation performance information, play performance information, and team performance information) concerning game activity that may be useful to individual teams. For example, in one embodiment, the team analytics engine 346 may use event data to determine actual game performance versus playbook design including, without limitation, an evaluation of player routes, offensive, defensive, and special teams formations, offensive blocking protection schemes, defensive blitzing schemes, and the like.

In another embodiment, the team analytics engine 346 may use event data to determine actual game performance versus historical game performance (such as by using historical data store 336) including, without limitation, an evaluation of game performance (e.g., player, team, offense, defense, special teams, etc.) versus prior year performance, prior game performance, prior quarter performance, prior possession performance, prior play performance, and the like. In this regard, as will be apparent to one of ordinary skill in the art, the team analytics engine 346 may be used to evaluate performance (e.g., the left tackle has missed three assignments), identify trends (e.g., the defensive team consistently sends a linebacker blitz against a spread offensive formation), make player substitutions (e.g., a second string left tackle has performed better historically against the right end of the defense and thus should be substituted for the starting left tackle), revise game plans, or provide alerts (e.g., the flanker has experienced significantly reduced speed, acceleration, and performance following being tackled and thus an alert should be generated to the training staff to ensure that such player is medically evaluated).

For example, in one embodiment, a trainer may have a device, such as a handheld device, tablet, etc., that may receive alerts regarding a particular player. The trainer may receive background information and/or past information on a player as well as what change the system has identified to cause the alert, such as a change in gait, slower route running, etc. The trainer may then be able to evaluate the player and provide input to the system regarding the player evaluation, such as if further attention is required or if the player can return to play. In some embodiments, such alert and evaluation results may also be provided to the league analysis system, such as for use in determining injury trends or the like.

In some embodiments, the team analytics engine 346 may be used to alert a team (e.g., coaches) to focus on specific players who are performing sub-par versus their normal (historical) performance, such as by plays or by teams. In some embodiments, the team analytics engine 346 may further output analysis results to the historical data store 336 or the like, for use in future analysis and/or the building or updating of various models.

In one embodiment, the performance and analytics system is configured to evaluate player performance by correlating at least one tag to the player; receiving blink data (and other tag derived data) transmitted by the at least one tag; determining tag location data based on the blink data; receiving player role data; comparing the tag location data to player dynamics/kinetics models based at least in part on the player role data; determining player location data based on the comparing the tag location data to the player dynamics/kinetics models; and determining player performance information based on comparing the player location data to stored player location data. In some embodiments, the stored player location data may be stored to the historical data store 336 and may include player location data for the actual player to be evaluated (e.g., Frank Smith, left tackle, #55) and/or player location data for another player (e.g., Fred Johnson, left tackle, #65) who plays a similar position to the actual player to be evaluated. In still other embodiments, the stored player location data may include competitive data based on the performance of the actual player against an opposing player (e.g., the left tackle blocked the right defense end successfully in five prior match-ups, the defensive back caused a delay by the wide receiver of 2 seconds in running a passing route by applying press coverage, etc.).

In another embodiment, the performance and analytics system is configured to evaluate official performance by correlating at least one tag to the official; receiving blink data (and other tag derived data) transmitted by the at least one tag; determining tag location data based on the blink data; receiving official role data; comparing the tag location data to official dynamics/kinetics models based at least in part on the official role data; determining official location data based on the comparing the tag location data to the official dynamics/kinetics models; and determining official performance information based on comparing the official location data to stored official location data. In some embodiments, the stored official location data may be stored to the historical data store 336 and may include official location data for the actual official to be evaluated and/or official location data for another official who held a similar position (e.g., referee, umpire, etc.) to the actual official to be evaluated.

In one embodiment, the event engine 322 outputs an event data stream to the league analytics engine 348 that may be used to generate real time (or near real time) analytics concerning game activity that may be useful to a league (i.e., a collection of teams). For example, in one embodiment, the league analytics engine 348 may use event data to improve game safety by identifying injury trends (e.g., player concussions occur at a higher rate when an offensive team runs crossing passing routes from a spread formation against a 3-4 defense, etc.). In another embodiment, the league analytics engine 348 may use event data to evaluate rule changes (e.g., a rule change intended to speed up game play is or is not achieving its intended result). In still another embodiment, the league analytics engine 348 may use event data to improve officiating (e.g., determining the accuracy of official calls). In some embodiments, the league analytics engine 348 may further output analysis results to the historical data store 336 or the like, for use in future analysis and/or the building or updating of various models.

In one embodiment, the event engine 322 outputs an event data stream to the statistics engine 350 that may be used to generate real time (or near real time) statistics concerning game activity. Such statistics may include, without limitation, offensive statistics (e.g., passing, rushing, receiving, turnovers, touchdowns scored, etc.), defensive statistics (e.g., tackles, sacks, interceptions, turnovers generated, etc.), special teams statistics (e.g., punt length, punt hang time, average return, long return, field goal accuracy, etc.), play diagrams, length of play statistics (e.g., 4.8 second average play, 22 second average pre-snap formation period, etc.), player participation statistics (e.g., John Smith participation in 42 of 68 offensive plays, etc.), summary statistics (e.g., top scorers, fantasy points, minutes on offense, etc.), official statistics (e.g., penalties called, location tracking diagrams per play, etc.) and the like. In some embodiments, the statistics engine 350 may further output statistics and results to the historical data store 336 or the like, for use in future analysis and/or the building or updating of various models.

In one embodiment, the event engine 322 outputs an event data stream to the XML feed and/or instant messaging feed engine 352 that may be used to generate XML or instant messaging data streams that may include live data such as plays, scoring plays, other scoring info, results, top scorers, summary statistics, or the like.

In one embodiment, the event engine 322 may output an event stream that may be used to annotate or tag a game recording, for example, using visualization system 340, game operations system 342, or the like. For example, in one embodiment, the event engine 322 may flag, tag, or annotate certain events (e.g., plays, penalties, formations, clock start/stop, etc.) into a video recording or live data stream of a game for later playback or analysis. In some embodiments, any event identified by the event engine 322 may be flagged, tagged, or annotated to a video or other data stream to provide for ease of later identification. In this regard, various events may be readily searched, identified, stored to a database in an indexed way, and/or analyzed.

In some embodiments, the event engine 322 may determine events occurring proximate one or more play boundaries. For example, using outputs from the player dynamics engine 306, the ball engine 330, and the official dynamics engine 324 the event engine 322 may determine that a touchdown has been scored (i.e., a player has carried the ball across a goal boundary into the endzone). In particular, the event engine 322 may determine that a running back carried the ball (based on location data received from the ball engine and the player dynamics engine) across the goal boundary (based on field data), which was confirmed by the nearest official signaling touchdown by raising both arms (based on location data received from the official dynamics engine).

In some embodiments, the event engine 322 may output an event data stream to a historical data store/engine 336, which may store data generated by the various processing engines over time. The historical data store/engine 336 may be accessed by various systems, such as for use in providing analytics or generating new models. For example, historical data store/engine 336 may provide historical data to model generation engine 338, which the model generation engine 338 may use in learning (or developing) new play or formation models that should be added to the respective model databases. In some embodiments, the historical data store/engine 336 may be accessed by the analytics and statistics systems to generate more in-depth analytics or statistics. In some embodiments, the historical data store 336 may comprise prior event and tag derived data received by the system for each individual player (e.g., John Smith) and may also comprise player data received from other sources, such as from manual input tools (i.e., such as using a form or template) or external data sources (e.g., other statistics databases, etc.).

In some embodiments, the event engine 322 may output an event data stream that may be used in conjunction with historical results, such as from historical data store 336, for determining odds for outcomes of various team matchups. For example, the event data stream and historical event data may be analyzed to generate and/or change predicted odds for outcomes of each play, etc., which may be used in a wagering system or the like.

In some embodiments, the team analytics system 346 may provide an interface tool (i.e., perhaps through the model generation engine 338) configured to allow a team to input future plays (i.e., a game plan). Such future plays may be tested against historical data stored to the historical data store 336 in order to determine a probability for success. For example, the team analytics system 346 may be configured to allow a team to virtually test an individual play intended to be run from a given offensive formation against defenses that were historically run against such offensive formation. As will be apparent to one of ordinary skill in the art in view of this disclosure, the team analytics system 346 may be configured to allow a team to virtually test its game plan against another team, specific players, specific formations, specific blocking protections, specific blitz packages, specific weather conditions, and the like.

In one embodiment, the team analytics system 346, or any other engine or system, may be configured with access security controls (e.g., password protection schemes, etc.) sufficient to limit access to team proprietary data (e.g., game plan information, player injury data, etc.) to individual teams. In this regard, game integrity may be preserved by ensuring that proprietary data of a first team is not obtained by a competing second team.

In some embodiments, the event engine 322 and its corresponding output systems (i.e., the visualization system 340, the game operations system 342, the camera control system 344, the team analytics system 346, the league analytics system 348, the statistics system 350, the XML feed/IM feed system 352, and the historical data store/engine 336) may be configured to provide different levels of specificity for the output data. For example, an individual team may receive output data breaking down the specific details for each play and the player dynamics for the play, such that the team may determine the performance of each player in executing the specifics of a play versus an intended design. In contrast, similar yet less detailed output may be provided to all teams such as basic play diagrams and standard statistics for the players.

In some embodiments, one or more of the engines shown in FIG. 4, such as, without limitation, the team formation engine, the play engine, the event engine, or the like, may output lists or ranked lists of probable output events (e.g., locations, formations, plays, events, etc.) for display to a user via a graphical user interface (e.g., PC, tablet, mobile device, etc.) and/or for use by downstream engines or systems. In other embodiments, the above described engines may select from the ranked list of probable events a most probable event, or more simply a "probable event" (e.g., probable location, probable formation, probable play, probable blocking technique, probable passing route, etc.), that either has the highest probability indicator among the ranked list or has a probability indicator above a pre-defined threshold.

In some embodiments, the user may validate or confirm an output event (e.g., a location, a formation, a play, or an event) to improve system operation. For example, in one embodiment, the event engine 322 may determine that the following events may have occurred each with a respective probability indicator shown in parenthesis: completed pass—12 yard gain for the offense (68%); completed pass—10 yard gain for the offense (21%); incomplete pass—0 yard gain for the offense (19%). This ranked list may be displayed to an official via a mobile device who may select and confirm the correct output event, which in this example is the completed pass for a 12 yard gain for the offense. In this regard, as will be apparent to one of ordinary skill in the art in view of this disclosure, the system may employ a user to break ties or close calls (e.g., probabilities within 10 percent, etc.) or to improve the accuracy of models, input weighting allocations, and the like.

In still other embodiments, the performance and analytics system may determine or predict participant locations, formations, plays, or other events despite temporary or sustained losses of blink data for one or more tags (e.g., due to transmission failures associated with multipath effects, line-of-sight blockages, etc.). For example, in one embodiment, the performance and analytics system: receives first tag location data for a first participant (e.g., a ball carrier) during a first time period (e.g., an in-play period representing the first 3 seconds of a play); receives subsequent first tag location data for the first participant during a second time period (e.g., a second in-play period representing the second 3 seconds of a play); receives second tag location data for a second participant (e.g., the ball carried by the ball carrier) during the first time period; and determines (or predicts) subsequent second tag location data for the second participant during the second time period based at least on: the first tag location data for the first participant during the first time period, the subsequent first tag location data for the first participant during the second time period, and the second tag location data for the second participant during the first time period.

The above determination or prediction may be further improved using tag derived data and sensor derived data. For example, the performance and analytics system may receive first sensor derived data (e.g., time-of-flight sensor data or other tag and sensor derived data suggestive of a relative proximity between the first participant and the second participant) for the first participant during the first time period; receive subsequent first sensor derived data for the first participant during the second time period; and determine the subsequent second tag location data for the second participant during the second time period further based at least on: the first sensor derived data for the first participant during the first time period, and the subsequent first sensor derived data for the first participant during the second time period.

In still other embodiments, the above determination or prediction of second participant location may be improved by comparing participant location at various times to formation and/or play models. Such comparisons may further include field data, and participant role data. For example, if we maintain the above example whereby the first participant is a ball carrier and the second participant is a ball, the performance and analytics system may determine or predict the location of the ball (i.e., in circumstances where tag or sensor transmissions from the ball are blocked) during a pre-snap period by determining that the ball carrier is aligned in a stationary location in the backfield. By comparing such ball carrier location data to formation models, the system may determine that the ball is most likely positioned at the line of scrimmage proximate the center.

Similarly, in another embodiment, perhaps where the first participant is a quarterback and the second participant is a left guard, the performance and analytics system may determine or predict the location of the left guard in any given play or time period based upon comparing movements of the quarterback to formation and play models. For example, quarterback movement from a snap position to a drop back passing position may be suggestive that the left guard is positioned in a pass blocking position proximate the line of scrimmage. Alternatively, quarterback movement from a snap position to a hand-off position may be suggestive that the left guard is positioned up field of the line of scrimmage in a run blocking position.

Example Visualizations

Figure 5:
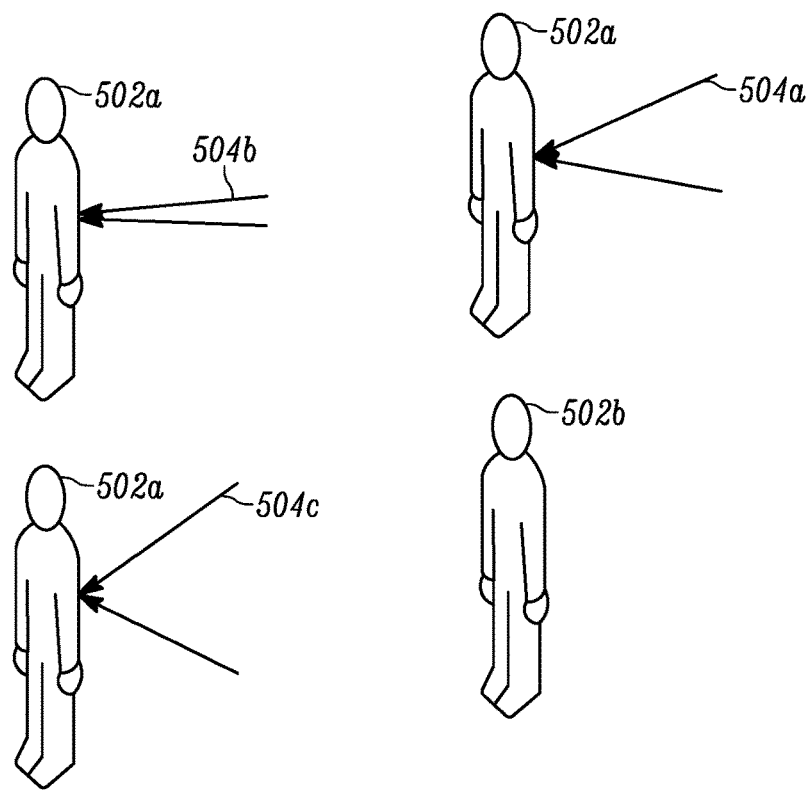

FIGS. 5-23 illustrate example visualizations that may be output from a visualizations module 340, based on inputs from one or more processing engines, such as the event engine 322, as discussed in FIG. 4. The utilization of the location system may allow for visualizations to be rendered in real time or near real time automatically, e.g. without user interaction, or in response to user selections. FIG. 5 illustrates a visualization for indication of relative speed of a participant. Various participants 502 may be depicted on the event field, e.g. American football field, not shown. The participants 502 may be the broadcast picture, such as event footage, or a representation of the participant on the event field, such as an event field schematic. The visualization system 340 may receive location data, event occurrence data, analytics data, or the like from a processing engine, such as the event engine, which may include speed data associated with the participant 502. A participant in motion 502a may have a speed variable arrow trailer 504 generated by the visualizations module 340. The speed variable arrow 504a trailer may be a predetermined length and have a predetermined width for a moving participant 502a. The speed variable arrow trailer 504b may increase in length and/or narrow width to indicate increasing speed. The speed variable arrow trailer 504c may decrease in length and/or increase in width to indicate a decrease in speed. Additionally or alternatively, a change in speed may be indicated by in other ways, such as changing color, e.g. red for increase in speed and blue for decreasing speed, a numerical value appended to the participant and/or the arrow trailer, or the like. A participant 502b which is not in motion may be depicted without the speed variable arrow trailer 504 and/or a numerical indicator indicating a zero speed.

Figure 6:
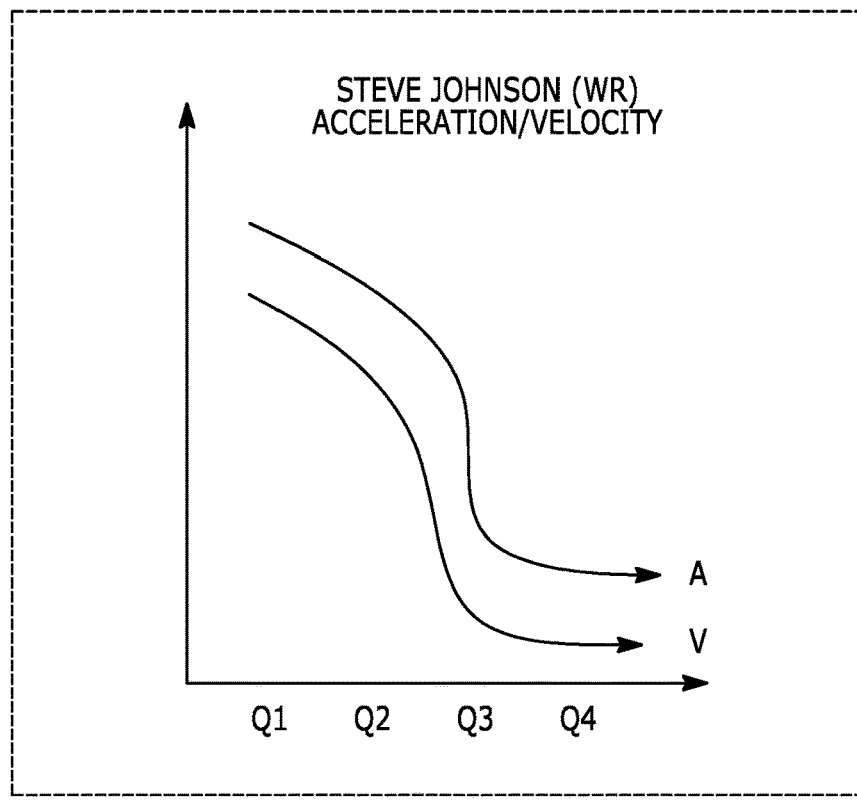

FIG. 6 illustrates a visualization of a chart of participant statistical attributes over time such as average acceleration or average velocity. The visualizations module 340 may receive statistical data from a processing engine, such as the event engine 322 and player data from a database, such as the player role data base 308. The visualizations module 340 may generate a graph for selected attributes, such as average velocity, average acceleration, average distance, or the like for a period of time, e.g. per play, period, quarter, game, or the like. It is noted that a line graph is used as an example, but it would be readily apparent to one of ordinary skill in the art that other graph or charts, such as bar graphs, pie charts, scatter plots, or the like, may be used to display the participant data. The visualization may indicate the selected participant, e.g. Steve Johnson, position or role, e.g. wide receiver (WR), and attributes, e.g. acceleration/velocity.

In some example embodiments, the visualization system 340 may depict historical data, which may be received from a database, such as the historical data database 336. The historical data may be depicted in the same graph or in an additional graph for comparison or contrast. The comparisons may be used to determine participant health or performance characteristics by team staff or for broadcast. For example, a change in performance may indicate an injury or medical evaluation needed, or a need to rotate a fatigued player. Additionally, the comparisons may be used to adjust wagering odds for gaming.

In some example embodiments, the visualization system may depict multiple participant data. The visualization system 340 may depict the additional participant in the same graph or additional graph for comparison. These comparisons may be used by the team to determine which players are fatigued performing well, and indicate when to rotate players. Additionally or alternatively, these comparisons may be used to compare players on the same or opposing teams for analysis of players.

Figure 7:
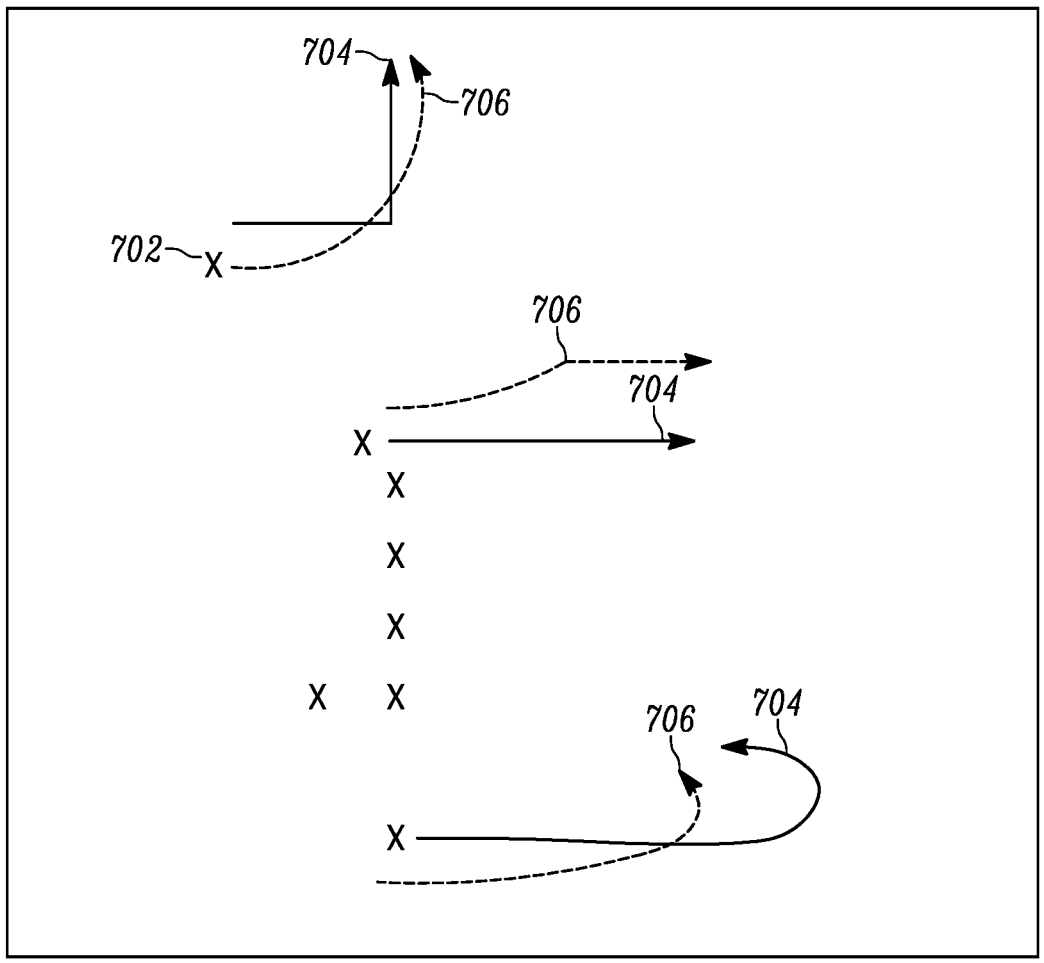

FIG. 7 illustrates an example visualization of a play diagram with an overlay of the location data associated with the play execution. The visualizations module 340 may receive the play diagram data from a database, such as the play model database 320, and location data for a plurality of participants from a processing engine, such as the event engine 322. The visualization system 340 may overlay the location data 706 for the respective participants 702 on the play diagram paths 704. The resultant visualization may depict a comparison of the actual paths taken by the participant 706 and the path dictated by the play diagram for the respective player participants 704, in some embodiments.

For example, in one embodiment, the visualization system 340 may determine a selected play based on comparing the location data to the play diagram data. the visualization system 340 may then determine an actual route for one or more participants of the plurality of participants based on the location data and generate an accuracy visualization interface by comparing the actual route for each of the one or more participants to the selected play. In some embodiments, the accuracy visualization interface may provide out of position indicators associated with variances between the actual route of the participants and one or more predicted routes drawn from the selected play of the play diagram data. In some embodiments, the out of position indicators may visually indicate instances where the actual route varies from the one or more predicted routes by more than a threshold amount.

In some example embodiments, the play diagrams may also include the anticipated paths of opposing players in response to the play. The visualization system 340 may depict the opposing player anticipated paths and actual paths. The comparison of the play diagram paths 704 and actual paths 706 may allow the coaches and players to determine failures of a play, such as a player not following the dictated path, the opposition not responding as anticipated, or the like. Additionally, strengths of plays may be determined, such as the play was well executed, the opposition responded as anticipated, or the deviation of a player made the play work better. These determinations may be used to generate new plays, discard plays, modify plays, or the like.

For example, in one embodiment, the visualization system 340 may further receive location data for a plurality of opposing participants during the play period and determine a selected opposing play based on comparing the location data for the plurality of opposing participants to the play diagram data. The visualization system 340 may then determine an actual opposing route for one or more of the opposing participants based on the location data for the plurality of opposing participants and generate an opposing accuracy visualization interface by comparing the actual opposing route for each of the one or more opposing participants to the selected opposing play. The opposing accuracy visualization interface may include out of position indicators associated with variances between the actual opposing route and one or more predicted opposing routes.

In some example embodiments, a plurality of accuracy visualization interfaces may be generated for a plurality of selected plays occurring during a period of a game, such as a quarter or the like and/or may be generated for a plurality of selected plays occurring during an entire game. In some example embodiments, the accuracy visualization interface may comprise a visual representation of the actual route overlaid relative to one or more predicted routes drawn from the selected play.

Figure 8:
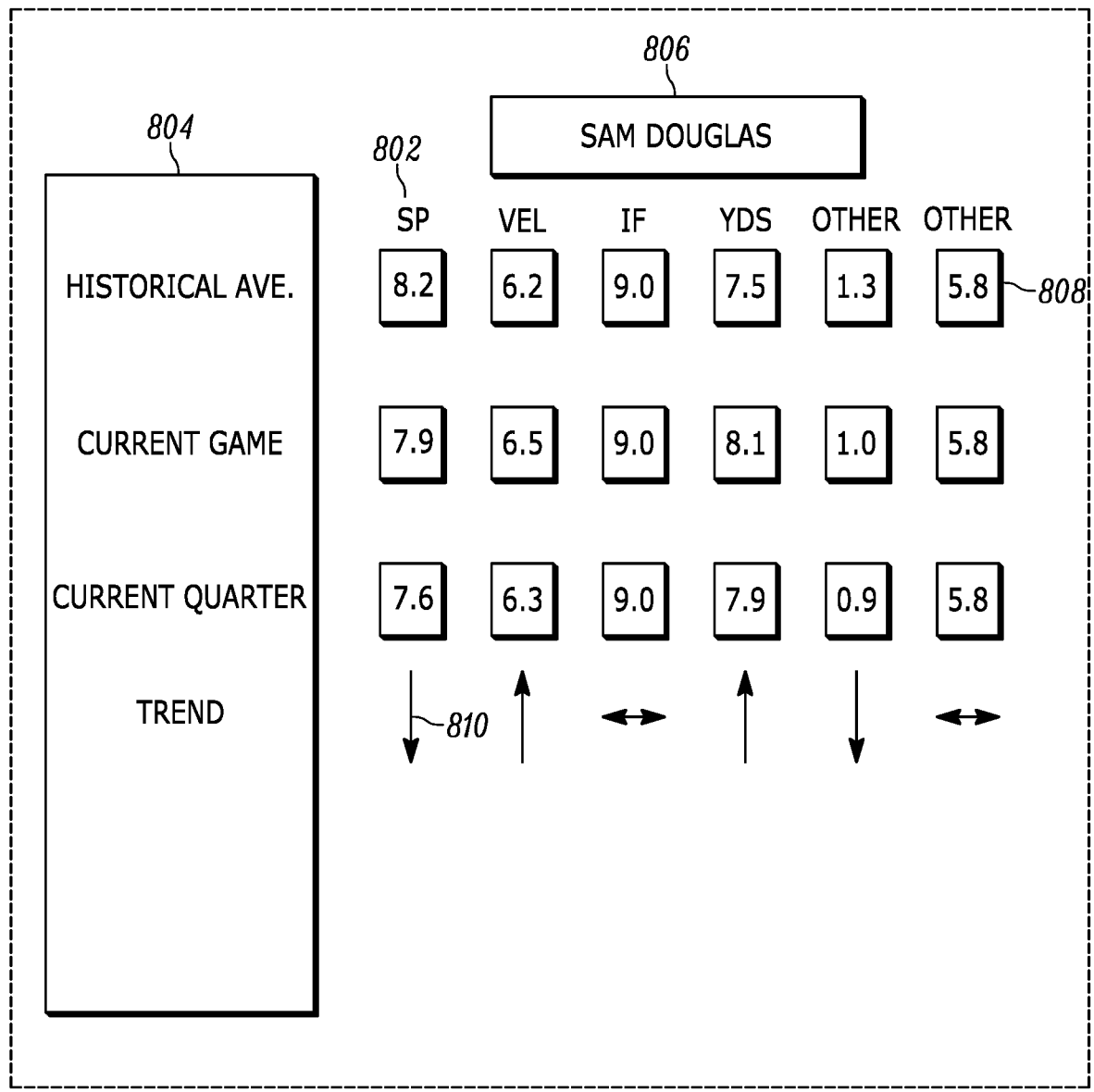

FIG. 8 illustrates an example visualization of player statistics comparison chart. The visualization system 340 may receive statistical data from a processing engine, such as event engine 322, and historical data from a database, such as historical database 336. The visualization system 340 may depict various participant attributes 808 over various time periods 804, such as the historical average, game average, quarter average, play data, or the like. The statistical data may include speed (SP), velocity (Vel), impact force or tackles (IF), yardage (Yds), or any other statistical information that may be determined by the locating system. The visualization system 340 may depict the name 806 and/or position of the player participant and indications of the attributes displayed 802 and depict the attribute over multiple periods of time, for example, the historical average for the player, the average for the game and a current quarter average. Additionally, the visualization may indicate a trend 810 for the statistic compared to a historical average or pervious period average.

In an example embodiment, the historical and current statistical data may be output to a game operations module 342. The game operation module 342 may provide the visualization to subscribing games, for example American football video games. The video game may use the visualization to display game characters statistics in relation to the equivalent real player. In some example embodiments, the game may adjust game character attributes based on the statistical data for the real player. For example, the game may use a predetermined attribute value for speed, based on historical averages. In an instance in which the statistical data is received by the game, the game may adjust the game character speed attribute, such as lowering the speed attribute, to match the received data. The game may use the visualizations for the selection menu for players and/or to adjust the physical attributes, adding a layer of realism to the game.

FIGS. 9 to 11 illustrate example visualizations that may be generated for various training or sporting events, such as high jump, hurdles, sprints, agility drills, or the like. The visualization system 340 may receive location data and statistical information associated with the participant, from a processing engine, such as the event engine 322. The location data may be two dimensional, such as position on a field or track, or three dimensional including distance from the ground. The visualization system may generate a visualization of the event and display associated statistics.

Referring to FIG. 9, the visualization system 340 may depict an icon 902 and field 906, such as a person and the high jump marker. The participant icon may be stationary illustrating the activity in a general manner, or may be active, such as traveling in the general manner of the participant. In some example embodiments, the visualization may also include statistical information 904, such as height of the jump and the air time. In some example embodiments, the icon and event depictions may be footage of the activity with the statistical information and/or a height reached line 910 overlaid on the footage.

Referring to FIG. 10, the visualization system may depict an icon 1002, an event field 1012, and or an event title 110, such as 40 yard dash (40 yrd). Similar to FIG. 9, the icon 1002 or actual participant, in the case of an event footage with overlay, may travel across the event field 1012. Statistic data titles 1104 and statistic data 1004 and 1006 may be displayed as the icon 1002 progresses across the field. The statistical data may include a total time for the event 1006, and/or split times 1008 for subsections of the event, such as each 10 yards.

Referring to FIG. 11, the visualization may depict an icon 1102, an event field 1112, attribute titles 1104, and statistical data 1106 and 1108. In an embodiment such as agility exercise with cones 1112, the participant or icon 1102 may travel though the field 1112 and a travel path 1114 may be rendered. The visualization may include the attributes, such as acceleration, velocity, or the like, and times which may be total time/average attribute for the event 1106 or split time or attribute 1108. The visualization may be used to determine how the participant traveled through the field for analysis of the performance, such as direction change analysis. Similar visualizations may be used for an event in which there is vertical movement, such as hurdles.

In an example embodiment, in which there is separate vertical movement and horizontal movement, such as hurdles, the visualization system may generate two visualizations for the same event. For example, one visualization for a horizontal plane and one visualization for a vertical plane which may provide a more meaningful analysis of the total event than a single visualization.

Figure 12:
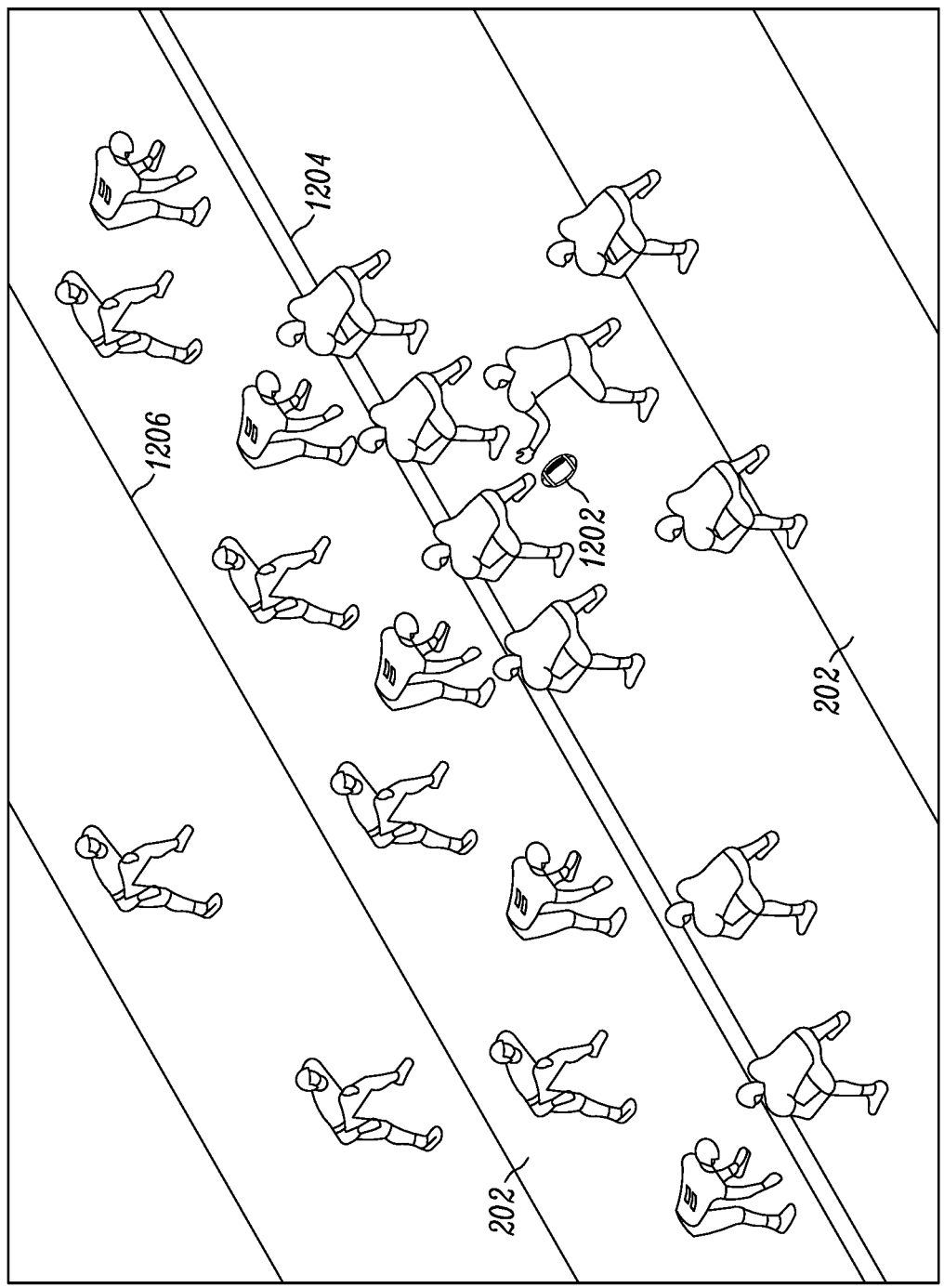

FIG. 12 illustrates an example visualization depicting footage of a football game in which the object ball 1202, scrimmage line 1204, and down line 1206 are overlaid on the field. The visualization system 340 may receive location data and field marker data from a processing engine, such as the event engine 322. The visualization system 340 may generate a visualization which may indicate the location of the ball 1202 in relation to the field and, more specifically, the scrimmage line 1204 and/or down line 1206. In some embodiments, the ball 1202 and/or the scrimmage or down lines 1204/1206 may indicate when the ball has passed the line, such as by changing color, e.g., red to green, or format, e.g., dotted versus solid line. Further, the scrimmage line and/or down line depictions may be based on the location data for the placement of the ball by the referee, and or the down markers used on the field to indicate the down line, providing a more exact indication of downs. Similar visualizations may be generated for other events which use an invisible line for progression of the game, or in instances where participant location in relation to a line may be important to a game, such as the three point line in basketball.

Figure 13:
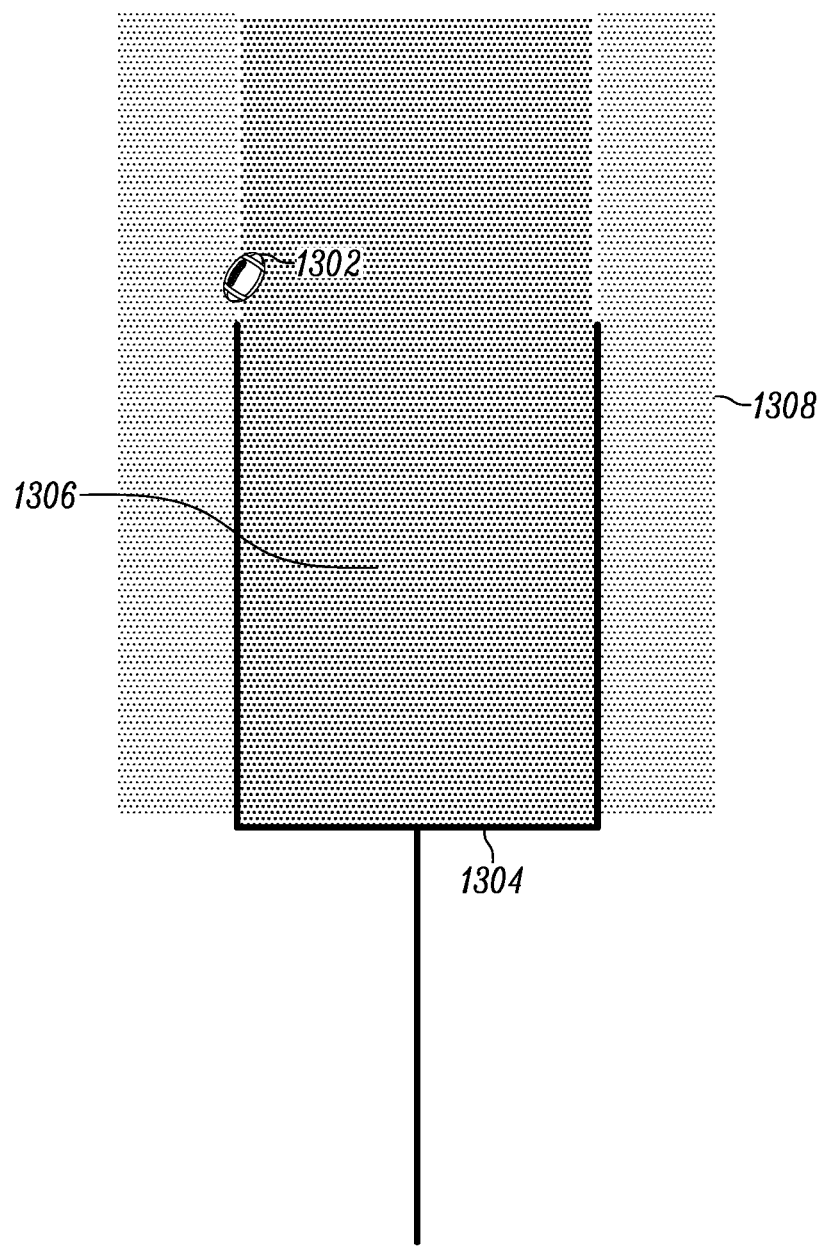

FIG. 13 depicts an example visualization of a goal post in American football with indicators for successful goal or unsuccessful goal. The visualization system may receive location data for the ball 1302 from a processing engine, such as the event engine 322. The location data may indicate the three dimensional travel of the ball 1302 in relation to the field and/or the goal posts 1304. The visualization may be a depiction of the goal post 1304 and/or footage of the goal post with information overlay. The goal post 1304 may have indication areas such as the successful goal area 1306 and an unsuccessful goal area 1308. The visualization may indicate the successful goal area 1306 and unsuccessful goal area 1308, such as by assigning colors to each, e.g., green for successful and red for unsuccessful. The area in which the ball 1302 traveled may be indicated in the visualization, and in some instances highlighted, such as brightening the area 1306 or 1308 which the ball passed and dulling the area in which the ball did not pass, providing a more precise indication of successful goals. In some example embodiments, the successful goal area 1306 may be subdivided into the area within the extension of the goal posts 1304 and the area above the extension of the goal posts. Although, both areas would indicate a successful goal, the division may indicate more precise goal and control of the ball 1302. Similar visualizations may be used in other events, such as rugby, croquet, soccer, hockey, or the like.

Figure 14:
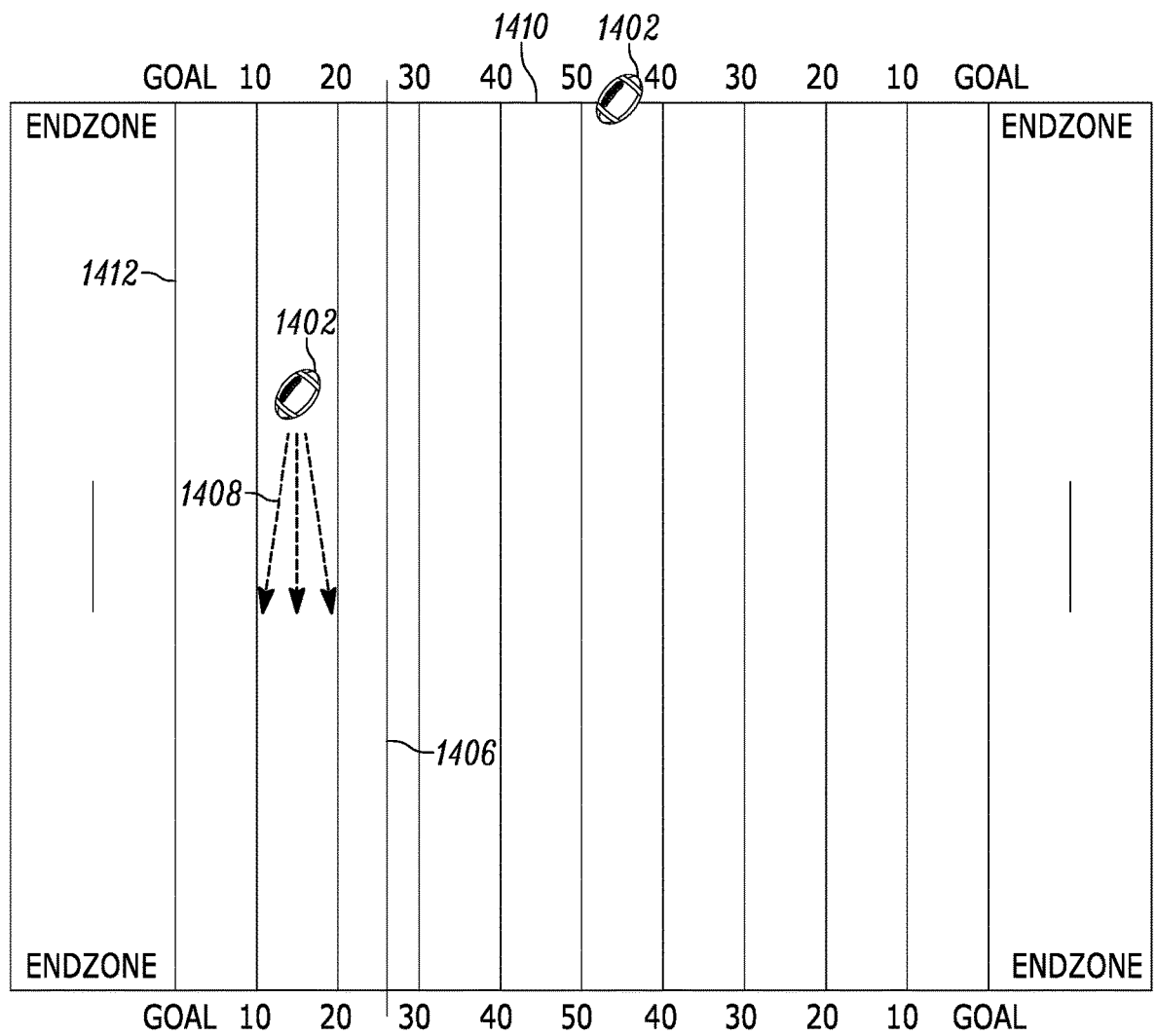

FIG. 14 illustrates an example visualization depicting the travel of a ball in relation to invisible game lines. The visualization system 340 may receive ball location data and field data from a processing engine, such as the ball engine 330, field marker engine 334, or event engine 322. The visualization system 340 may generate a visualization depicting the location and travel of the ball 1402. The travel lines 1408 may indicate when or if the ball has passed an invisible line, such as a boundary line 1410.

In another embodiment, the travel lines 1408 may indicate the travel of the ball 1402 in relation to the scrimmage line. For example, the travel line 1408 may be blue if parallel to or traveling away from the line of scrimmage 1406 (when starting from behind the line of scrimmage), indicating a lateral pass. The travel line 1408 may be green if the ball 1402 is traveling toward the line of scrimmage 1406 (when staring from behind the line of scrimmage), indicating a forward pass. Similar visualizations may be used in other events, such as baseball foul lines, soccer boundary lines, basketball boundaries, or the like.

Figure 15:
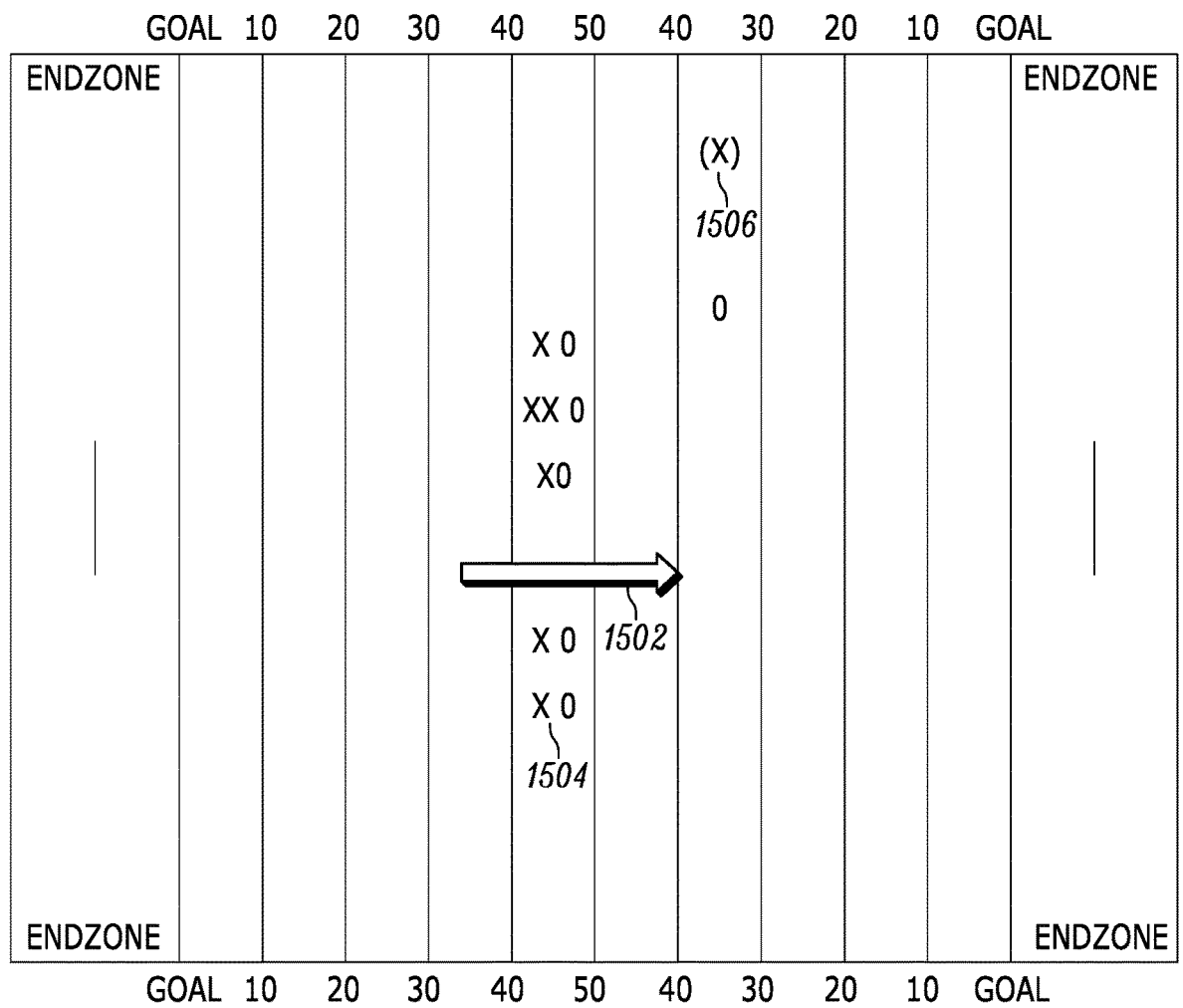

FIG. 15 illustrates an example visualization depicting formation openings or open receivers. The visualization system 340 may receive formation data, location data, play data, or the like form one or more processing engines, such as the play engine 318, team formation engine 312, player dynamics engine 306, event engine 322, or the like. The depictions of the player participants and field may be a schematic representation, as shown, or an overlay on top of event footage. One or more of the processing engines may identify a formation 1504 and an opening in the formation, in which a player may travel relatively unobstructed. The visualization system 340 may depict the formation in the position on the field and overlay an opening indication 1502 based on the determination of an opening.

Additionally or alternatively, one or more of the processing engines may determine a receiver is open to receive a pass from the quarterback, or other player. The determination may be based on role data and the location of the participant 1506 and the location of the closest opponent player, as well as the formation data and play data. In some embodiments, one or more opposing participants based on location data, formation data, and play data for use in determining that a receiver participant is open to receive a pass. The visualization system may generate a visualization, such as an open receiver interface, that is configured to visually indicate the one or more open receiver participants. The visualization may highlight the open receiver 1506 by changing color, circling, or the like. The automatic determination and indication may be utilized by broadcasters explaining the play, which may replace the manually drawing and overlaying. Similar visualizations may be used in other events such as soccer, rugby, lacrosse, hockey, or the like.

In some embodiments, the visualization system may modify or update the open receiver interface for each of the one or more open receiver participants based on the degree of openness of each open receiver participant. In some embodiments, the degree of openness of each open receiver may be based on how close an opposing participant is to the receiver or based on velocity vectors of the opposing players in the area of the receiver. In some embodiments, the open receiver interface may provide indicators for each open receiver and may modify the appearance of the indicators based on how open the receiver is. For example, a circle may be drawn around each open receiver position and the color or other visual format of the circle may be changed based on how open a receiver is to receive a pass. In some embodiments, a comparison of defensive play data and offensive route data may be generated during a play period and may be used to predict possible receivers who may come open for receiving a pass.

In some example embodiments, the direction of travel of the participants, such as the receiver, quarterback, and/or opposing players may be used to determine and display the open receiver. For example, there may be a visualization depicting the receivers which the quarterback is looking at based on location tags mounted on a helmet. In another example, in which the receiver 1506 may be near an opposing player, but the player is traveling in a direction that would not likely intersect with the receiver, a data engine may determine that the receiver is open.

Figure 16:
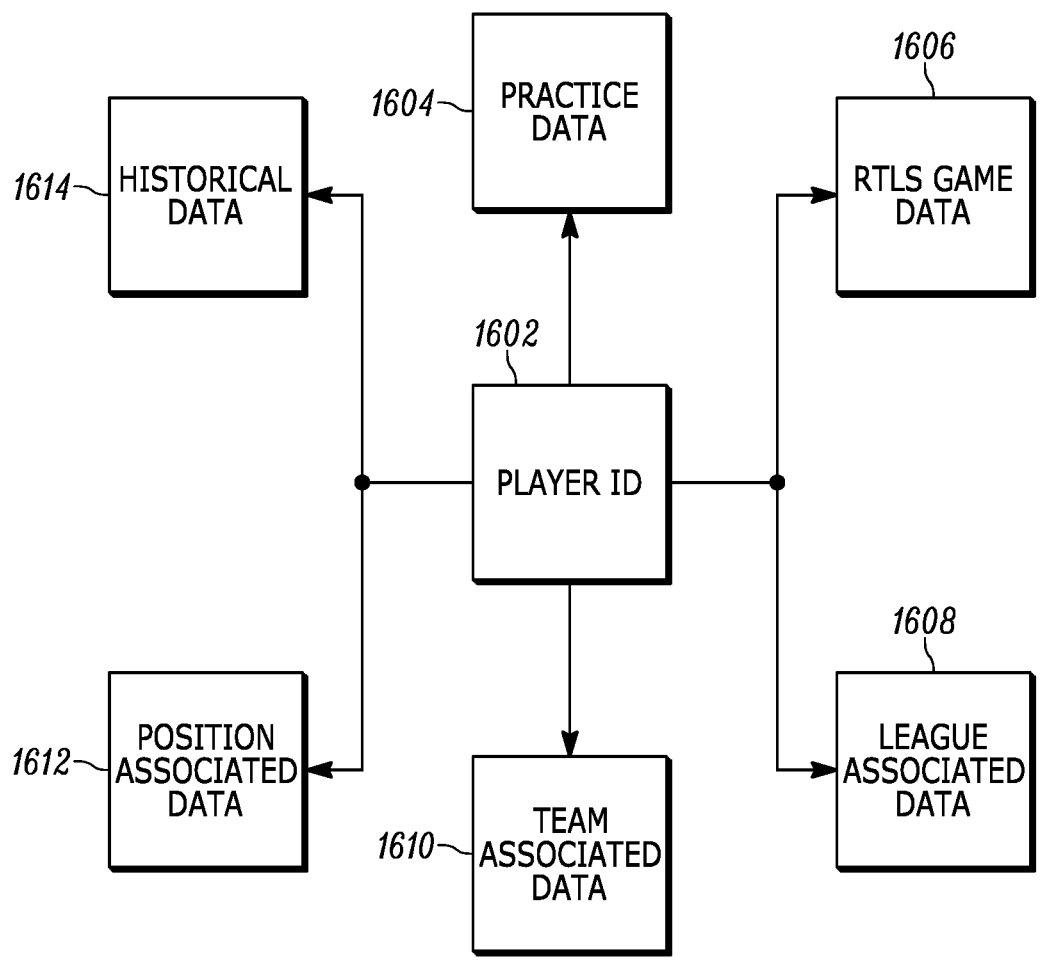

FIG. 16 illustrates an example visualization for a web menu for selection and/or subscription to various location system data outputs and visualizations. The user may select data based on the player ID 1602. A user may additionally select data associated with the Player ID 1602, such as practice data 1604, location system game data 1606, league associated data 1608, team associated data 1610, position related data 1612, historical data 1614, or the like. In some example embodiments, data may be selected by selecting a team or league ID and then selecting data such as player, position, games, or the like. The data mapping provided may allow for quick selection and association of players to the selected data and allows for additional data to be viewed by the user, e.g., practice data and game data, which may not have been previously available or not available in real time.

Figure 17:
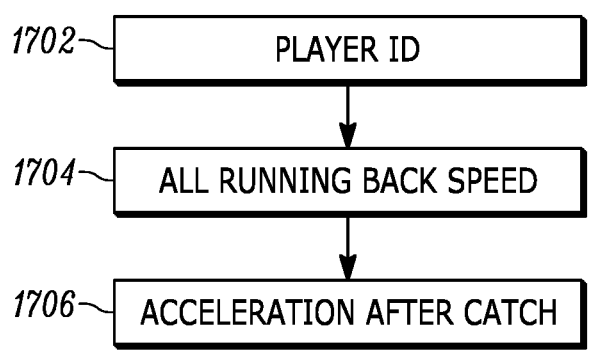

FIG. 17 illustrates an example visualization for a selection tree for location system data and/or visualizations. The user may select a unit ID 1702, such as a player ID, team ID, or league ID, or the like; and one or more attributes to display as a portion of the visualizations 1704 and/or 1706, for example, running back speed and acceleration after catch. In an example embodiment, the data selected and displayed as a portion of the visualization does not have to be funneled information. For example, attribute data associated with a player may be displayed, average speed for all running backs or each of the running backs, and acceleration after catch for each running back. Allowing for a full attribute list for one or more players to be viewed with one or more attributes for the league or the players of the league or team. The selectablity and breadth of the analytic statistical data of the location system allows for more comparisons to be made between players while maintaining or reducing the complexity of generating the comparison visualization.

Figure 18:
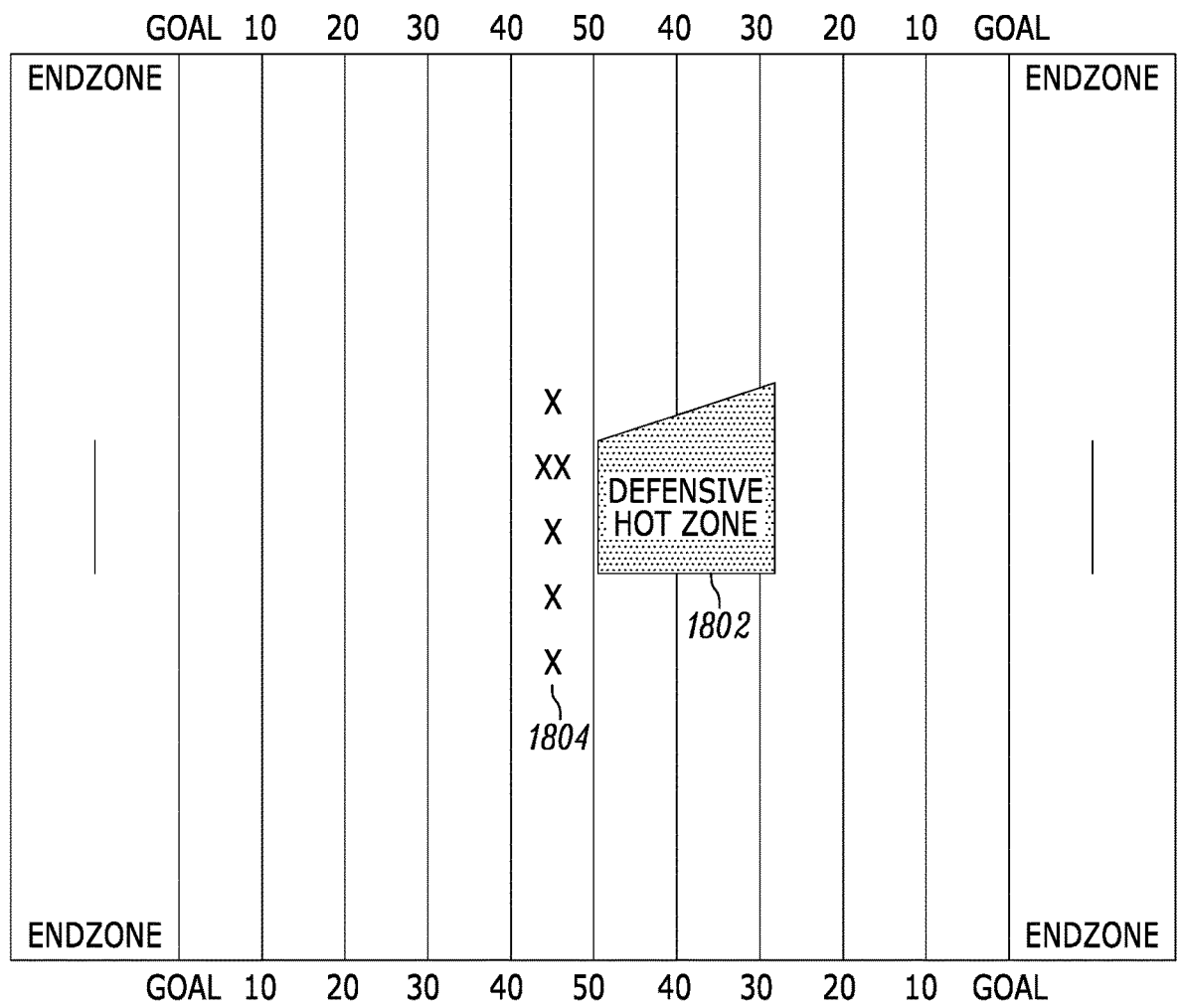

FIG. 18 illustrates an example visualization showing an area in which the defense has been active during the game or based on a particular play. The visualization engine 340 may receive a hot zone indication 1802 form a processing engine, such as the event engine 322. The processing engine may use historical data from a database, such as the historical data database 32, and location data from the current game to determine a hot zone 1802, in which the opposing team or defensive team has been concentrated during the game, period, or the like. Additionally or alternatively, one or more of the processing engines, such as the team formation engine 312, may determine an offensive formation 1804, and determine a defensive hot zone based on historical data associated with the formation from previous games. The visualization system 340 may over lay the defensive hot zone on a field schematic and/or game footage. These visualizations may provide information for coaches to adjust plays, design new plays, or call a different play. Additionally, it may provide a visual for broadcasters to discuss likely defensive movements and predictability. Similar visualizations may be used for receivers positions based on a formation or other player predictions.

Figure 19:
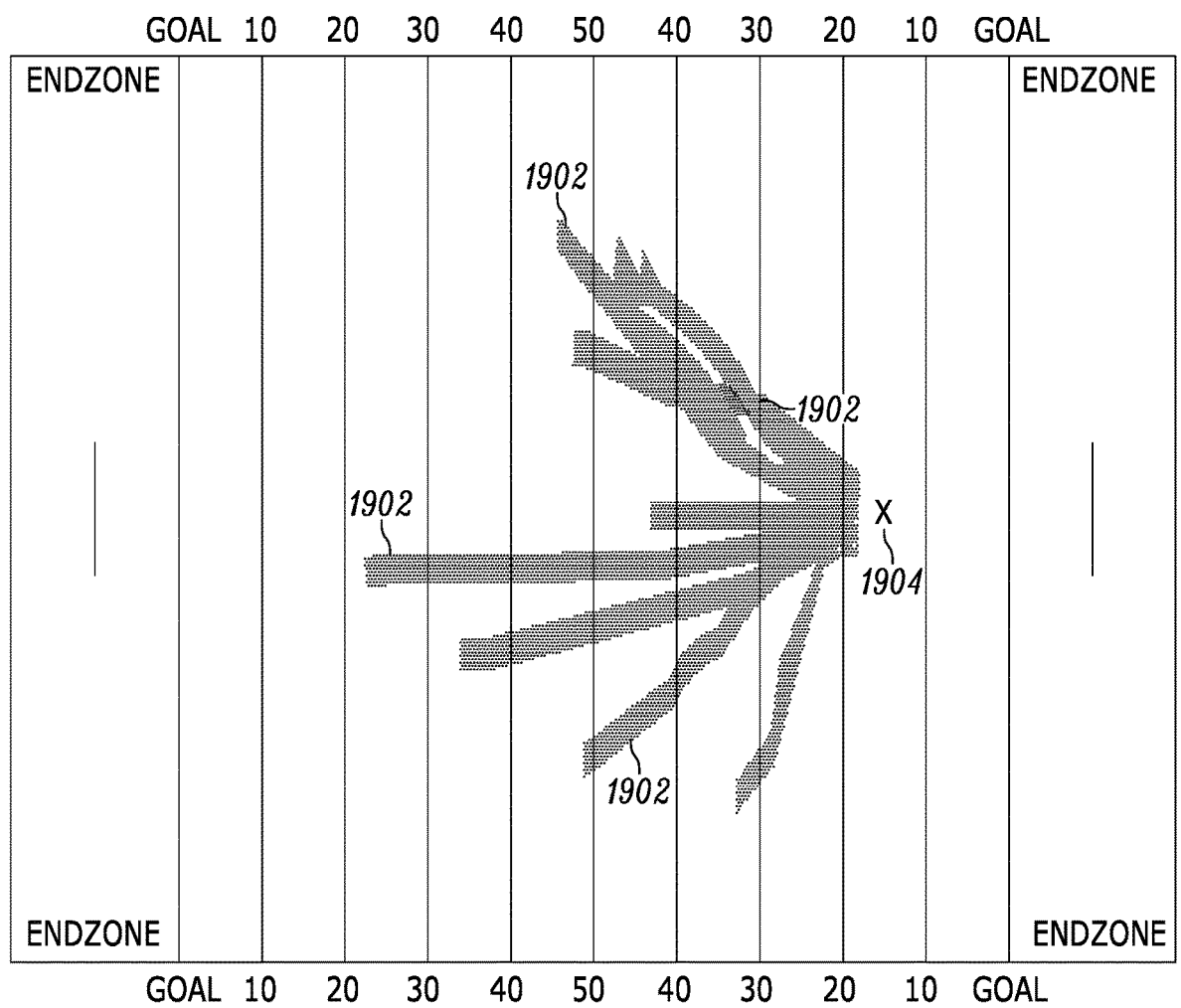

FIG. 19 illustrates an example visualization depicting travel density relative to a starting point. The visualization system 340 may receive location data for a player participant or ball 1904 from a processing module, such as the ball engine 330, locate engine 302, or event engine. The visualization system 340 may additionally receive historical location data from a database, such as the historical data database 336. The visualization system 340 may plot the location data path and highlight areas in which the player or object has traveled more than one time, such as a darker shade of the travel color. The darker color may indicate the density of the travel path use. The density of the travel path 1902 use may be used to predict future passes or movements of players 1904.

Figure 20:
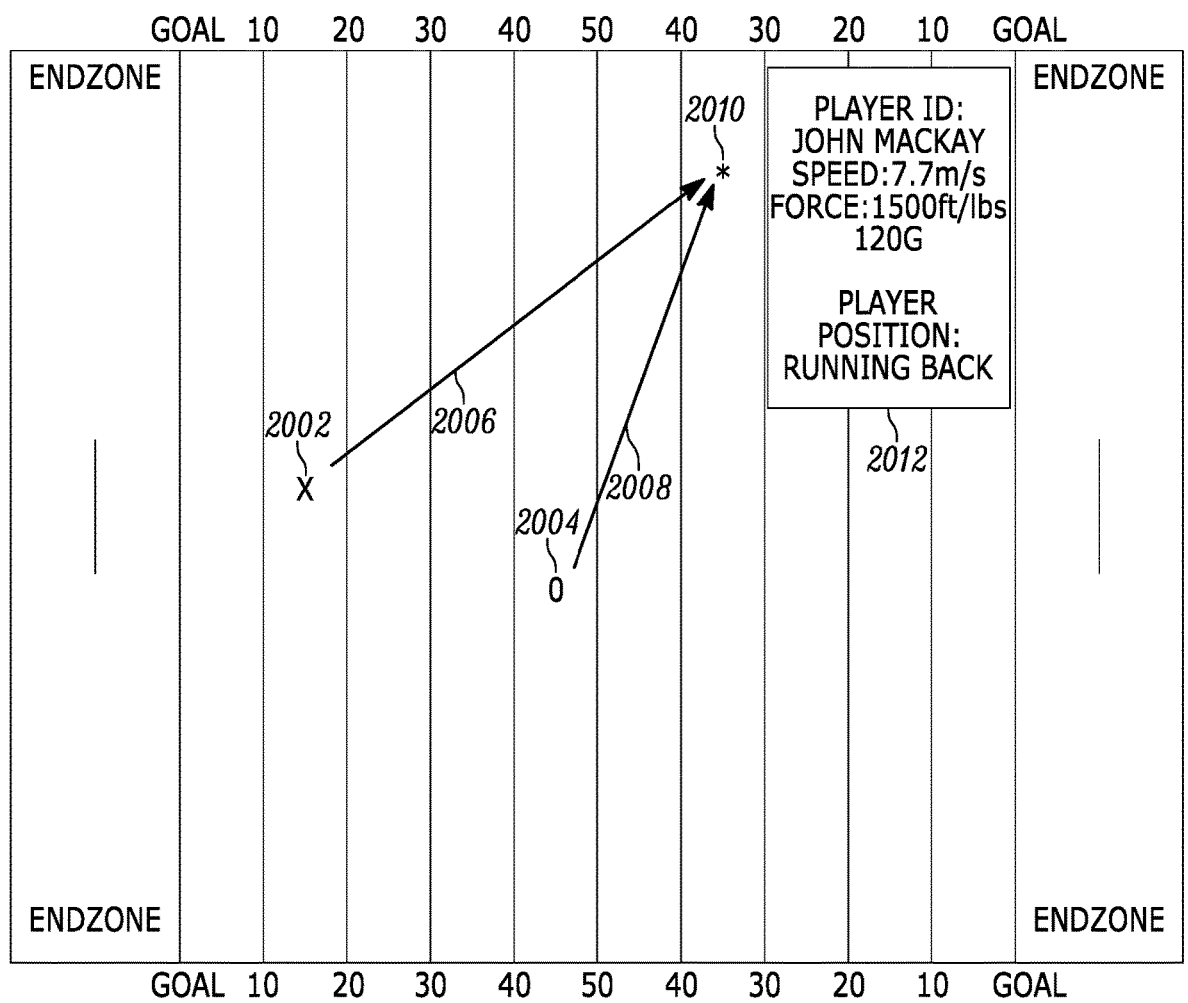

FIG. 20 illustrates an example visualization of an impact diagram. The impact diagram may be overlaid on a field schematic or on game footage. The visualization system 340 may receive location data, sensor data, statistical data, or the like from one or more of the processing engines, such as event engine 322. In an instance in which a processing engine determines an impact has occurred, for example based on the location data and the sensor data for two or more participants, the location of the impact 2010 is indicated on a visualization, such as a impact visualization interface, (e.g., on a field schematic or game footage overlay), generated by the visualization system 340. In some embodiments game camera data associated with the impact indication 2010, e.g., a camera which may have captured the impact event, may be tagged or otherwise associated with the impact event for later retrieval. The visualization may include the starting positions of the players 2002 and 2004 which have impacted and the respective player travel paths 2006 and 2008. In some embodiments, the visualization may include a statistic indication 1212, which may include information for one or more players associated with the impact. The statistic indication may include the name of the player, player ID, speed at impact, net force of the impact in foot-pounds or gravitation units, player position, or the like. Additionally or alternatively, the statistic indication may be color coded based on the number of impacts associated with the player and/or the force of the impact.

In some embodiments, speed and acceleration at and after impact may be determined and indicators such as variable arrow trails, such as described in FIG. 5, may be included in the impact visualization interface and may be illustrated approaching and departing the location of the impact. In some embodiments, participant specific data, such as participant mass, may be received and factored in for determinations of force or momentum approaching an impact.

The visualization may be used by broadcasters to describe the impact, such as a tackle, or by medical staff to assess players and determine if medical assistance or evaluation is necessary. In some embodiments, the tagging of event footage correlated with the impact allows medical personnel to watch the impact footage for assessment, without having to watch irrelevant footage.

Figure 21:
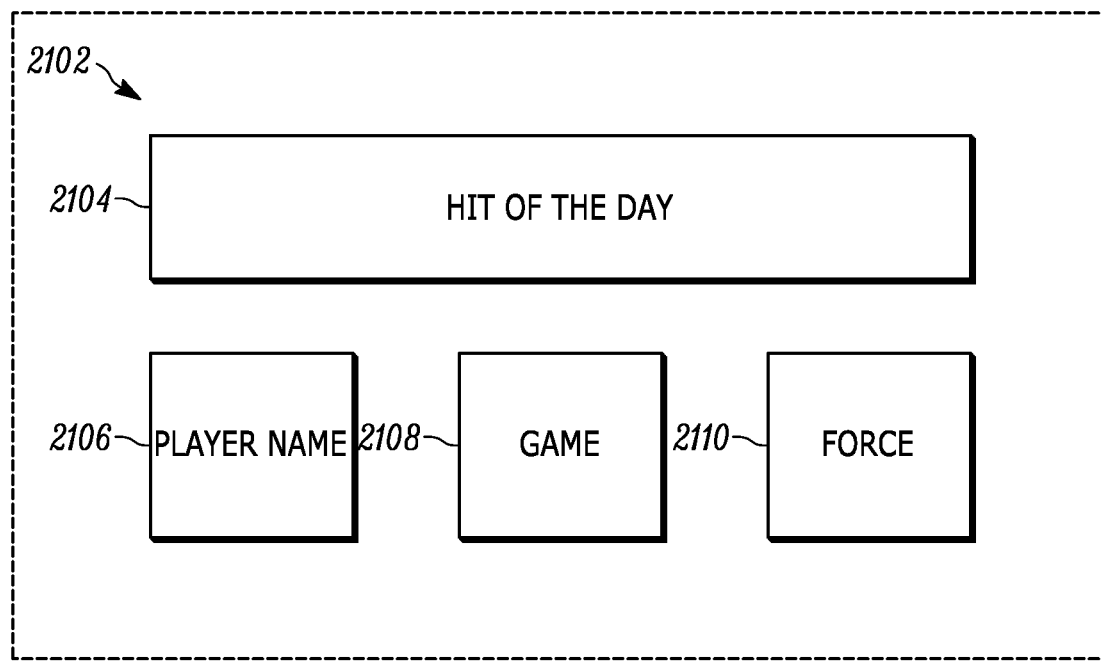

FIG. 21 illustrates an example visualization of a statistical indication for statistics. The visualization may be a portion of the statistic indication 2012 of FIG. 20 or a separate visualization. The visualization 2102 may include the name of the statistic 2104, e.g., hardest hit of the game or day. The visualization 2102 may also include the name of the player 2106, the game when the statistic occurred, and the statistical data 2110, such as impact force.

Figure 22:
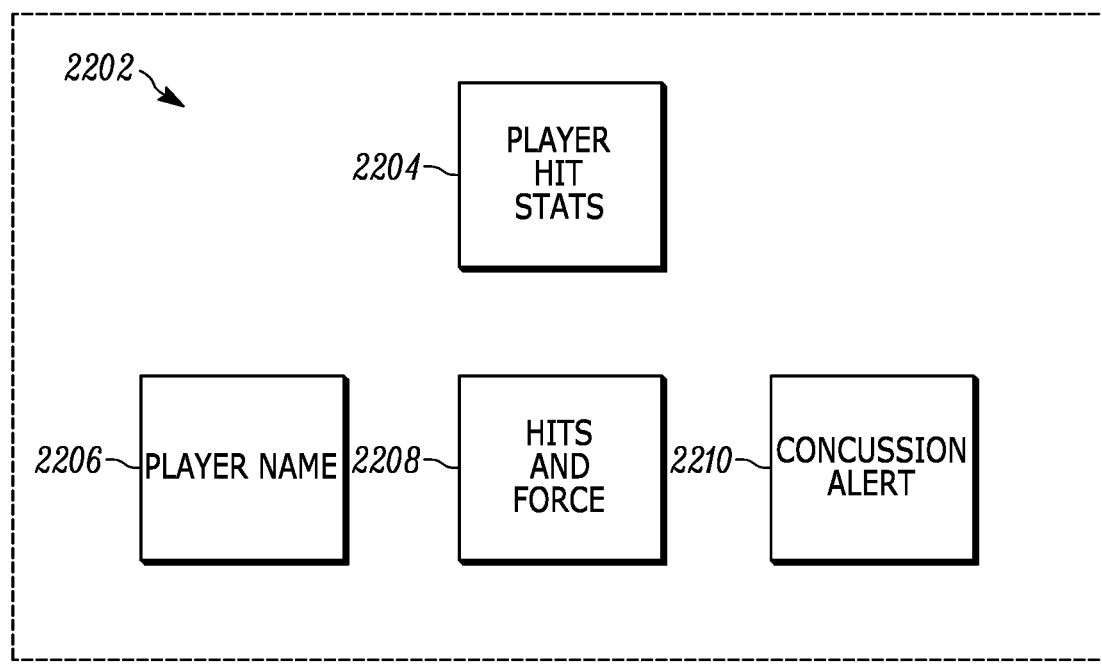

FIG. 22 illustrates an example visualization for a statistical indication for statistics. The visualization may be a portion of the statistic indication 2012 of FIG. 20 or a separate visualization. The visualization 2202 may include the name of the statistic data 2204, such as player hit or impact statistics, speed, or the like, the player name 2206, the statistic data 2208, such as number of hits and or force or hits, speed, or the like, and alerts 2210, such as medical alerts based on number of impacts or impact force, or rotation alert based on a player performance statistic falling below a predetermined threshold value or change in performance statistic. For example, a low force impact may have a green alert, indicating that no medical evaluation is required. Several impacts, e.g., a number of impacts satisfying a predetermined threshold, or an impact of a predetermined force may cause a yellow alert, indicating that the player should be evaluated when the player leaves the field. A high number of impacts, e.g., a number of impacts satisfying a second predetermined threshold, cumulative impact force above a predetermined threshold, or a single impact above a second threshold may cause a red alert, indicating that the player should be evaluated as soon as possible, and possibly removed from play. In one such embodiment, the alerts may be concussion alerts associated with impacts sensed on or near the players head, e.g., helmet.

Figure 23:
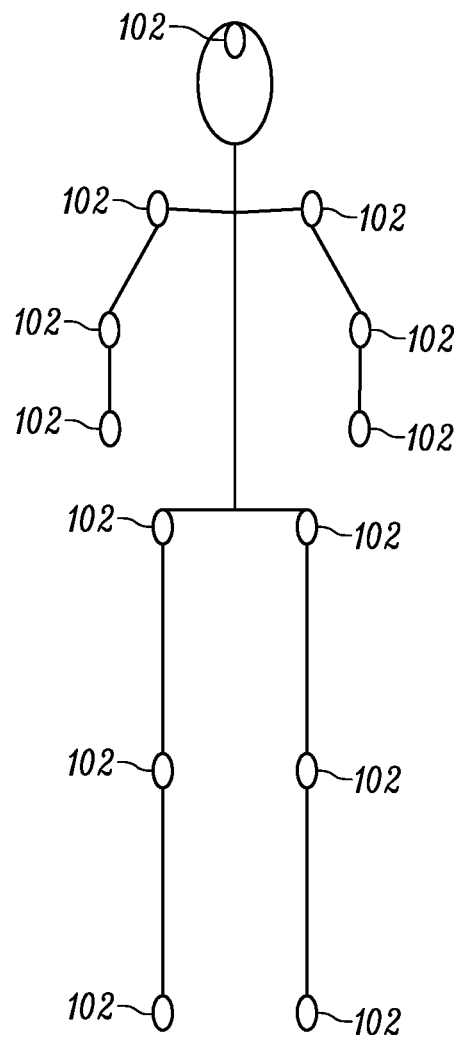

FIG. 23 illustrates an example visualization for motion analysis. The visualization system 340 may receive the location data associated with a plurality of location tags 102 and/or sensor data associated with one or more tag from a processing engine, such as the locate engine 302, player dynamics engine 306, or event engine 322. The visualization system 340 may generate a three dimensional model of the participant motion for a specified time period. The model of participant motion may be based on tags 102 or sensors placed at predetermined point of the participant body, such as head, shoulders, elbows, wrists, hips, knees, ankles, or the like. In instances in which there is an impact between players, the participant motion model may depict the body motion of both participants and may differentiate the participants by color or other methods.

The participant motion model may be utilized for broadcasting the motion of players in a play, or analyzing an impact or injury. Medical staff may use the participant motion model to understand the cause of an injury to make informed decisions in treatment. Additionally, the participant motion model may be used to analyze the performance of players, for example the catch and turn of a receiver. The participant motion model may inform the player as to the exact movements, e.g., the speed and placement of each foot after catching the ball, and allow for correction of motion to increase performance.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for providing enhanced event visualizations based on location data, the method comprising:
   receiving, by a visualization processor, location data and sensor data for participants;
   determining an impact indication for the participants based at least in part on the location data and the sensor data;
   determining, by the visualization processor, an impact location based on the impact indication, the location data, and the sensor data for the participants;
   generating an impact visualization interface configured to visually indicate impact data associated with the impact indication;
   determining speed at impact data for the participants based at least in part on the location data and the sensor data;
   determining acceleration at impact data for the participants based at least in part on the location data and the sensor data; and
   generating a first speed at impact indicator and a first acceleration at impact indicator for a first one of the participants as part of the impact visualization interface, wherein the first speed at impact indicator comprises a first speed variable arrow trail approaching the impact location that varies in appearance based on the speed at impact data, and the first acceleration at impact indicator comprises a first acceleration variable arrow trail approaching the impact location that varies in appearance based on the acceleration at impact data.

2. The method of claim 1, further comprising:
   determining speed after impact data for the participants based at least in part on the location data and the sensor data;
   determining acceleration after impact data for the participants based at least in part on location data and the sensor data; and
   generating a first speed after impact indicator and a first acceleration after impact indicator for the first one of the participants as part of the impact visualization interface.

3. The method of claim 2, wherein the first speed after impact indicator comprises a second speed variable arrow trail departing the impact location that varies in appearance based on the speed after impact data, and the first acceleration after impact indicator comprises a second acceleration variable arrow trail departing the impact location that varies in appearance based on the acceleration after impact data.

4. The method of claim 1, further comprising:
   generating impact statistic information; and
   providing the impact statistic information as part of the impact visualization interface.

5. The method of claim 1, further comprising:
   receiving participant data for the participants, the participant data comprising participant mass data;
   generating force and momentum approaching impact data based on the participant mass data, the location data, and the sensor data, wherein generating the impact visualization interface is based on the force and momentum approaching impact data.

6. The method of claim 1, further comprising:
   determining a starting point for at least one of the participants based at least in part on the location data; and
   generating a participant start indicator for the at least one of the participants as part of the impact visualization interface.

7. The method of claim 6, further comprising:
   determining a route for the at least one of the participants based at least in part on the location data; and
   generating a participant route indicator for the at least one of the participants as part of the impact visualization interface.

8. An apparatus comprising at least one processor and at least one memory including computer program code, the at least one memory and the computer program code configured to, with the at least one processor, cause the apparatus to at least:
   receive location data and sensor data for participants;
   determine an impact indication for the participants based at least in part on the location data and the sensor data;
   determine an impact location based on the impact indication, and the location data, and the sensor data for the participants;

generate an impact visualization interface configured to visually indicate impact data associated with the impact indication;
determine speed at impact data for the participants based at least in part on the location data and the sensor data;
determine acceleration at impact data for the participants based at least in part on the location data and the sensor data; and
generate a first speed at impact indicator and a first acceleration at impact indicator for a first one of the participants as part of the impact visualization interface, wherein the first speed at impact indicator comprises a first speed variable arrow trail approaching the impact location that varies in appearance based on the speed at impact data, and the first acceleration at impact indicator comprises a first acceleration variable arrow trail approaching the impact location that varies in appearance based on the acceleration at impact data.

9. The apparatus of claim 8, wherein the at least one memory and the computer program code are configured to, with the at least one processor, cause the apparatus to:
determine speed after impact data for the participants based at least in part on the location data and the sensor data;
determine acceleration after impact data for the participants based at least in part on the location data and the sensor data; and
generate a first speed after impact indicator and a first acceleration after impact indicator for the first one of the participants as part of the impact visualization interface.

10. The apparatus of claim 9, wherein the first speed after impact indicator comprises a second speed variable arrow trail departing the impact location that varies in appearance based on the speed after impact data, and the first acceleration after impact indicator comprises a second acceleration variable arrow trail departing the impact location that varies in appearance based on the acceleration after impact data.

11. The apparatus of claim 8, wherein the at least one memory and the computer program code are configured to, with the at least one processor, cause the apparatus to:
generate impact statistic information; and
provide the impact statistic information as part of the impact visualization interface.

12. The apparatus of claim 8, wherein the at least one memory and the computer program code are configured to, with the at least one processor, cause the apparatus to:
receive participant data for the participants, the participant data comprising participant mass data;
generate force and momentum approaching impact data based on the participant mass data and the location data and the sensor data; and
generate the impact visualization interface based on the force and momentum approaching impact data.

13. The apparatus of claim 8, wherein the at least one memory and the computer program code are configured to, with the at least one processor, cause the apparatus to:
determine a starting point for at least one of the participants based at least in part on the location data; and
generate a participant start indicator for the least one of the participants as part of the impact visualization interface.

14. The apparatus of claim 13, wherein the at least one memory and the computer program code are configured to, with the at least one processor, cause the apparatus to:
determine a route for the at least one of the participants based at least in part on the location data; and
generate a participant route indicator for the at least one of the participants as part of the impact visualization interface.

15. A computer program product comprising at least one computer readable non-transitory memory medium having program code instructions stored thereon which, when executed by an apparatus, cause the apparatus at least to:
receive location data and sensor data for participants;
determine an impact indication for the participants based at least in part on the location data and the sensor data;
determine an impact location based on the impact indication, the location data, and the sensor data for the participants; and
generate an impact visualization interface configured to visually indicate impact data associated with the impact indication;
determine speed at impact data for the participants based at least in part on the location data and the sensor data;
determine acceleration at impact data for the participants based at least in part on the location data and the sensor data; and
generate a first speed at impact indicator and a first acceleration at impact indicator for a first one of the participants as part of the impact visualization interface, wherein the first speed at impact indicator comprises a first speed variable arrow trail approaching the impact location that varies in appearance based on the speed at impact data, and the first acceleration at impact indicator comprises a first acceleration variable arrow trail approaching the impact location that varies in appearance based on the acceleration at impact data.

16. The computer program product of claim 15, wherein the program code instructions, when executed by the apparatus, cause the apparatus to:
determine speed after impact data for the participants based at least in part on the location data and the sensor data;
determine acceleration after impact data for the participants based at least in part on the location data and the sensor data; and
generate a first speed after impact indicator and a first acceleration after impact indicator for the first one of the participants as part of the impact visualization interface.

17. The computer program product of claim 16, wherein the speed after impact indicator comprises a second speed variable arrow trail departing the impact location that varies in appearance based on the speed after impact data, and the first acceleration after impact indicator comprises a second acceleration variable arrow trail departing the impact location that varies in appearance based on the acceleration after impact data.

18. The computer program product of claim 15, wherein the program code instructions, when executed by the apparatus, cause the apparatus to:
generate impact statistic information; and
provide the impact statistic information as part of the impact visualization interface.

19. The computer program product of claim 15, wherein the program code instructions, when executed by the apparatus, cause the apparatus to:
receive participant data for the participants, the participant data comprising participant mass data;
generate force and momentum approaching impact data based on the participant mass data and the location data and the sensor data; and generate the impact visualization interface based on the force and momentum approaching impact data.

20. The computer program product of claim 15, wherein the program code instructions, when executed by the apparatus, cause the apparatus to:
  determine a starting point for at least one of the participants based at least in part on the location data; and
  generate a participant start indicator for the at least one of the participants as part of the impact visualization interface.

21. The computer program product of claim 20, wherein the program code instructions, when executed by the apparatus, cause the apparatus to:
  determine a route for the at least one of the participants based at least in part on the location data; and
  generate a participant route indicator for the at least one of the participants as part of the impact visualization interface.

* * * * *